US006326470B1

(12) United States Patent
Cosgrove

(10) Patent No.: US 6,326,470 B1
(45) Date of Patent: Dec. 4, 2001

(54) ENHANCEMENT OF ACCESSIBILITY OF CELLULOSE BY EXPANSINS

(75) Inventor: Daniel J. Cosgrove, Pennsylvania Furnace, PA (US)

(73) Assignee: The Penn State Research Foundation, University Park, PA (US)

( * ) Notice: Subject to any disclaimer, the term of this patent is extended or adjusted under 35 U.S.C. 154(b) by 0 days.

(21) Appl. No.: 09/429,675

(22) Filed: Oct. 28, 1999

Related U.S. Application Data

(63) Continuation-in-part of application No. 08/834,327, filed on Apr. 15, 1997, now Pat. No. 5,990,283.
(60) Provisional application No. 60/105,906, filed on Oct. 28, 1998.

(51) Int. Cl.[7] .............................. C07K 1/00; C07K 14/00; C07K 16/00; C07K 17/00
(52) U.S. Cl. .......................... 530/370; 530/372; 530/375; 530/376; 530/377; 530/378; 530/379; 435/183; 435/195; 435/209
(58) Field of Search .................................... 530/370, 372, 530/375, 376, 377–379; 435/183, 195, 209

(56) References Cited

U.S. PATENT DOCUMENTS

| | | | |
|---|---|---|---|
| 3,844,890 | 10/1974 | Horikoshi et al. | 195/62 |
| 3,966,543 | 6/1976 | Cayle et al. | 162/158 |
| 4,004,976 | 1/1977 | Isaac | 565/598 |
| 5,175,275 | 12/1992 | Dobashi et al. | 536/56 |
| 5,959,082 | * 9/1999 | Cosgrove et al. | 530/370 |

OTHER PUBLICATIONS

McQueen–Mason et al. Proc. Natl. Acad. Sci. USA, vol. 91, pp. 6574–6578, Jul. 1994.*
Fry, Stephen C., *Physiologia Plantarium* 75:532–536, 1989.
Patel, Praful, in "Biotechnology Applications and Research", eds. Cheremisinoff, P.N. and Ouellette, R.P. pp. 534–562, Technomic Publishing Company, Inc., Lancaster, PA, 1985.

(List continued on next page.)

*Primary Examiner*—Dwayne C. Jones
*Assistant Examiner*—C. Delaceroix-Muirheid
(74) *Attorney, Agent, or Firm*—Zarley, McKee, Thomte, Voorhees & Sease

(57) ABSTRACT

Plant cell expansion is regulated by wall relaxation and yielding, which is thought to be catalyzed by elusive "wall loosening" enzymes. By employing a reconstitution approach, we initially found that a crude protein extract from the cell walls of growing cucumber seedlings possessed the ability to induce the extension of isolated cell walls. This activity was restricted to the growing region of the stem and could induce the extension of isolated cell walls from various dicots and monocots, but was less effective on grass coleoptile walls. Sequential HPLC fractionation of the active wall extract revealed two proteins with molecular masses of 29 and 30 kD, as measured by SDS-PAGE, associated with such activity. Each protein, by itself, could induce wall extension without detectable hydrolytic breakdown of the wall. We proposed the name "expansins" for this class of proteins. Expansins have been isolated from various plant sources including oat, cucumber, broccoli, celery, tomato, cotton, cabbage, and corn, and also from snail and its feces. These proteins weaken the intermolecular bonds between plant wall polysaccharides. They decrease the mechanical strength of commercial products made from polysaccharides, such as paper, and therefore present a novel approach in developing new technologies in industries which make use of such polysaccharides, such as in the paper industry, in the applications of polysaccharide gums and related products. These proteins moreover present a novel approach in the control of plant growth.

15 Claims, 33 Drawing Sheets

OTHER PUBLICATIONS

Taiz, L., *Ann. Rev. Plant Physiol.* 35:585–657, 1984.

Scopes, R.K., Chapter 3, Protein Purification, Principles and Practice, 2nd Ed., pp. 41–54, Springer–Verlag, New York, 1987.

Deutscher, M.P., Academic Press 1990, Guide to Protein Purification, pp. 174–193.

Fry, Stephen C., *Current Biology* 4(9):815–817, 1994.

Cleland, R.E., *Planta* 170:379–385, 1987.

Nishitani, K.and Tominaga R., *J. Biol. Chem.* 267(29):21058–21064, 1992.

Taiz, L., *Proc. Natl. Acad. Sci. USA* 91:7387–7389, Aug. 1994.

Shcherban, T.Y. et al., *Proc. Natl. Acad. Sci. USA* 92:9245–9249, Sep. 1995.

Bayer, E.A. et al., *Current Opinion in Structural—Biology* 8:548–557, 1998.

Cosgrove, D.J. et al., *Proc. Natl. Acad. Sci. USA* 94:6559–6564, 1997.

Li, Z–C et al., *Planta* 191:349–356, 1993.

McQueen–Mason, S. and Cosgrove, DJ, *Proc. Natl. Sci. USA* 91:6574:6578, 1994.

McQueen–Mason, S. and Cosgrove, DJ, *Plant Physiol.* 107:87–100, 1995.

McQueen–Mason, S. et al., *Planta* 190:327–331, 1993.

\* cited by examiner

ENHANCEMENT OF ACCESSIBILITY OF CELLULOSE BY EXPANSINS

This application is a continuation-in-part application of U.S. Ser. No. 08/834,327 filed Apr. 15, 1997 and also claims priority of U.S. Provisional Application Serial No. 60/105,906 filed Oct. 28, 1998.

FIELD OF THE INVENTION

The present invention relates to a new class of proteins, known as expansins, and isolation and utilization of same. These proteins have been identified in a wide variety of plant materials and have a variety of applications including, but not limited to, agricultural, food and industrial uses, such as use in paper industry as a catalyst for weakening the strength of paper products. For example, they can prove especially useful in the recycling of paper.

BACKGROUND OF THE INVENTION

By the way of background, for many years wall "loosening enzymes" have been implicated in the control of plant cell enlargement (growth), largely on the basis of rapid biophysical and biochemical changes in the wall during auxin-induced growth (reviewed by Cleland and Rayle, Bot. Mag. Tokyo 1:125–139, 1978; Taiz, Annu. Rev. Plant Physiol., 35:585–657, 1984). Plant walls contain numerous hydrolytic enzymes, which have been viewed as catalysts capable of weakening the wall to permit turgor-driven expansion (reviewed by Fry, Physiol. Plantarum 75:532–536, 1989). In support of this hypothesis, Huber and Nevins (Physiol. Plant. 53: 533–539, 1981) and Inoue and Nevins (Plant Physiol. 96:426–431, 1991) found that antibodies raised against wall proteins could inhibit both auxin-induced growth and wall autolysis of corn coleoptiles. In addition, isolated walls from many species extend irreversibly when placed under tension in acid conditions in a manner consistent with an enzyme-mediated process (Cosgrove D. J. Planta 177:121–130, 1989). Despite these results and other evidence in favor of "wall-loosening" enzymes, a crucial prediction of this hypothesis has never been demonstrated, namely that exogenously added enzymes or enzyme mixtures can induce extension of isolated walls. To the contrary, Ruesink (Planta, 89:95–107, 1969) reported that exogenous wall hydrolytic enzymes could mechanically weaken the wall without stimulating expansion. Similarly, autolysis of walls during fruit ripening does not lead to cell expansion. Thus a major piece of evidence in favor of wall-loosening enzymes as agents of growth control has been lacking.

The walls of growing cucumber seedlings possess extractable proteins which can induce extension of isolated walls. Additionally, we identified two specific wall-associated proteins with this activity. We proposed the name "expansin" for this class of proteins, defined as endogenous cell wall proteins which restore extension activity to inactivated walls held under tension. We further propose the specific names "expansin-29" and "expansin-30" (abbreviated Ex-29 and Ex-30, with respect to their relative molecular masses; McQueen-Mason et al. Plant Cell, 4:1425–1433, 1992) for the two proteins isolated from cucumber. More recently we have identified an oat coleoptile wall protein that induced extension in isolated dicot walls (Z. C. Lee et al., 1993, Planta, 191:349–356). The oat protein has an apparent molecular mass of 29 kD as revealed by SDS-PAGE. For clarity we will refer to the cucumber proteins as cEx, and to the oat proteins oEx. New data demonstrate that an expansin-like protein may be found in proteins obtained from the digestive track of snail and its feces. We will refer to the snail protein as sEx.

During studies of the biochemical mechanism of action of expansins, we found that they had the ability to weaken the hydrogen bonding between plant cell wall polysaccharides (such as cellulose fibers). These findings allow us to propose the following commercial uses of these novel proteins, including paper treatment, agricultural uses, and a variety of use in food and industrial markets.

The paper products industry employs ¾ million workers and is a $60-billion industry in the U.S. alone (plus $40 billion in retail sales). Recycling is a growing concern and will prove more important as the nation's landfill sites become more scarce and more expensive. According to 1992 testimony before congress on the problems and opportunities of paper recycling, the need for improved technology in paper recycling is urgent and of high priority. The use of expansins in this industry may be well received at this time.

Paper derives its mechanical strength from hydrogen bonding between paper fibers, which are composed primarily of cellulose. During paper recycling, the hydrogen bonding between paper fibers is disrupted by chemical and mechanical means prior to reforming new paper products. Expansins may be used to weaken the hydrogen bonding between the paper fibers of recycled paper. As demonstrated in this invention disclosure, expansins, at very low concentrations, in fact weaken commercial papers, including slick paper from magazines and catalogs. These latter types of papers are difficult to recycle because they are not easily disrupted in commercial recycling processes.

The advantages of using expansins for paper recycling include the following: the protein is nontoxic and environmentally innocuous; it could substitute for current harsh chemical treatments which are environmentally noxious. The protein is effective on paper products which are now recalcitrant to current recycling processes. Its use could expand the range of recyclable papers. Because the protein acts at moderate temperature and in mild chemical environments, degradation of paper fibers during recycling should be reduced. This should allow for recycled paper fibers with stronger mechanical properties and with the ability to be recycled more often than is currently practical. Moreover, savings in energy costs associated with heating and beating the paper may be realized.

Other modes of application of expansins includes production of virgin paper. Pulp for virgin paper is made by disrupting the bonding between plant fibers. Following the reasoning listed above, expansins may be useful in the production of paper pulp from plant tissues. Use of expansins could substitute for harsher chemicals now in use and thereby reduce the financial and environmental costs associated with disposing of these harsh chemicals. The use of expansins could also result in higher quality plant fibers because they would be less degraded than fibers currently obtained by harsher treatments.

Cellulose is the major structural component of plant fibers used in textiles, paper and rope making. Commercially, cellulose is used as a starting "feed stock" material for the production of many cellulose derivatives, such as cellulose acetate, cellulose nitrate, and carboxymethyl cellulose. It has numerous uses in many industries, including: as a fiber in the paper/pulp and textile industries, as a starting material for manufacture of films, coatings, membranes, thickeners, and as a biomass source for alcohol production. Processing cellulose for these commercial applications is arduous because cellulose is arranged in a microcrystalline lattice structure and incorporated into microfibrils that are mechanically and chemically resistant to chemical, enzymatic and biological degradation.

Native cellulose is found as an ordered microfibril, in which individual glucans laterally associate with one another into tight arrays, or long crystalline ribbons. This arrangement limits access of enzymes or chemicals to the individual glucans. Glucan accessibility is thus one of the major limitations to efficient enzymatic or chemical modification of cellulose.

In order to make the glucans accessible to standard enzymatic or chemical processing, the individual glucans need to be stripped off the surface of the crystalline microfibrils (Bayer, Chanzy, Lamed, and Shoham, 1998). The chemical processes for solubilizing and degrading cellulose for commercial applications generally involve the use of harsh chemicals and extreme conditions. These processes often result in unwanted modification and derivatization of the cellulose. Numerous cellulases are commercially available, however they lack effectiveness because the enzymes cannot gain ready access to the crystalline polymer.

If a means could be found to break open, decrystallize, or by another enzymatic mediated process to modify cellulose under milder conditions, this might have considerable practical benefit to industries that process cellulose or manufacture products utilizing cellulose.

SUMMARY OF THE INVENTION

In accordance with the present invention, a new class of proteins and methods related thereto are presented. The proteins which can be characterized as catalysts of the extension of plant cell walls and the weakening of the hydrogen bonds in the pure cellulose paper are referred to as expansins. In general, the present invention is a composition comprising an isolated, purified and salt-soluble polypeptide in an acid medium, where in the polypeptide has an amino acid sequence with a molecular weight of about 29–30 kD as measure by SDS-PAGE, and induces expansin of inert plant wall material. Preferably the pH of the acid medium is in the range of 3.5–5.5 and additionally may comprise a sulfhydryl reducing agent. The pH range is more preferably about 4–5 and most preferably is about 4.5.

In another aspect the present invention provides a composition for the enhancement of the enzymatic degradation of cellulose. The composition comprises an expansin and an enzyme having the property of degrading cellulose. In one embodiment, the enzyme is a hydrolytic enzyme. In a preferred embodiment, the enzyme is a cellulase. The cellulase may be derived from a variety of sources, including microorganisms such as Trichoderma.

The present invention further comprises a method for enhancing the accessibility of cellulose to chemical or biological modification. The method comprises incubating a sample containing cellulose with an expansin. This method further comprises incubating the sample with a chemical or biological modifying agent. In one embodiment, the modifying agent comprises an enzyme having the property of degrading cellulose. In a preferred embodiment, the method comprises incubating the sample with a hydrolytic enzyme, such as cellulase.

The present invention also provides a method for enhancing enzymatic degradation of cellulose. The method of the invention comprises incubating a sample containing cellulose with an expansin and an enzyme having the property of degrading cellulose. In one embodiment of the method the enzyme is a hydrolytic enzyme. In a preferred embodiment of the method, the enzyme is a cellulase. The cellulase may be derived from a variety of sources, including Trichoderma.spp, Aspergillus spp, Humicol spp and other fungi or bacteria. With respect to the amounts of cellulose and expansin present in the reaction mixture, in one embodiment the expansin is present in an amount of at least about 0.0001 to about 0.005 times, the amount of cellulose present in the reaction mixture. In a preferred embodiment, the expansin is present in an amount of at least about 0.001 times the amount of cellulose present in the reaction mixture. With respect to the amounts of expansin and cellulase utilized in the method of the present invention, in one embodiment the expansin is present in an amount of at least about 0.01 to 0.5 times the amount of cellulase present. In a preferred embodiment, the expansin is present in an amount of at least about 0.1 times the amount of cellulase present.

The novel method has commercial utility in various applications in that cellulose found in but not limited to sources such as textiles, paper and rope can be successfully treated using the method of the invention.

Two proteins have been isolated by fractionation techniques from washed wall fragments of the cucumber hypocotyls, referred to as "cucumber expansin-29" and "cucumber expansin-30" (abbreviated cEx-29 and cEx-30, with respect to their relative masses). Another expansin protein has been isolated from oat coleoptiles (oat expansin oEx-29). Expansins appear to be broadly distributed throughout the plant kingdom and have been identified in stem and leaf vegetables (i.e., broccoli, cabbage), fruit, and seed vegetables (i.e., tomato). fiber crops and cereals (i.e., corn), and forest and ornamental crops (i.e., cotton). Also, expansin-like protein have been found in the proteins obtained from the digestive track of snail and its feces (sEx). These novel proteins can find use in a variety of applications including the paper industry in production of paper pulp in preparation of virgin paper and in paper recycling as a preferred way of disruption of paper fibers due to their nontoxicity and environmental innocuosity in contrast with the harsh chemical treatments applied today, which are environmentally noxious.

OBJECTS OF THE INVENTION

An object of this invention is to provide novel extractable proteins which can induce extension of isolated walls and can weaken commercial paper products.

Another object of this invention is to provide a method of isolation of the said proteins from various sources including growing plant tissue.

It is also an object of this invention to develop methods of using the said proteins. These and other objects and advantages of the invention over the prior art and a better understanding of its use will become readily apparent from the following description and are particularly delineated in the appended claims.

Ten-mm sections of tissue were frozen and thawed, and lightly abraded prior to suspension in the extensometer. Tissues were clamped under an applied force of 20 g and extension recorded using a linear voltage displacement transducer. The length of tissue between the clamps was 5 mm.

(A) Extension curves of native and reconstituted cucumber hypocotyl walls. From top to bottom: native walls were suspended under tension in 50 mM Hepes, pH 6.8, for 20 min. after which the bathing solution was replaced by 50 mM sodium acetate, pH 4.5, (arrow). Inactivated walls were treated for 15 sec with boiling water prior to suspension; as shown in the second line, this treatment eliminated acid induced extension. For reconstitution experiments, inactivated walls were suspended in 50 mM sodium acetate, pH 4.5, for 30 min. at which point the bathing solution was replaced by 0.5 mL of fresh solution (arrows) containing 2–3 mg of proteins extracted from growing cell walls (apical wall protein), or with soluble proteins from growing cells (apical soluble proteins), or proteins extracted from cell walls from the nongrowing cotyledon (cotyl. wall protein) or from walls of the basal hypocotyl (basal wall protein).

(B) Reconstitution of extension activity in inactivated (heat treated) walls from growing tissues of different species by the active cucumber wall extract. Walls from the growing region from tomato, pea and radish hypocotyls, lily and onion leaves, and coleoptiles of maize and barley were prepared, heat-treated, and suspended as given above, except that a force of only 10 g was applied to the more fragile tomato and radish walls. Walls were first suspended in 50 mM sodium acetate, pH 4.5, after 30 min. (arrow) the bathing solution was replaced with 0.5 mL of the same buffer containing 2–3 mg of active wall protein from cucumber hypocotyls (apical 3 cm).

Figure 2A:
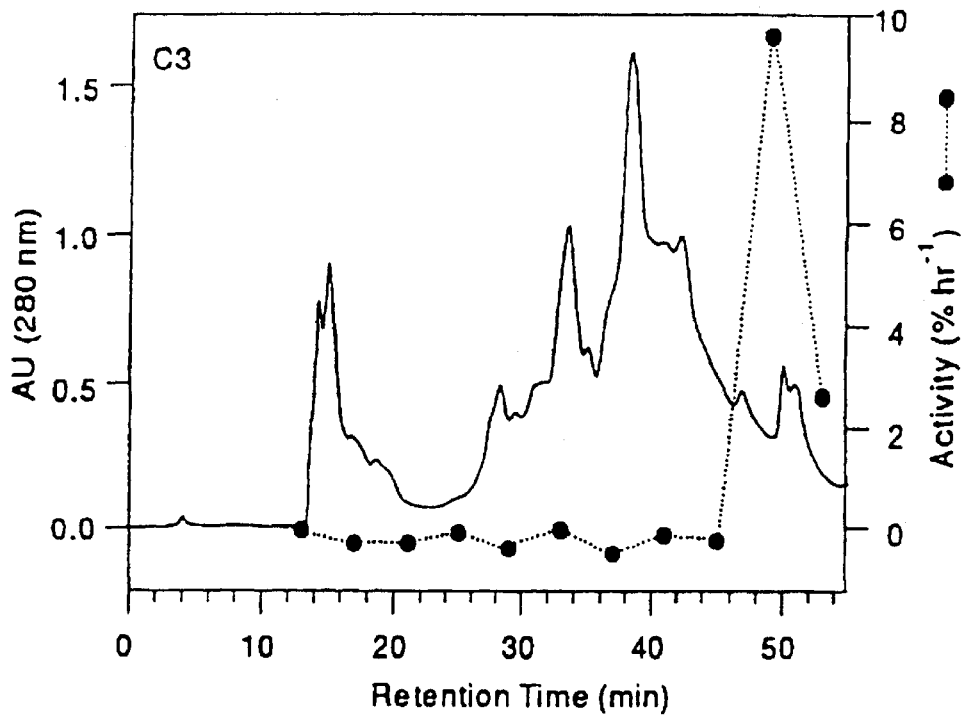
Figure 2B:
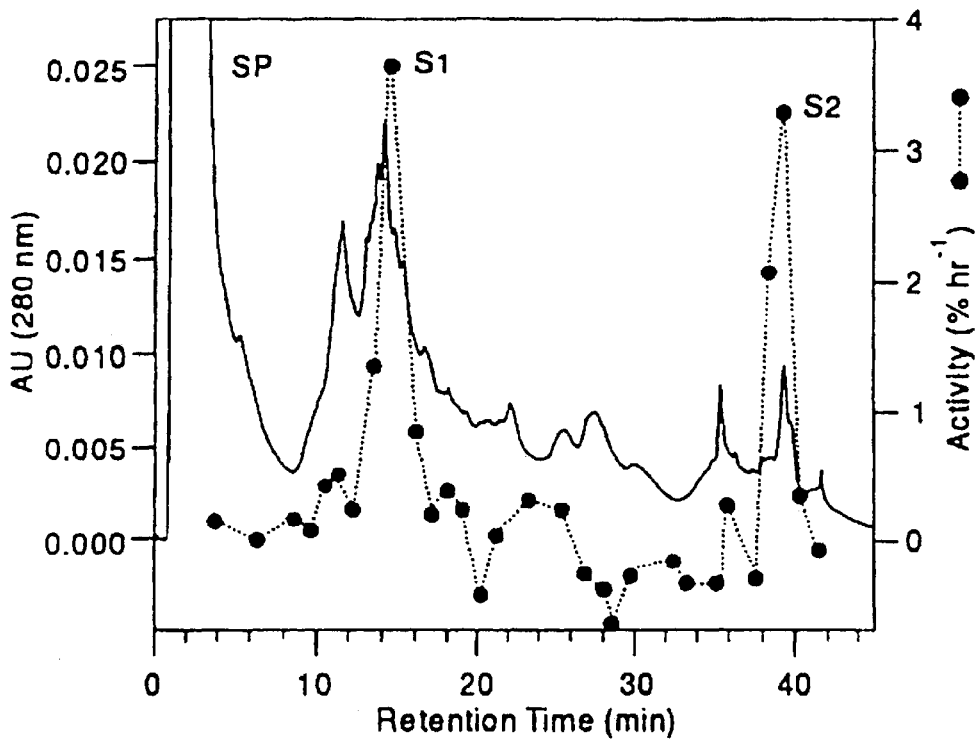

FIG. 2. Fractionation of extension-inducing cucumber wall extracts by HPLC.

(A) Ammonium sulfate precipitates of salt extracted cucumber wall extracts were resuspended and loaded onto a C3 hydrophobic interactions column in 50 mM sodium acetate, pH 4.5, 20% (saturation) ammonium sulfate. Proteins were eluted in a descending gradient (20–0%) of ammonium sulfate. Fractions were desalted and checked for extension inducing activity with inactivated cucumber tissues as in FIG. 1. $A_{280}$ nm is shown by a solid line and extension inducing activity by a broken line.

(B) Active fractions from (A) were concentrated and desalted into 15 mM Mes, pH 6.5, and loaded onto a sulfopropyl anion exchange column equilibrated with the same buffer. Proteins were eluted with an ascending gradient of NaCl (0–1M) in this buffer. Extension inducing activity (broken line) of fractions was checked directly after adjusting the pH to 4.5 with 1 M acetic acid.

Figure 3:
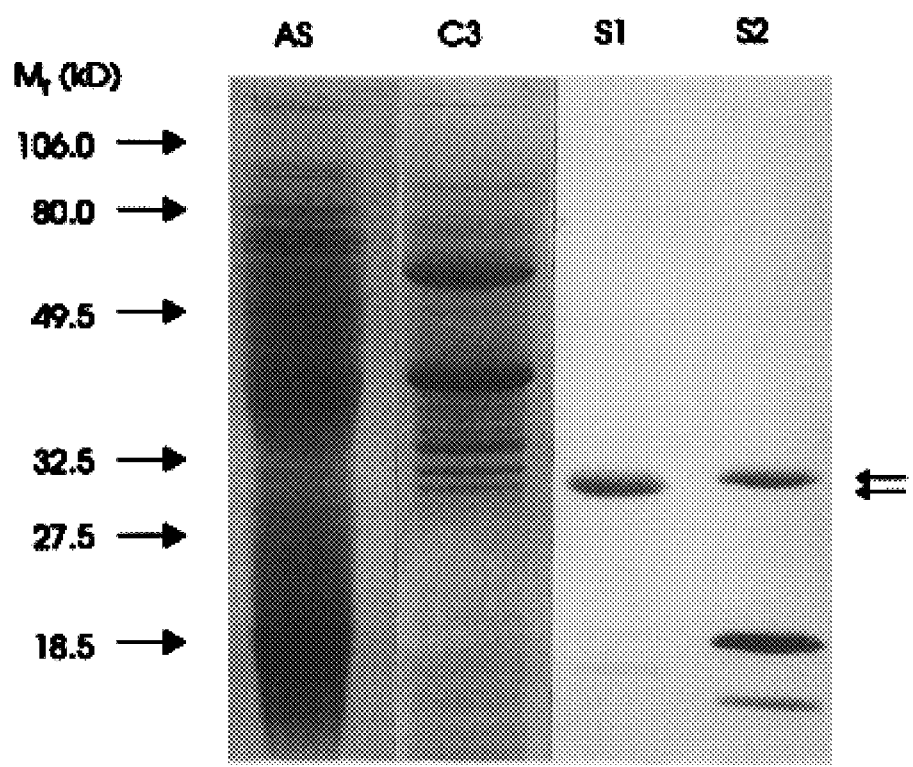

FIG. 3. SDS-PAGE of ammonium sulfate precipitate (AS), and active fractions from C3 and sulfopropyl (S1 and S2) HPLC separations of cucumber proteins.

Protein samples were concentrated, desalted, and run on SDS-polyacrylamide gels according to the method of Laemmli. Gels were stained with Coomassie Brilliant Blue R 250. Arrows indicate the major protein bands at 29 and 30 kD in the S1 and S2 fractions which appear to possess the extension-inducing activity.

FIG. 4. The effects of DTT, metal ions, methanol and water boiling, and protease treatments on reconstituted extension.

(A) The effect of DTT on reconstituted extension. Growing wall specimens of cucumber hypocotyl were inactivated by heat and then reconstituted by shaking in a solution of active C3 proteins (estimated concentration of 50 micrograms per mL). Walls were then clamped under constant load (as described in FIG. 1) firstly in a bathing solution of 50 mM Hepes, pH 6.8. After 20 min. the solution was changed for 50 mM sodium acetate, pH 4.5 (first arrow).

After a further 40 min. DTT (from a 100 mM stock solution) was added to give a final concentration of 10 mM. The first two lines represent typical traces from 4 experiments with and without DTT addition.

For the effects of metal ions, growing wall specimens from cucumber hypocotyl were inactivated by heat and then clamped under constant load (as described in FIG. 1) in a bathing solution of 50 mM sodium acetate, pH 4.5. After 20 min. the bathing solution was exchanged for a fresh one containing 50 micrograms per mL of active C3 proteins (first arrow). After a further 40 min. $AlCl_3.6H_2O$ or $CuCl_2.2H_2O$ (from 100 mM stock solutions) was added to bring the bathing solution to a final concentration of 1 mM (second arrow). All experiments were repeated 4 times. Line 3 shows extension without the addition of metal ions, the next two lines show typical data obtained with the addition of $AlCl_3$ and $CuCl_2$ respectively.

For the effects of boiling cell walls in methanol or boiling in water on the recovery of extension inducing activity, growing cucumber hypocotyl tissue was first boiled for 3 min. in methanol or for 30 sec in distilled water, wall fragments were recovered, cleaned and extracted (as described in FIG. 1). Proteins were precipitated with $(NH_4)_2SO_4$ and resuspended in 50 mM sodium acetate, pH 4.5 before being tested in the reconstitution assay described in FIG. 1. Lines 6 and 7 are representative data from 4 experiments.

(B) Growing wall specimens were inactivated by heat and reconstituted with C3 proteins. Reconstituted walls were incubated with 1000 units of trypsin or chymotrypsin for 4 hr at 30° C., in 50 mM Hepes, pH 7.3, or with 2 milligrams per mL of pronase or papain for 4 hr at 30° C., in 50 mM sodium acetate, pH 5.0. Controls were reconstituted and incubated in the same manner without the addition of proteases. At the end of the incubations tissues were clamped under constant load (as described in FIG. 1), first in 50 mM Hepes, pH 6.8. After 30 min. the bathing solution was replaced by 50 mM sodium acetate, pH 4.5. The difference in the two rates of extension was calculated. Data presented are the means of four experiments in each case.

Figure 5:
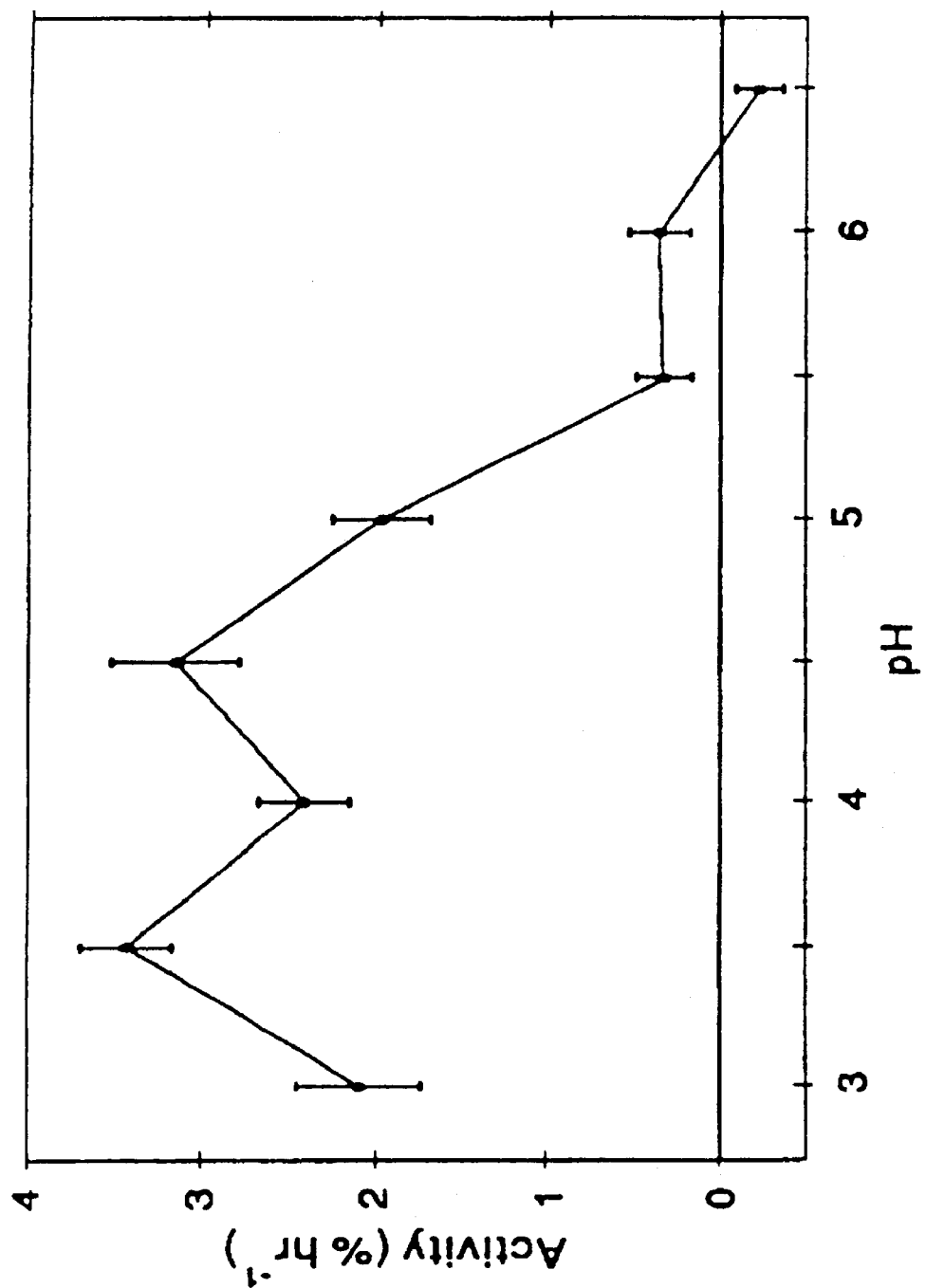

FIG. 5. Effect of pH on reconstituted extension.

Cucumber wall specimens, inactivated by heat, were clamped under constant load (as described in FIG. 1). Initial bathing solutions were 50 mM citric acid, titrated to pH 3.0, 3.5, 4.0, 4.5, 5.0, 5.5, 6.0 or 6.5 with 1 M $K_2HPO_4$. After 30 min. the bathing solution was changed for a 1:1 dilution of active C3 proteins with the relevant buffer (final estimated protein concentration was 50 micrograms per mL), where necessary the final pH was adjusted using either 1 M citric acid or 1 M $K_2HPO_4$. Extension was recorded for a further 2 hr and change in rate of extension calculated as initial-final rates.

Figure 6A:
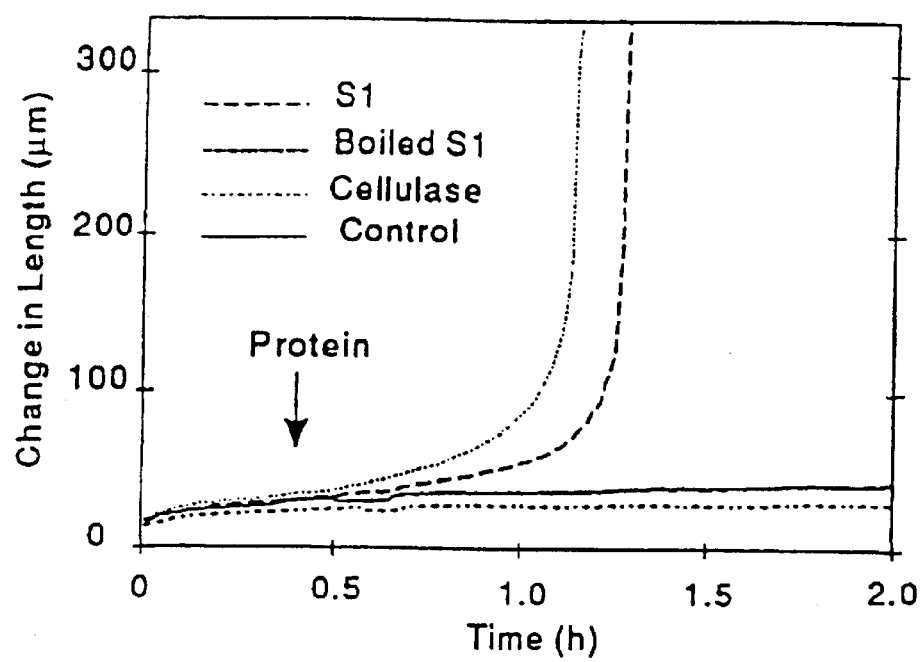
Figure 6B:
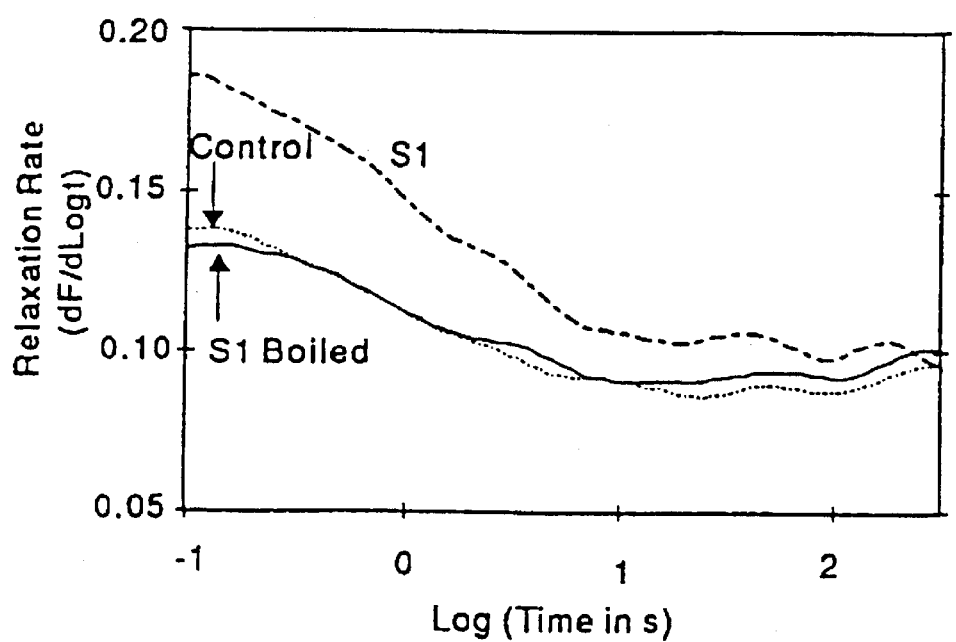
Figure 6C:
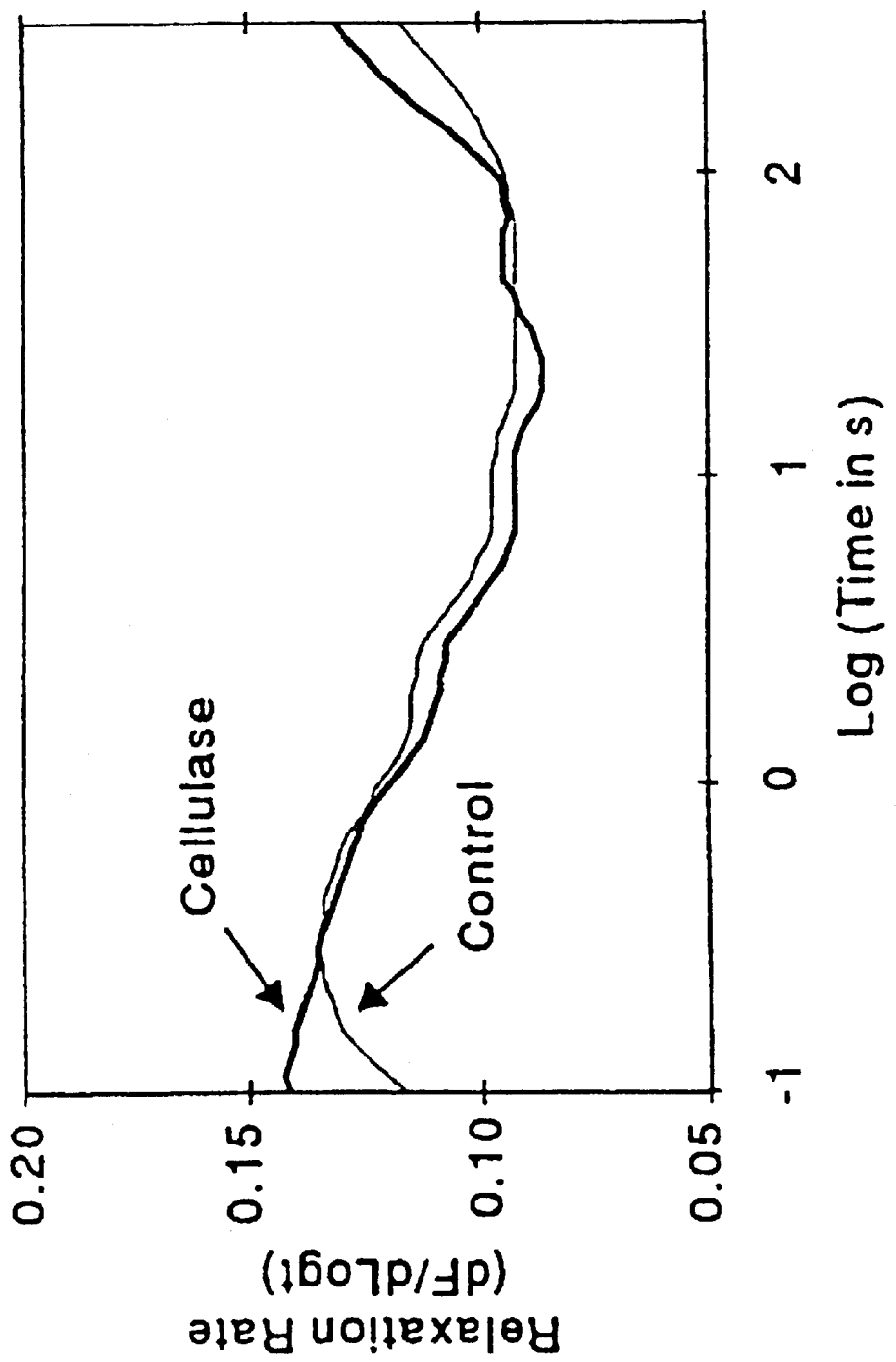

FIG. 6. The effects of cucumber expansins on cellulose paper.

(A) Strips of Whatman No. 3 filter paper were clamped in a constant load extensometer with 5 mm of paper between the clamps (described in FIG. 1). Paper strips were initially bathed in 50 mM sodium acetate, pH 4.5. After about 20 min. of extension, the bathing solution was replaced with either: 5 mg of S1 protein in 15 mM Mes, pH adjusted to 4.5 with 1 M acetic acid (S1); 5 mg of S1 protein, in the same buffer, which had been heated to 100° C. for two minutes (Boiled S1); 100 mg of cellulase (from *Trichoderma viride* Boehringer Mannheim) in 50 mM sodium acetate (Cellulase), pH 4.5; or 50 mM sodium acetate pH 4.5 (Control). Extensions were recorded for a further 100 min.

The figure shows representative traces from at least six independent experiments, all of which showed similar results.

(B) Strips of Whatman No. 3 paper were soaked in a solution containing 5 mg/mL S1 protein in 15 mM Mes, pH adjusted to 4.5 with 1 M acetic acid, (S1); in the same protein solution which had been boiled for two minutes (Boiled S1); or in 50 mM sodium acetate, pH 4.5 (Control). Stress relaxation tests were performed by standard methods. Data represent the average of ten measurements in each case. Experiments were repeated three times with similar results.

(C) Conditions were the same as in (B) except that the paper strips were soaked in a solution containing 100 mg/mL of Trichoderma cellulase in 50 mM sodium acetate, pH 4.5 (Cellulase), or 50 mM sodium acetate, pH 4.5 (Control). Data are the averages of ten measurements in both cases. Experiments were repeated three times with similar results.

Figure 7:
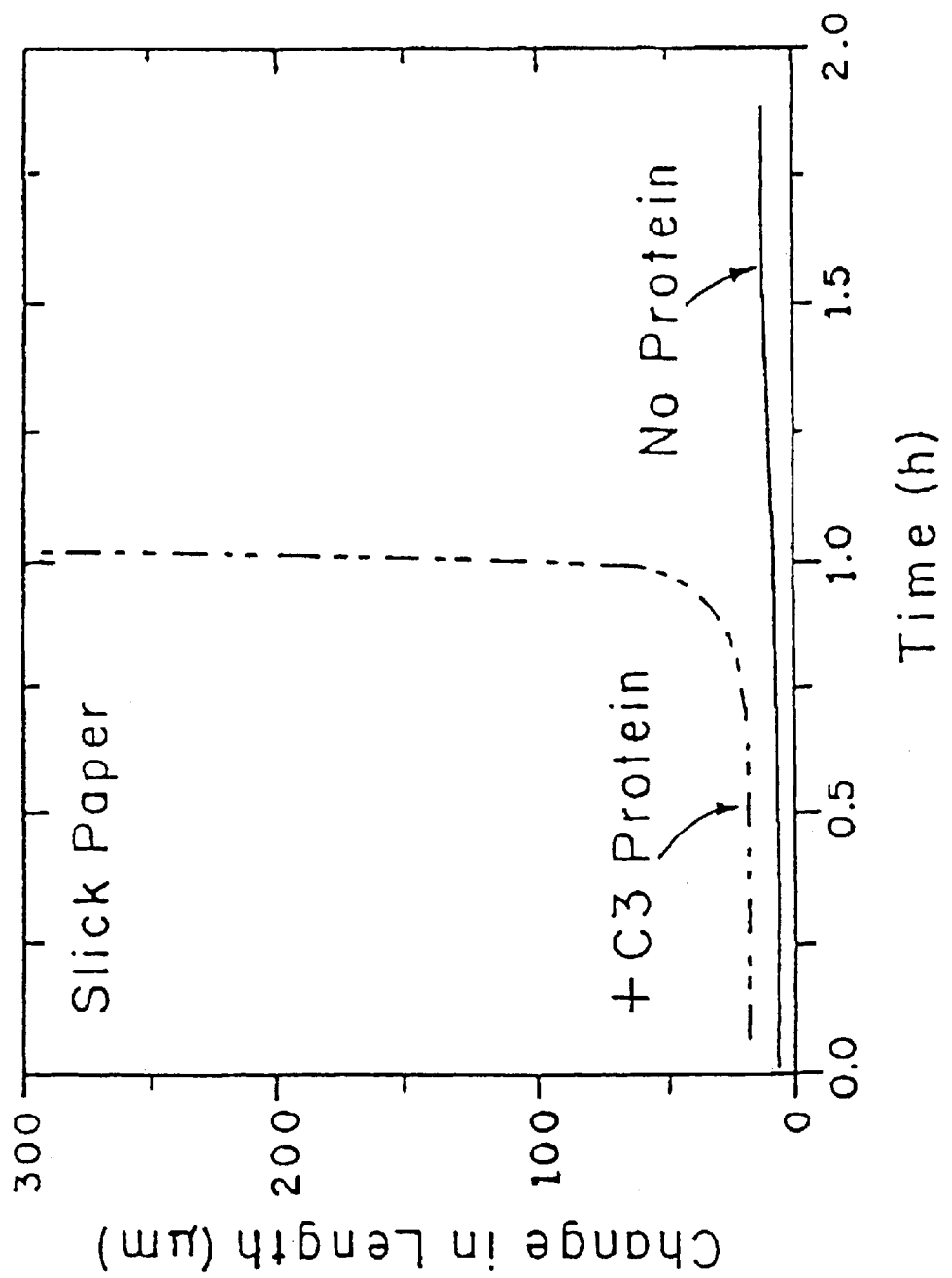

FIG. 7 The effect of cucumber expansins on slick paper.

Paper strips of 2–3 mm width were cut and hung in our extensometer, such that a 5-mm long strip was put under 20-g force. The buffer contained 50 mM sodium acetate, pH 4.5 with or without added C3 protein (about 20 μg per paper strip was used). The length of the paper strips was recorded for up to 5 h. Four samples of each paper were used with each treatment (+/−protein). The untreated (control) paper showed very little change in length, and maintained its mechanical strength throughout the test period. In contrast, the treated papers began to extend and quickly broke once extension began. The time for breakage after addition of protein varied from 45 min. to 2.5 h, but all samples broke.

FIG. 8. Acid-induced extension in native and heat-treated oat coleoptile walls.

(A) When switched from a neutral buffer (50 mM Hepes, pH 6.8) to an acidic buffer (50 mM sodium acetate, pH 4.5), native walls extended at a high rate which fell continuously with time, whereas heat-treated walls lacked a significant response. The native and heat-treated (15 sec in boiling water) walls were prepared and mounted on an extensometer (5 mm between two clamps) with 20 g of tension as described by Cosgrove (1989) and McQueen-Mason et al. (1992).

(B) A plot of extension rate for the native walls shown in A demonstrates that the rate decreases continuously. Similar results were obtained in 10 repetitions.

Figure 9A:
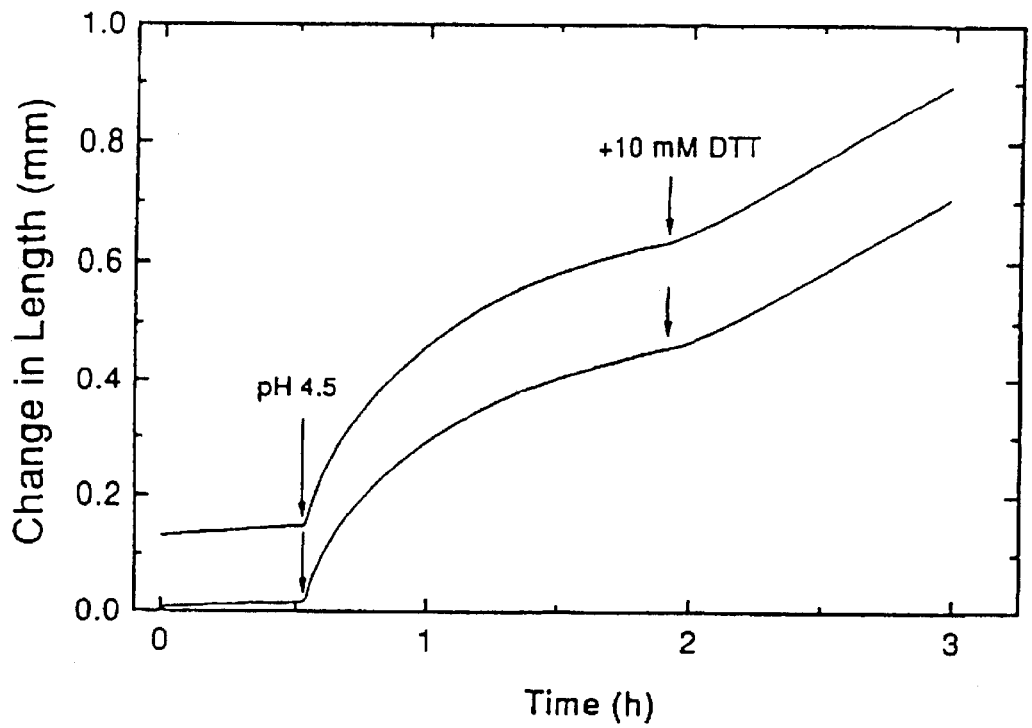
Figure 9B:
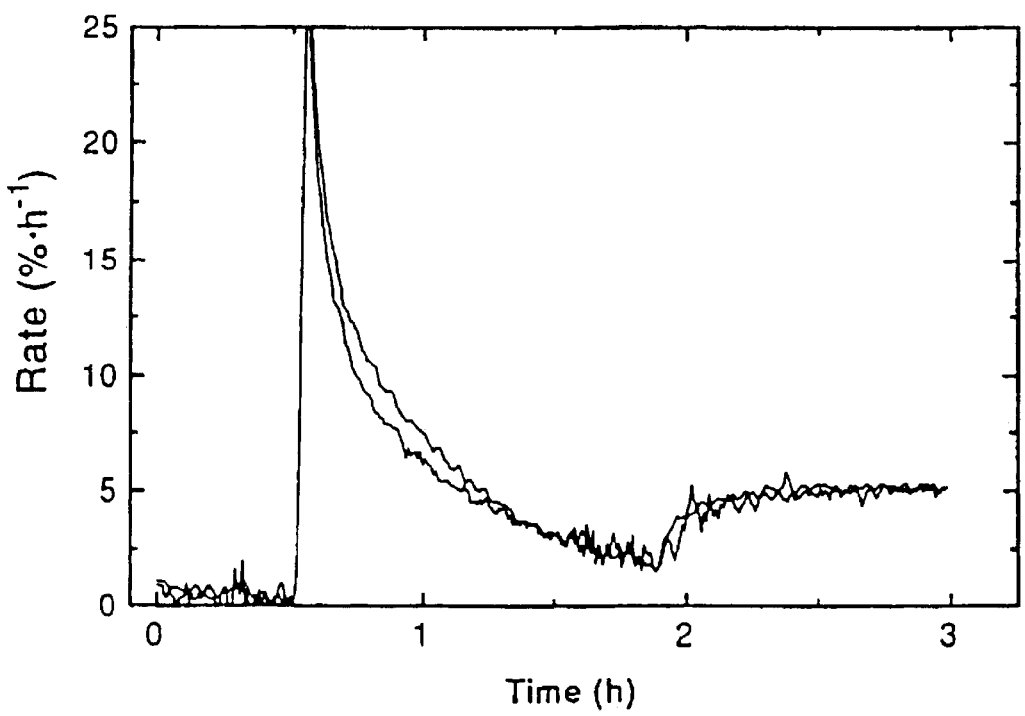

FIG. 9. Effect of dithiothreitol (DTT) addition to acid-induced extension of oat coleoptile walls.

Native walls were prepared as in FIG. 8 and the buffer was exchanged for the same buffer containing 10 mM DTT at approximately 80 min after start of acid-induced extension (A) The plot of extension rate (B) shows that the rate is stable at about 5% per h after addition of DTT. Similar results were obtained in 6 independent trials.

Figure 10A:
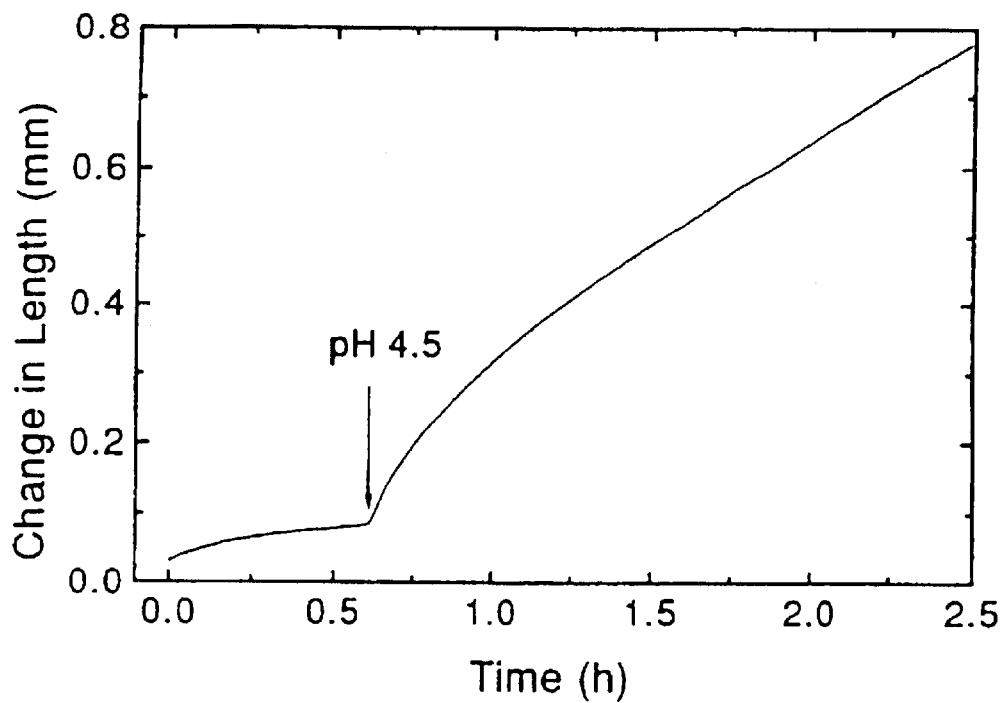
Figure 10B:
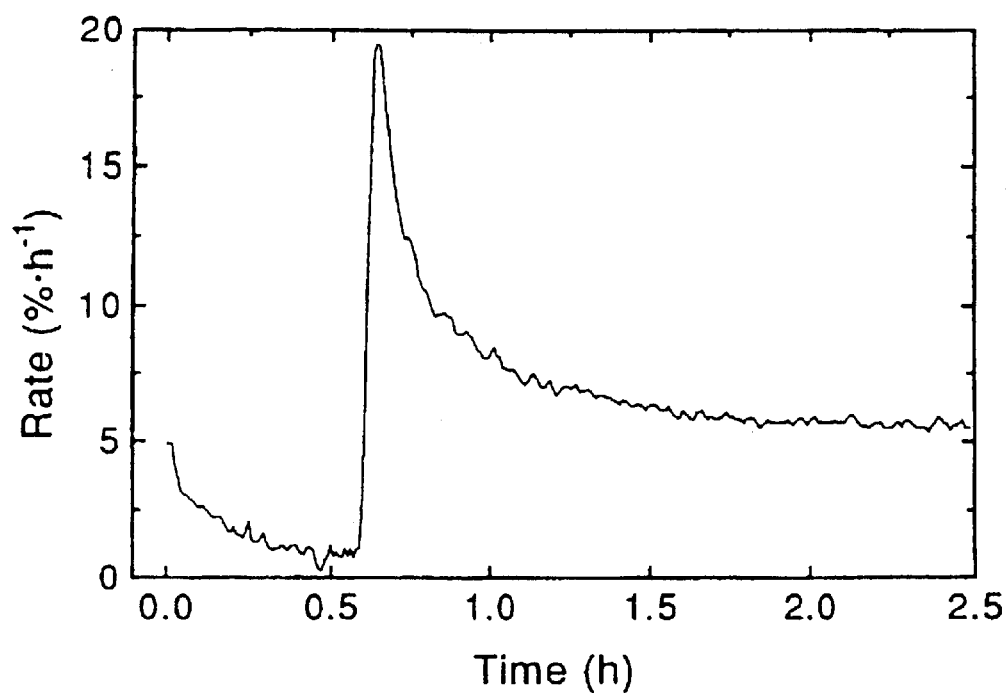

FIG. 10. Acid-induced extension in native oat coleoptile walls in the continuous presence of DTT.

(A) Walls were prepared as in FIG. 8 and incubated in 50 mM Hepes, pH 6.8, with 2 mM DTT; after about 35 min the buffer was switched to 50 mM sodium acetate, pH 4.5, with 2 mM DTT.

(B) The plot of extension rate shows that the decay in extension rate after 1 h is greatly diminished (compare with FIG. 8). This experiment was repeated four times with similar results.

FIG. 11. Extension induced in oat, cucumber and pea walls by proteins extracted from oat coleoptiles walls (A) and cucumber walls (B).

Coleoptile wall proteins and cucumber wall proteins were extracted with 1 M NaCl, precipitated with ammonium sulfate, desalted and partially purified on a DEAE Sephadex column. Heat-inactivated cell walls from oat coleoptiles, cucumber hypocotyls or pea epicotyls were clamped at 20-g tension in 50 mM sodium acetate, pH 4.5. After about 0.5 h, the solution was replaced with 0.4 mL of the same buffer containing about 10 mg proteins partially purified from oat or cucumber cell walls by DEAE-anion exchange chromatography. The data represent a typical experiment from at least four replicates.

Figure 12A:
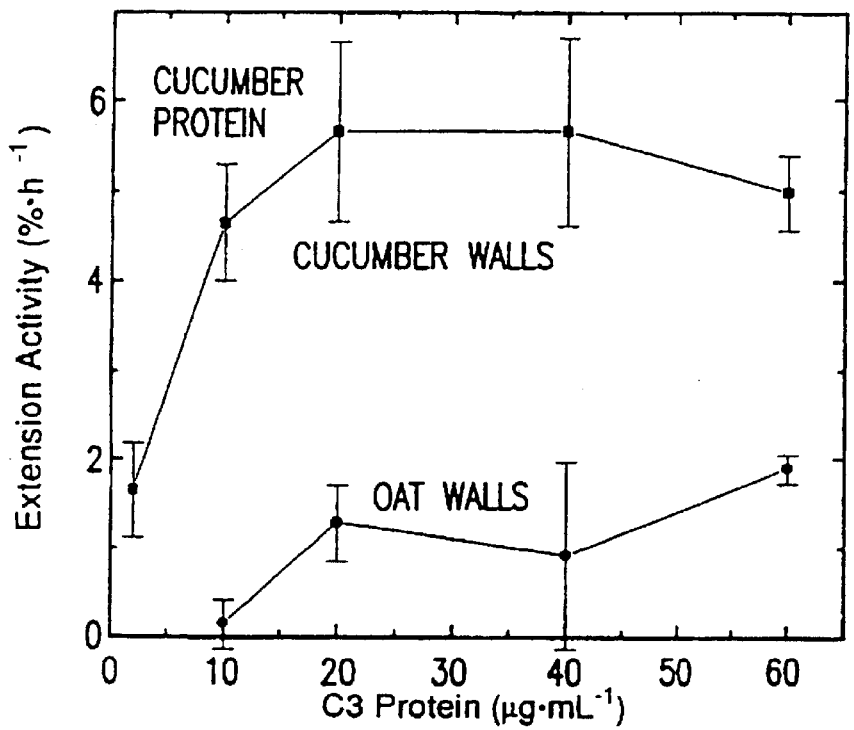

FIG. 12. Comparative responsiveness of oat and cucumber walls to exogenously added oat or cucumber proteins.

(A) Concentration dependence of cucumber and oat walls to exogenous cucumber protein. Cucumber walls were frozen, thawed, abraded, heat-inactivated and loaded in the extensometer, as in FIG. 8. Oat coleoptiles were treated similarly, except that the epidermis was stripped with fine forceps and the coleoptile bisected longitudinally prior to freezing. The walls extended for approximately 30 min in 50 mM sodium acetate, pH 4.5, before the buffer was exchanged for the same one containing various concentrations of partially purified cucumber expansins (the active fraction from the C3 HPLC separation) . Extension activity is calculated as the increase in extension rate in the first 15–20 min after addition of C3 protein and is expressed as % increase in length per h). The average extension rate prior to addition of protein in these experiments was 2% per h for oat walls and 1.7% per h for cucumber walls.

(B) Response of oat and cucumber walls to added oat protein. Heat-inactivated oat and cucumber walls were prepared as in (A) and extended in sodium acetate, pH 4.5, for about 30 min prior to exchange of buffer for the same one containing 73 g of crude oat coleoptile protein (ammonium sulfate precipitate) per sample holder (about 400 L). The extension curves shown illustrate two examples with responses close to the mean (2.8% $h^{-1}$ increase for the cucumber wall and 1.1% $h^{-1}$ increase for the oat wall). The mean responses (n=4) of oat and cucumber walls to added oat protein are shown in the inset and are calculated as the increase in extension rate, expressed as % per h. The baseline extension rates prior to addition of protein averaged 2.4% per h (oats) and 1.1% per h (cucumber).

Figure 13:
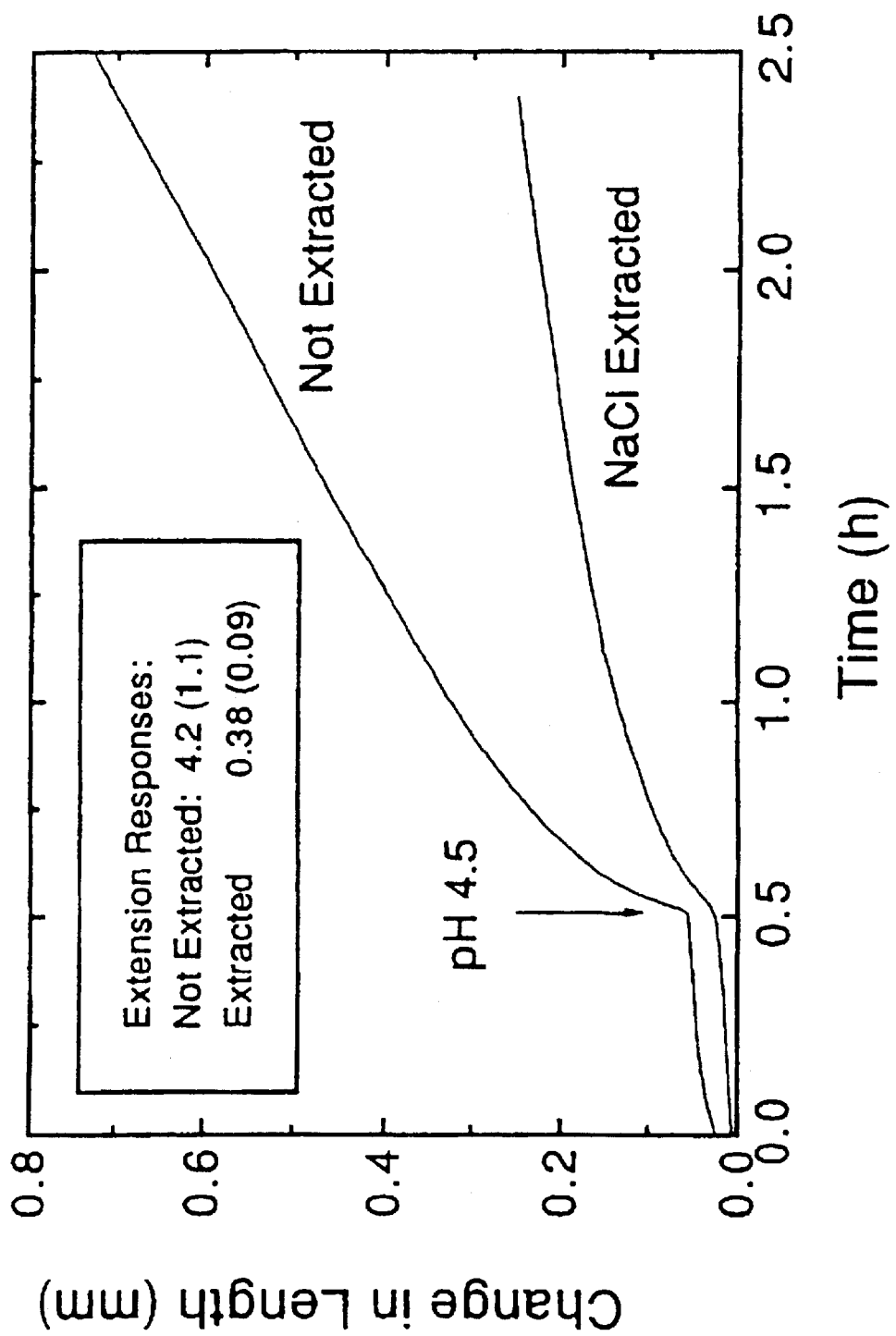

FIG. 13. Effect of 1 M NaCl extraction on acid-induced extension of oat coleoptile walls.

Coleoptiles were abraded prior to freezing, then either directly clamped in the extensometer or extracted for 16 h in 1 M NaCl containing 10 mM Hepes, pH 6.8, 3 mM EDTA and 2 mM sodium bisulfite prior to measurement. Walls were rinsed briefly in water, clamped at 20 g tension, then incubated in 50 mM Hepes, pH 6.8, with 2 mM DTT. At about 30 min the buffer was exchanged for 50 mM sodium acetate, pH 4.5, with 2 mM DTT. The curves shown are representative of eight trials for each treatment. The inset shows the average extension response (SE, n=8) of each treatment. Response is calculated as the rate at 1.5 to 2 h minus the rate prior to pH 4.5 buffer, and is expressed as % increase in length per h.

Figure 14:
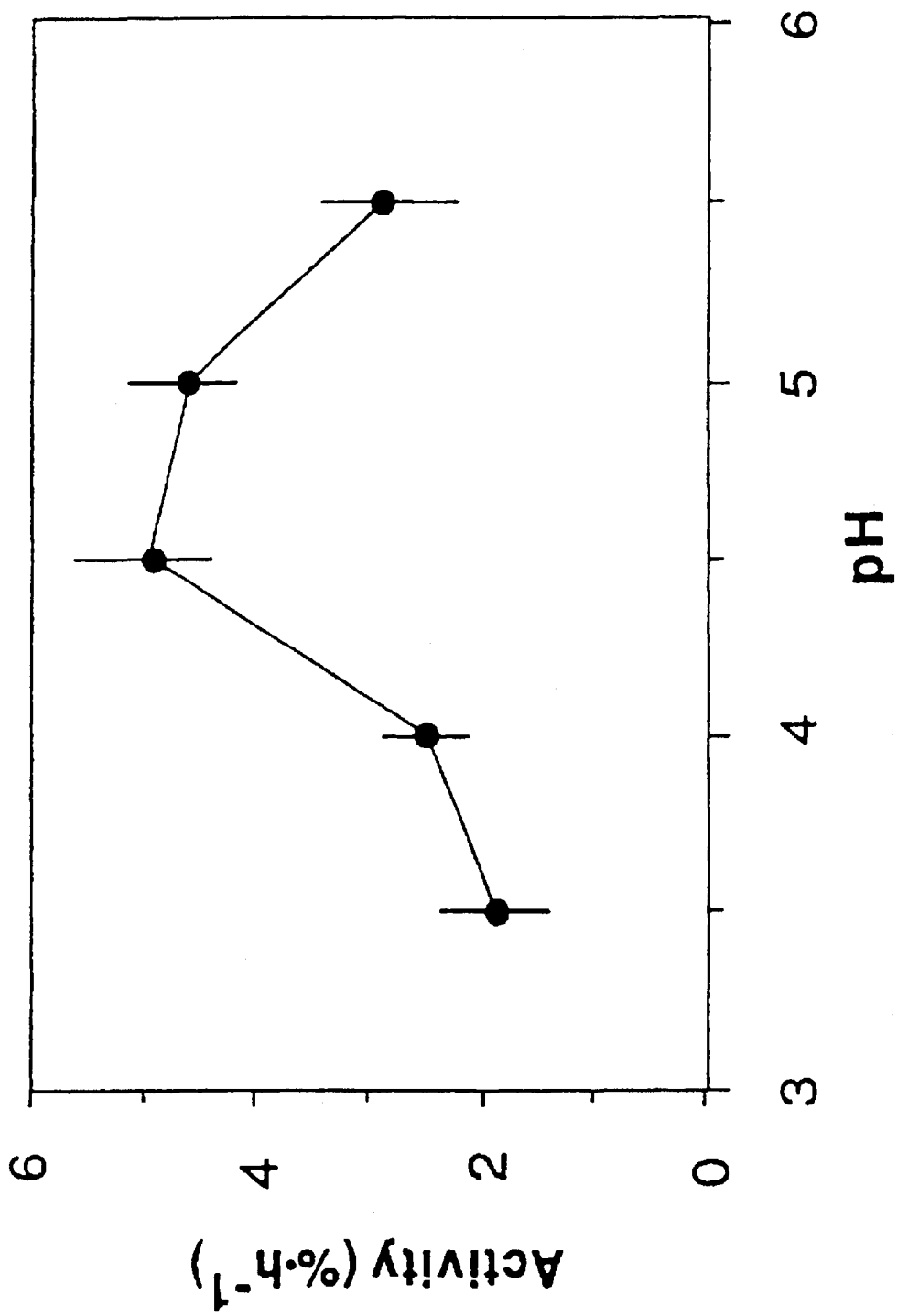

FIG. 14. pH dependence of the extension activity reconstituted by oat wall proteins.

Heat-inactivated walls from cucumber hypocotyls were clamped in an extensometer as in FIG. 8 and placed in 50 mM sodium acetate buffers at pH 3.5, 4.0, 4.5, 5.0 or 5.5. After 20 min, the solutions were replaced with 0.4 mL of the corresponding buffer containing 10 mg oat-coleoptile wall proteins partially purified by DEAE-chromatography. The extension activity was calculated by subtracting the baseline rate without proteins from the linear rate (5–30 min) after the addition of the proteins, and expressed as % increase in length per h above the baseline rate. The data represent the means±S.E. (n=5 to 8). The average baseline rate prior to addition of protein ranged between 2.52 and 2.96 m min$^{-1}$ (or 3.0 to 3.55% per h) for all pH groups.

Figure 15A:
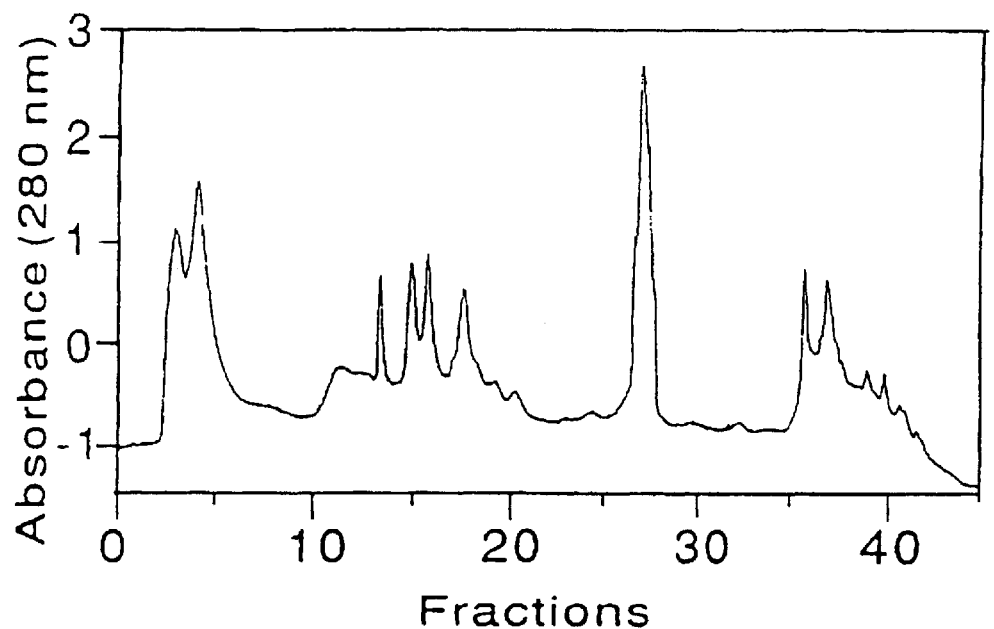
Figure 15B:
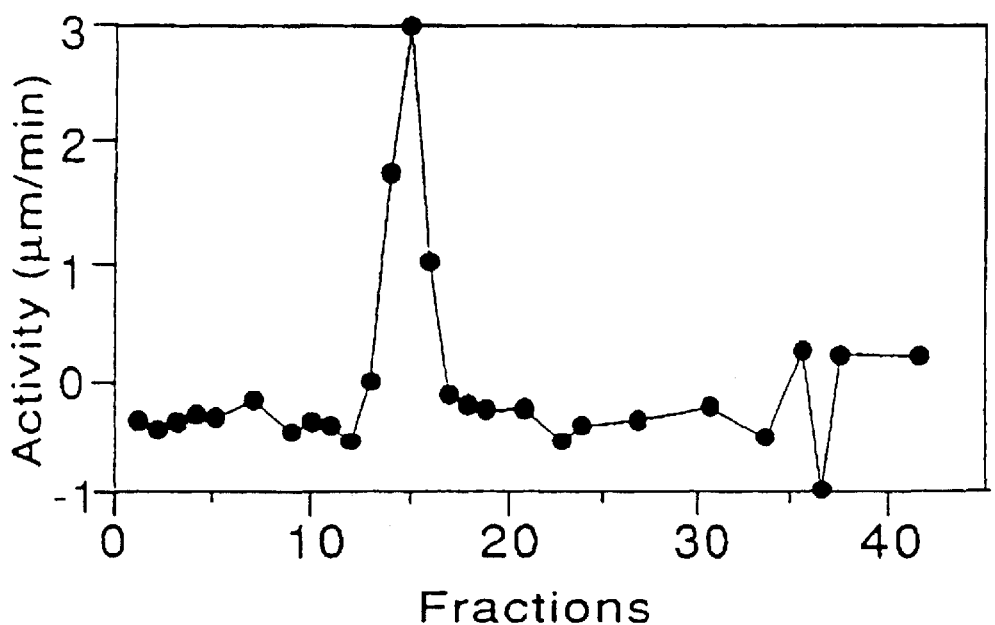

FIG. 15. Purification of oat expansin by high pressure liquid chromatography (HPLC) on a carboxymethyl (CM) cation exchange column.

(A) Elution of proteins (absorbance at 280 nm) from a CM-column. Proteins were solubilized from the cell walls of etiolated coleoptiles by 1 M NaCl and then sequentially fractionated by ammonium sulfate precipitation, DEAE-chromatography, and ConA chromatography, prior to CM-HPLC.

(B) Wall extension activity of HPLC fractions. The extension activity was assayed by addition of fraction samples (equal volumes, typically 20 L) to sample cuvettes containing 400 L of 50 mM sodium acetate buffer, pH 4.5. Activity is expressed as increase in extension rate after addition of protein to a 5-mm, heat-inactivated, abraded oat coleoptile. A single peak of activity eluted at about 15 min or 3.5% of 1 M NaCl. Similar results were obtained in six independent trials.

Figure 16:
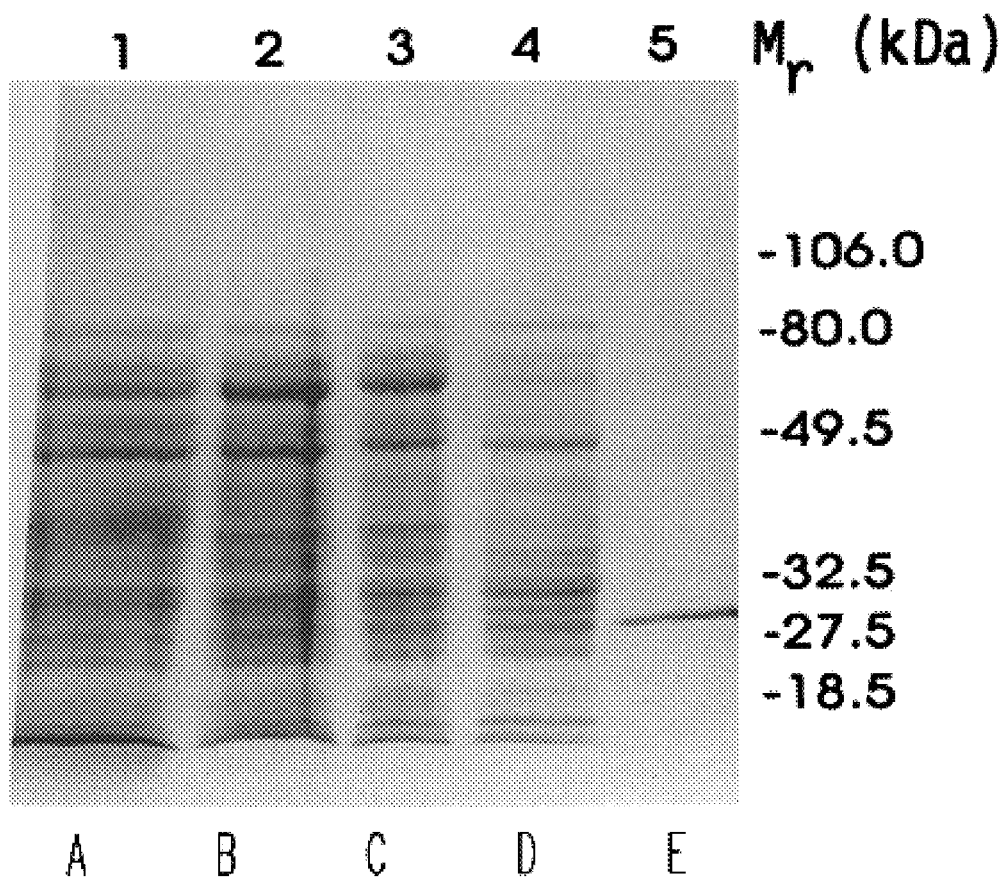

FIG. 16. SDS-polyacrylamide gel electrophoresis (SDS-PAGE) of proteins from different purification steps.

Active protein fractions were separated on a SDS-PAGE gradient gel (4–20%) and stained with Coomassie Blue R-250. Lane 1, 1 M NaCl extraction (20 mg); lane 2, ammonium sulfate precipitate (20 mg); lane 3, active DEAE-fraction (10 mg); lane 4, proteins passing through Con A column (5 mg); lane 5, active fraction from CM-HPLC (0.3 mg). The protein with apparent molecular mass of about 29 kD was designated as oat expansin (oat Ex29). Similar results were obtained in five trials, except in some of these an additional protein band at about 35 kD appeared in lane 5.

Figure 17:
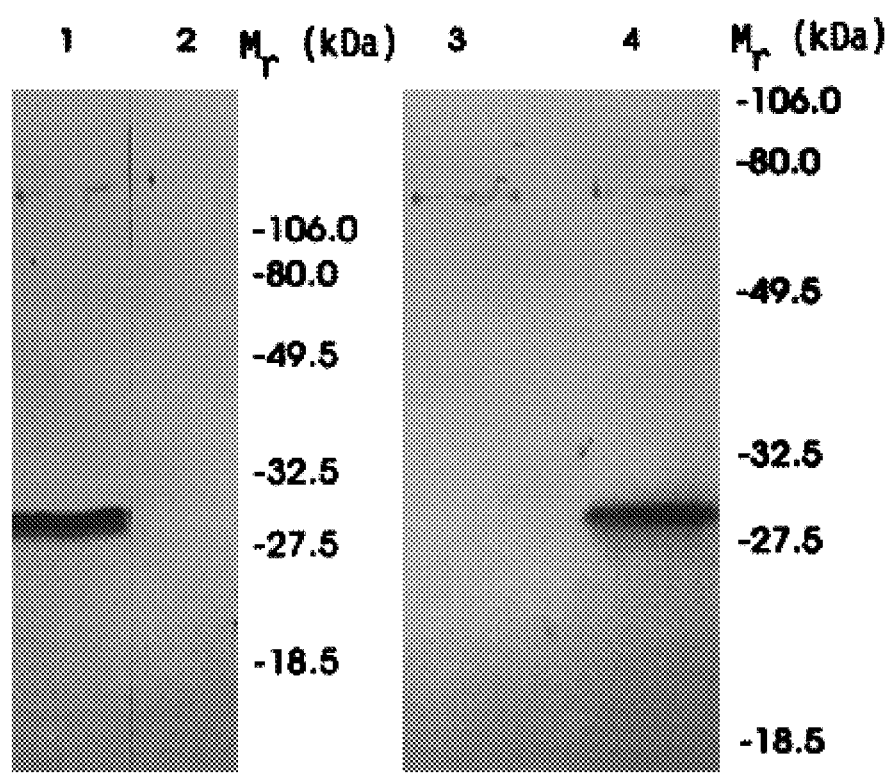

FIG. 17. Western analysis of oat coleoptile proteins probed with antiserum against cucumber Ex29.

Comparison of lane 1 (crude wall protein) with lane 2 (crude protoplasmic protein) shows that the antiserum recognizes an Ex29-like protein (arrow) specifically bound to the coleoptile cell wall. Comparison of lane 3 (crude wall protein) with lane 4 (purified protein with extension activity) shows that the Ex29-like protein co-purifies with the extension activity. Methods: Lane 1 was loaded with 15 µg of crude wall protein (ammonium sulfate precipitate of 1 M NaCl extract). Lane 2 had 15 µg of the soluble protoplasmic protein fraction. These samples were separated on the same 4–20% gradient SDS polyacrylamide gel, blotted onto nitrocellulose, and probed with rabbit antiserum against cucumber Ex29. Lane 3 was loaded with 0.2 µg of crude wall protein and Lane 4 had 0.2 µg of active oat wall-extension protein purified sequentially by DEAE Sephadex and CM-HPLC. These samples (3–4) were separated on the same 14% SDS polyacrylamide gel, blotted onto nitrocellulose, and probed with antiserum. This assay, with minor variations, was carried out four times with similar results.

Figure 18:
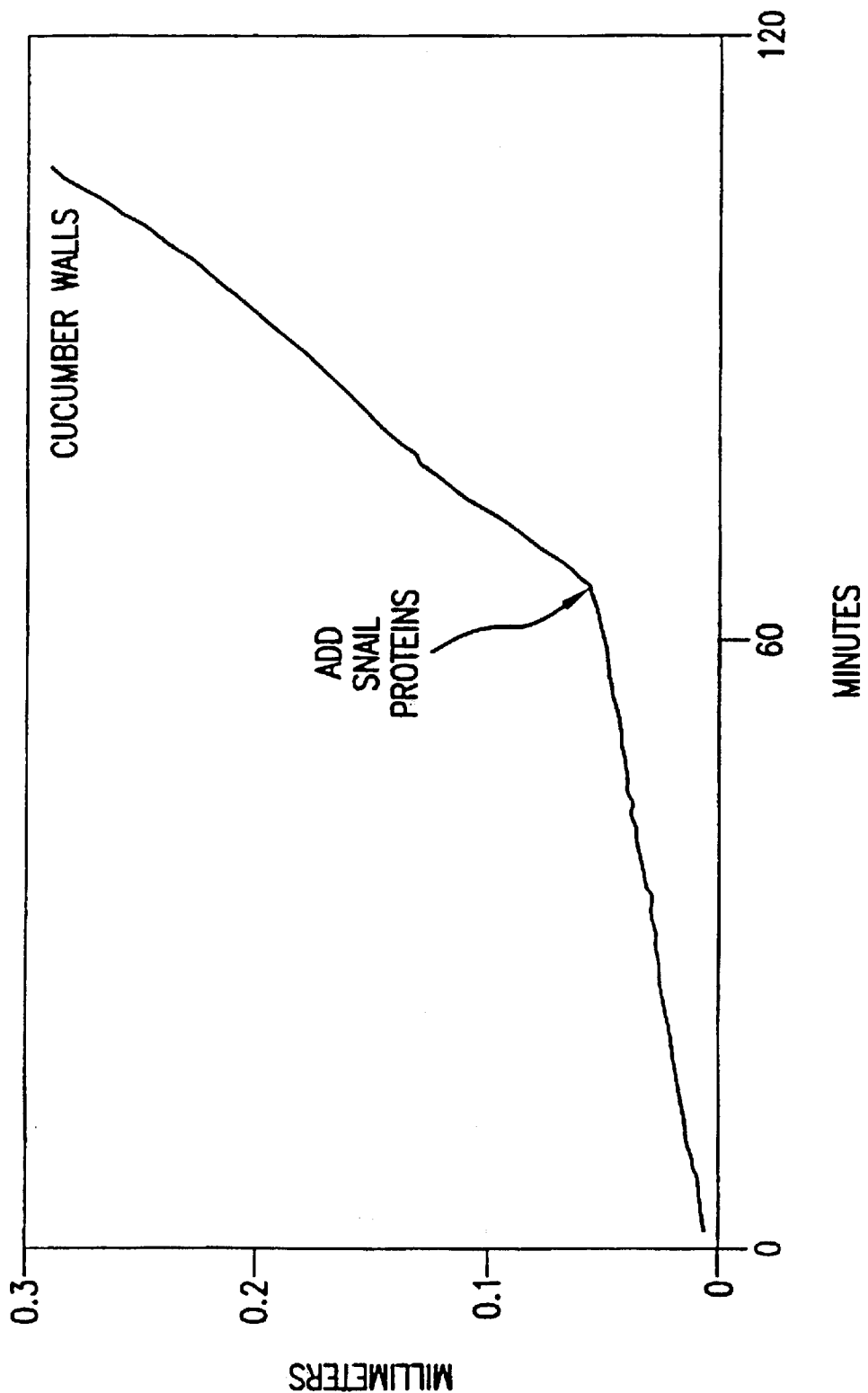

FIG. 18. Extension induced in isolated cucumber walls by proteins from snails.

Cucumber walls were prepared as in the description for FIG. 11. Proteins prepared by dissolving snail acetone powder (10 mg/mL) in 50 mM sodium acetate, pH 4.5, is capable of inducing extension of isolated cucumber walls. The immediate response and the linearity of the extension are unique characteristics that indicate an expansin-like protein may be involved.

Figure 19:
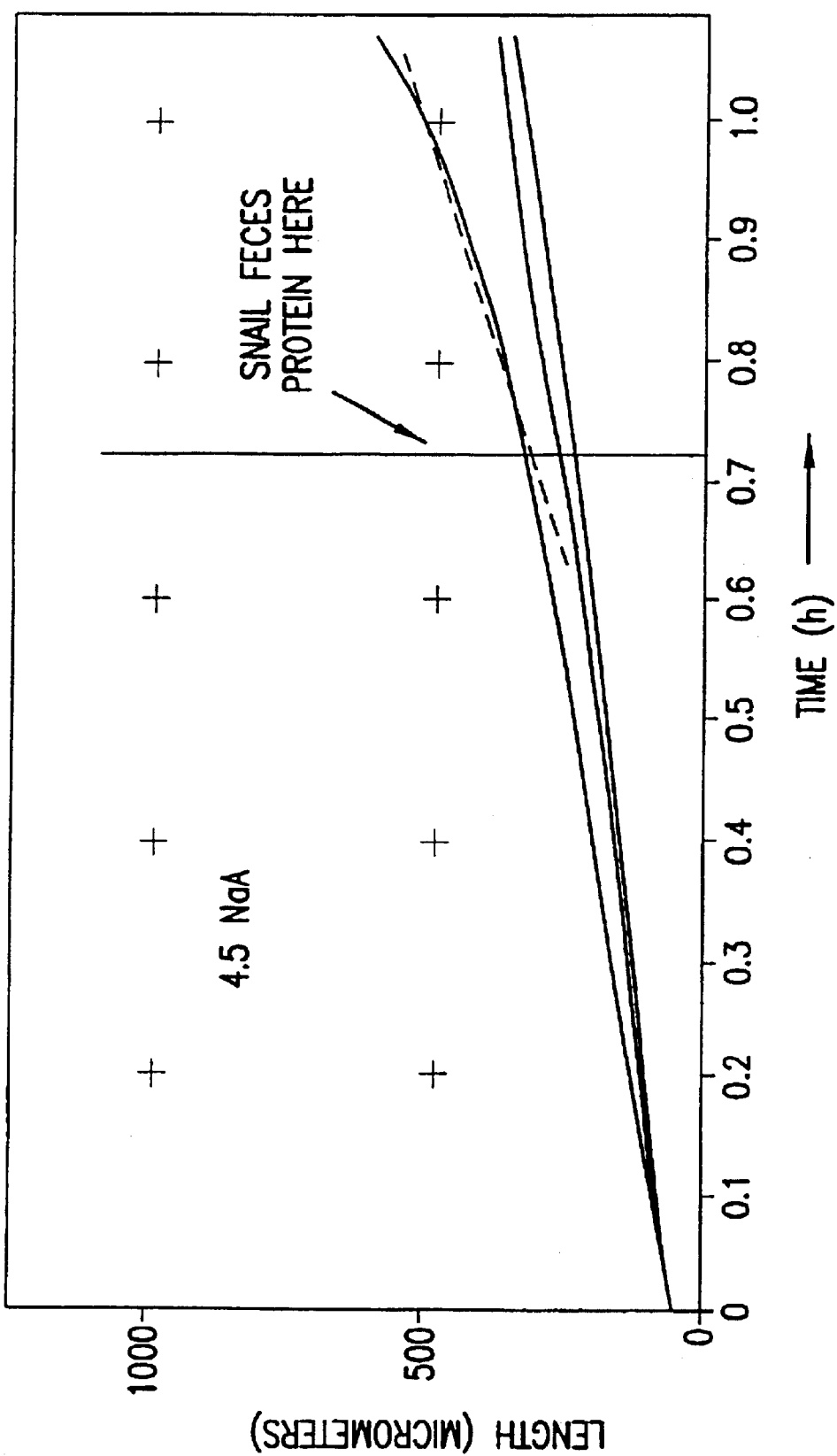

FIG. 19. Extension induced in isolated cucumber walls by proteins from snails feces.

The feces of *Helix aspersa* (snail) induced extension in cucumber walls. The feces were dissolved in 50 mM sodium acetate buffer, pH 4.5. The procedure was as described in FIG. 11.

Figure 20:
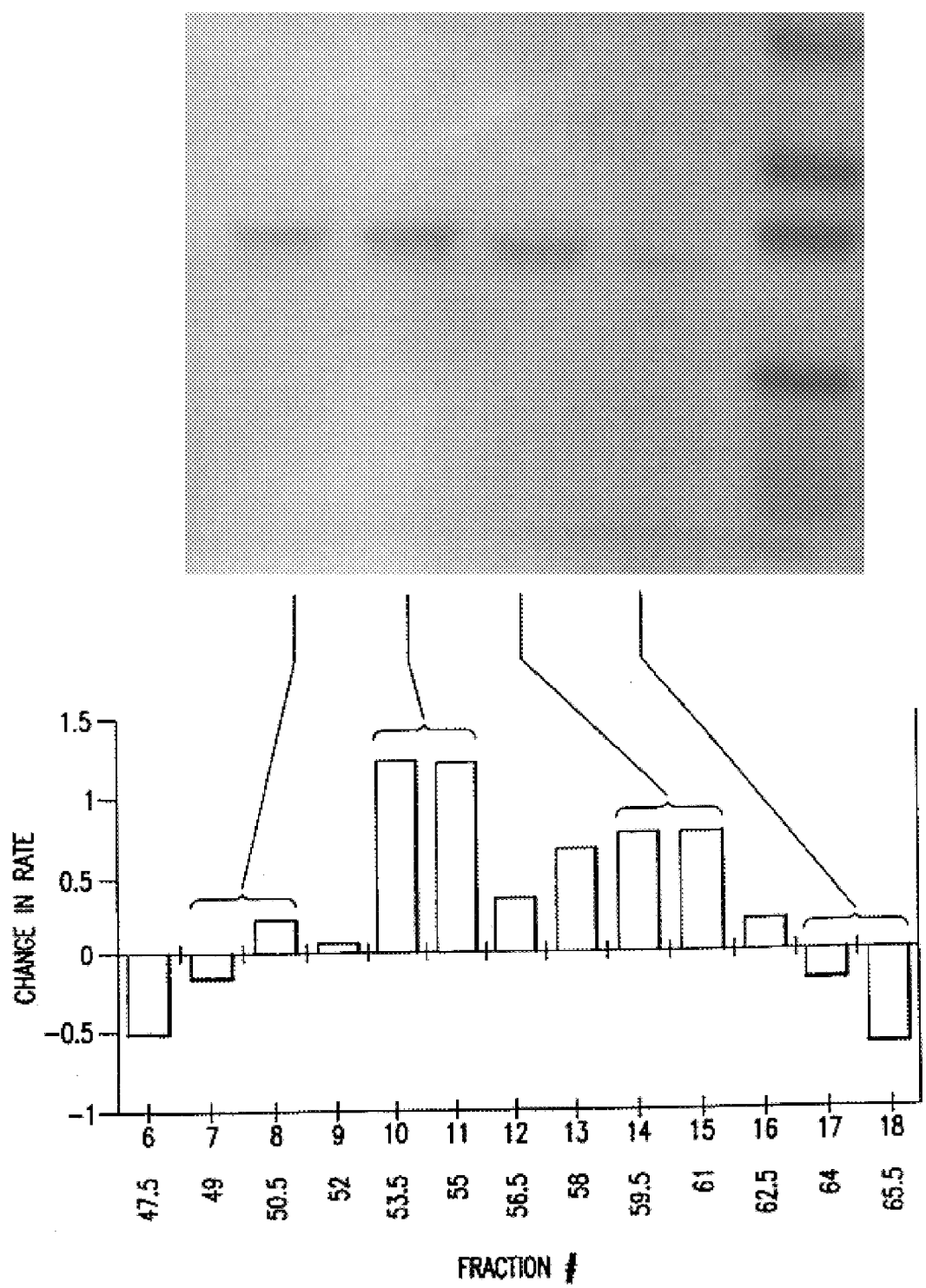

FIG. 20. Western blot analysis of active HPLC-separated proteins fraction from snail.

Acetone powder solution was probed with antibody which was raised against cucumber expansin-29. The analysis was performed as described in FIG. 17. The active fractions show a striking band at about 26 kD, which is similar to cucumber expansin-29. These results provide strong evidence that the wall extension activity found in the snail acetone powder is due to a protein of similar size and similar antigenic determinants as cucumber expansin-29.

Figure 21:

FIG. 21. Western blot of the protein from *Helix aspersa* feces, probed with the antibody PA-1.

Feces from *Helix aspersa* were dissolved as described in FIG. 19 and western blot analysis was performed as in FIG. 20. The single band indicates the presence of an protein antigenically similar to cucumber expansin-29.

Figure 22:
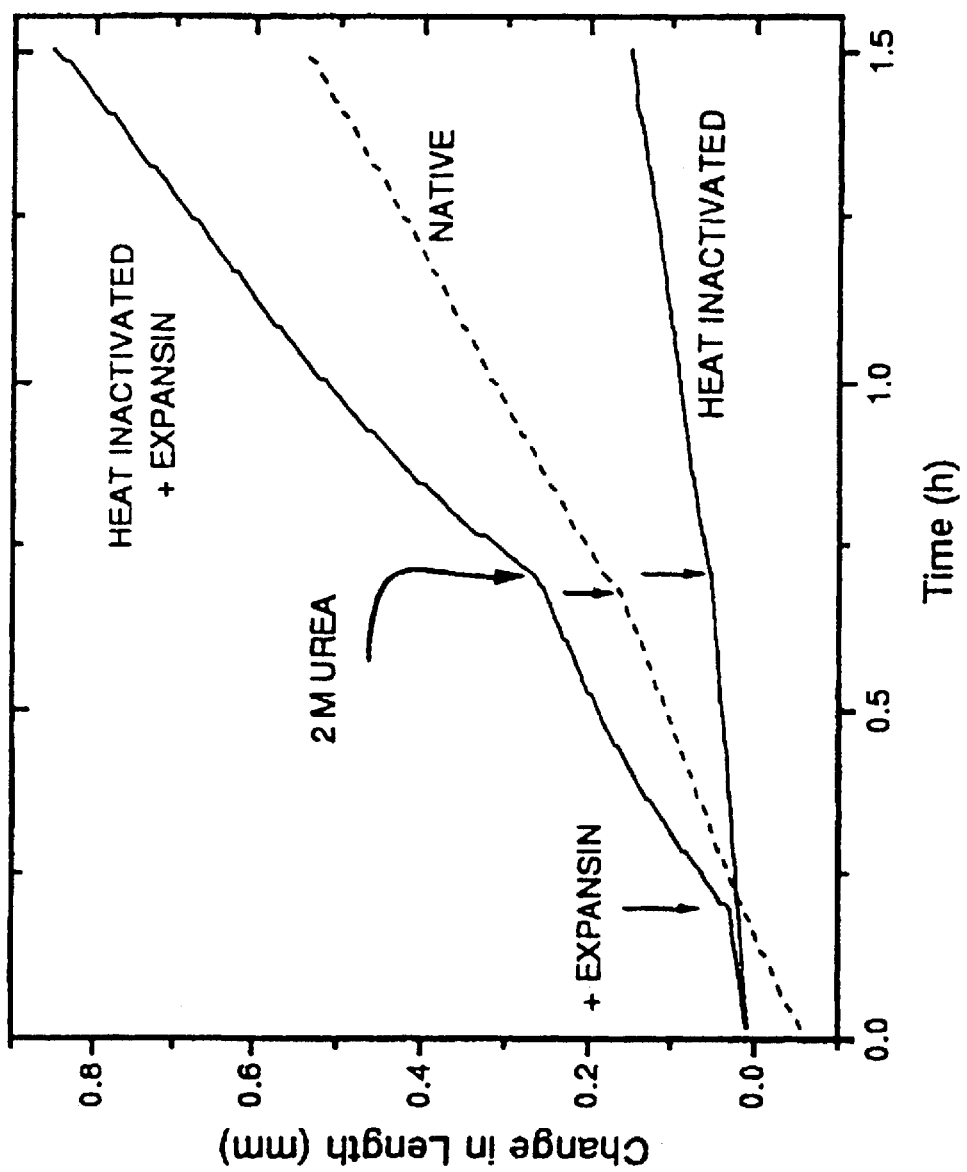

FIG. 22. Effects of 2M urea

This figure shows the effects of 2M urea on extension of native walls, walls reconstituted with expansin, and heat inactivated walls as described in Example 16.

Figure 23:
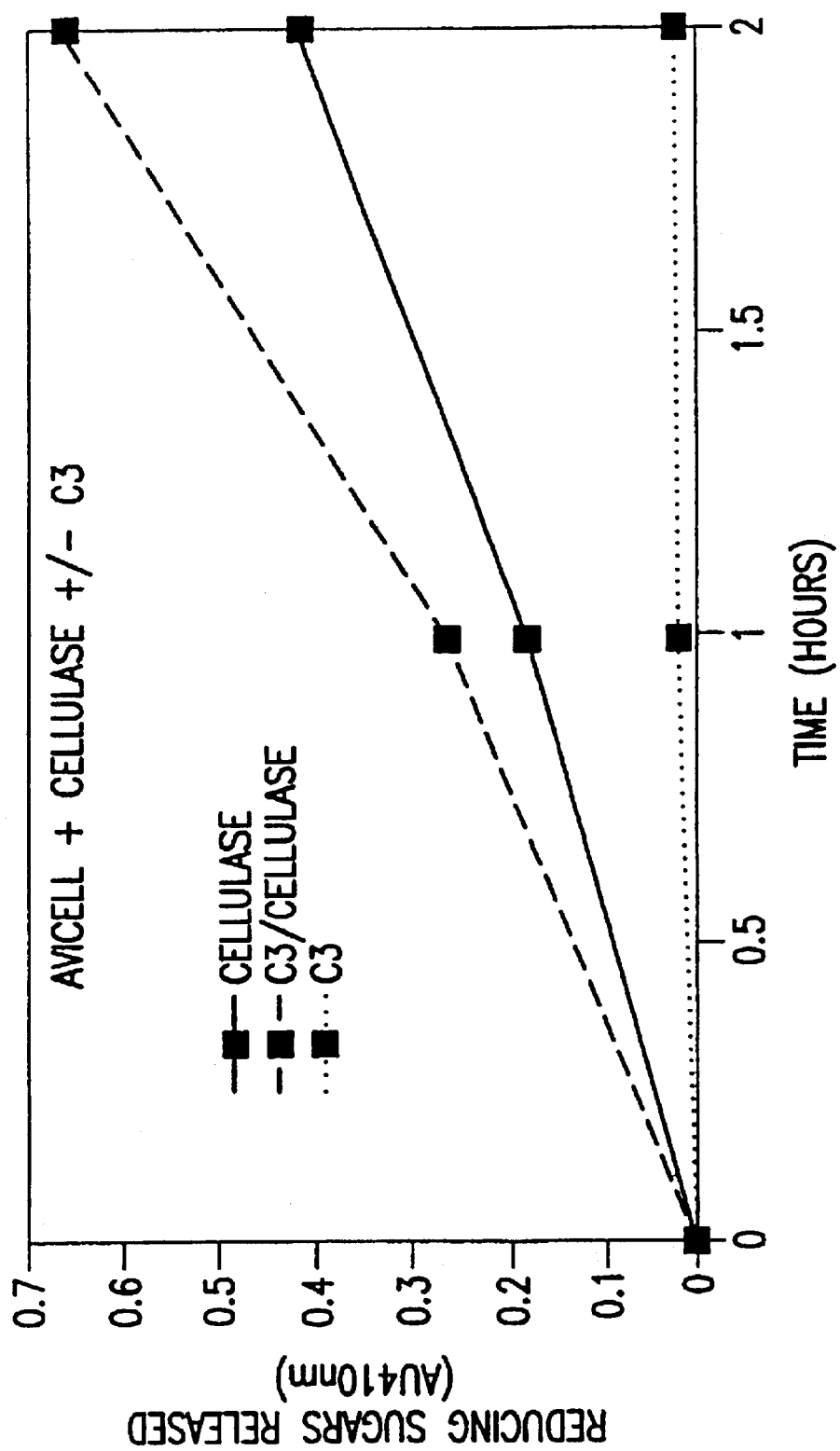

FIG. 23. Use of expansins to enhance the accessibility of cellulose to cellulase and related enzymes and processes.

This figure shows that the cellulose degradation curve of cellulase and expansin is very different from that of cellulase only, or of expansin only, and they do not have a superimposed relationship. It also shows that cellulase and expansin have a synergistic effect in degrading or modifying cellulose.

Figure 24:
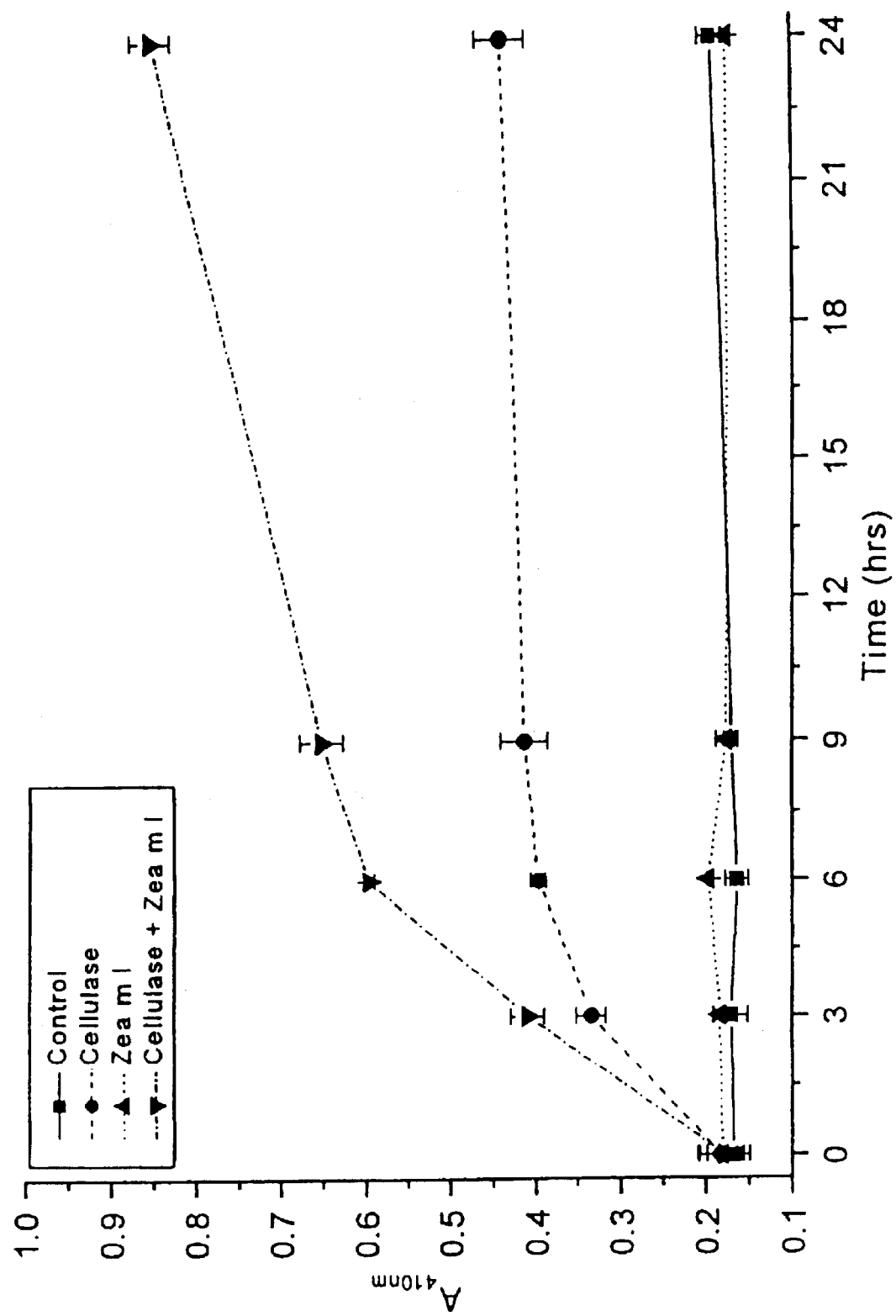

FIG. 24. Maize pollen expansin enhances the accessibility of cellulose to cellulase.

Time course for release of reducing sugars (measured by colorimetric detection of absorbance at 410 nm) from microcrystalline cellulose (Avicel). "Control" contains only buffer, "Cellulase" is buffer plus Trichoderma cellulase added at 100 microgram/mL; "Zea m 1 " is buffer plus the beta-expansin Zea m 1 added at 10 microgram/mL. "Cellulase+Zea m 1" is buffer plus cellulase and Zea m 1 as above. Each point is the mean +/−SE of three measurements.

Figure 25:
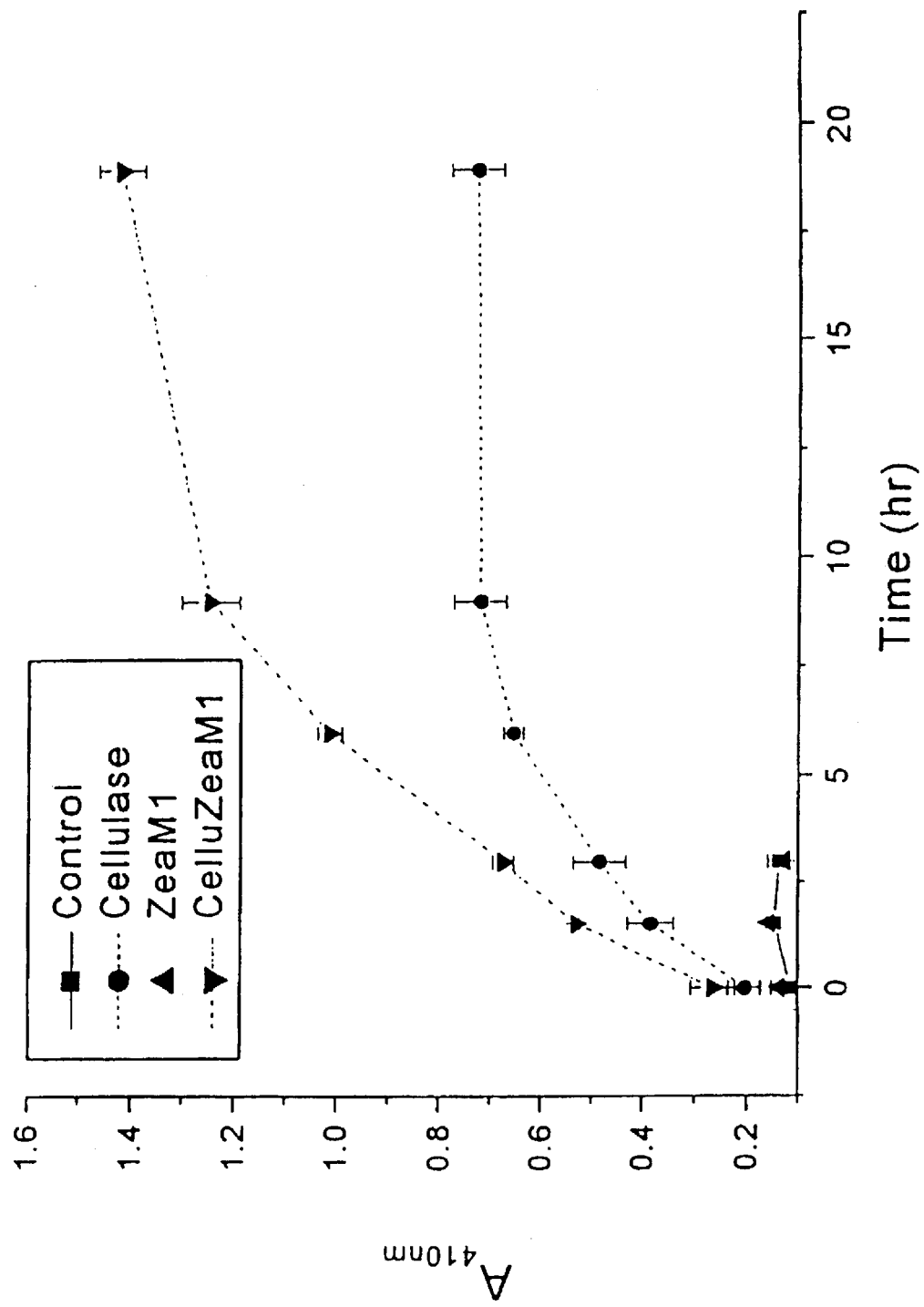

FIG. 25. Time course for release of reducing sugars from microcrystalline cellulose.

Time course for release of reducing sugars from microcrystalline cellulose (Avicel). "Control" is sample incubated in the standard buffer without protein additives. "Zea M 1" is the sample incubated in the buffer containing 50 micrograms/mL of beta-expansin Zea m 1. "Cellulase" is the sample incubated in the buffer containing 100 micrograms/mL of Trichoderma cellulase. "CelluZeaM 1" is the sample incubated in the buffer containing 100 micrograms of Trichoderma cellulase and 50 micrograms of beta-expansin Zea m 1. Each point is the mean +/−SE of three measurements.

Figure 26:
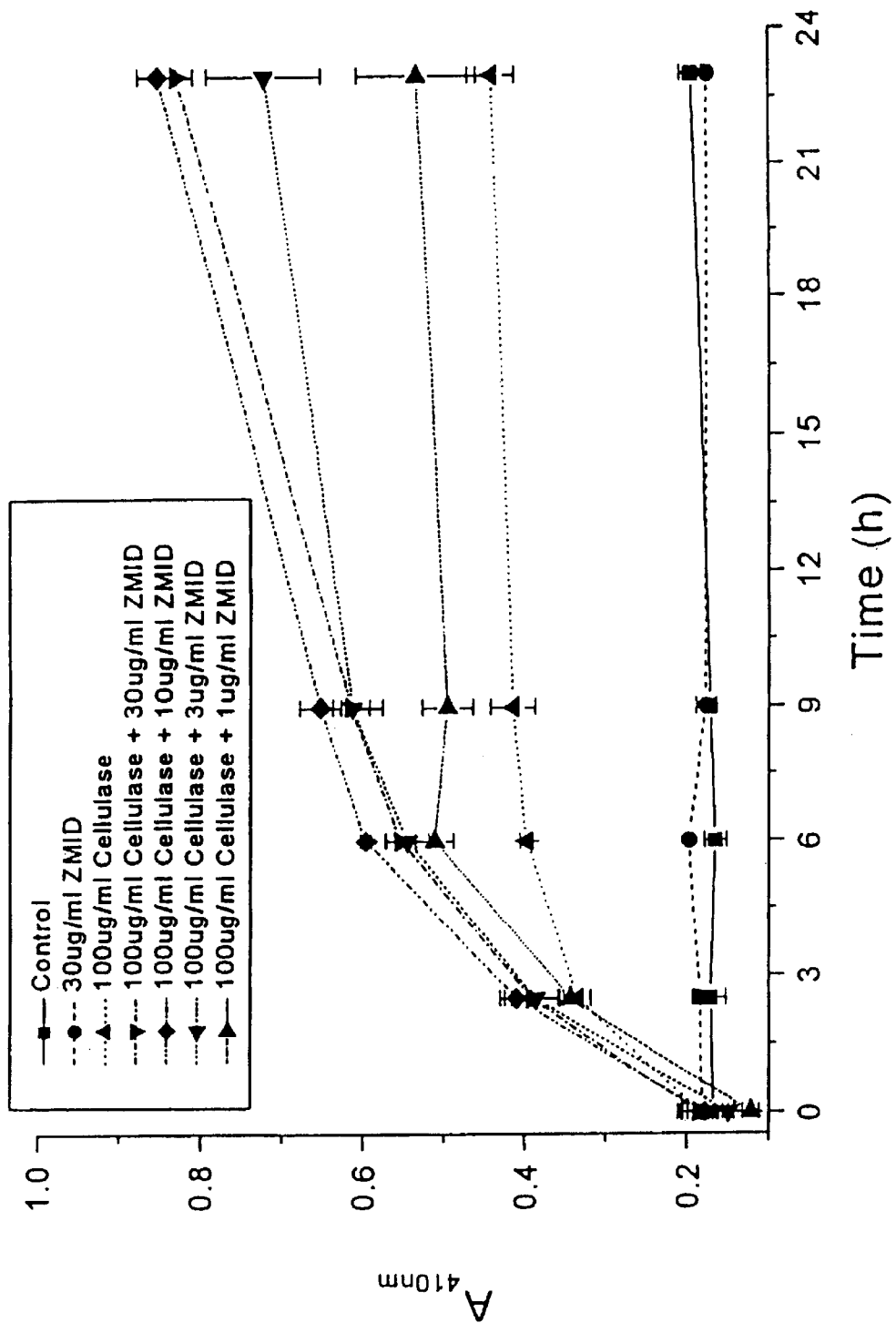

FIG. 26. Maize pollen expansin isoform enhances the accessibility of cellulose to cellulase.

Time course for release of reducing sugars from microcrystalline cellulose (Avicel) by addition of 100 micrograms of Trichoderma cellulase plus varying amounts of beta-expansin Zea m 1 isoform D (ZMID at 0, 1, 3, 10, 30 micrograms/mL). Each point is the mean +/–SE of three measurements.

Figure 27:
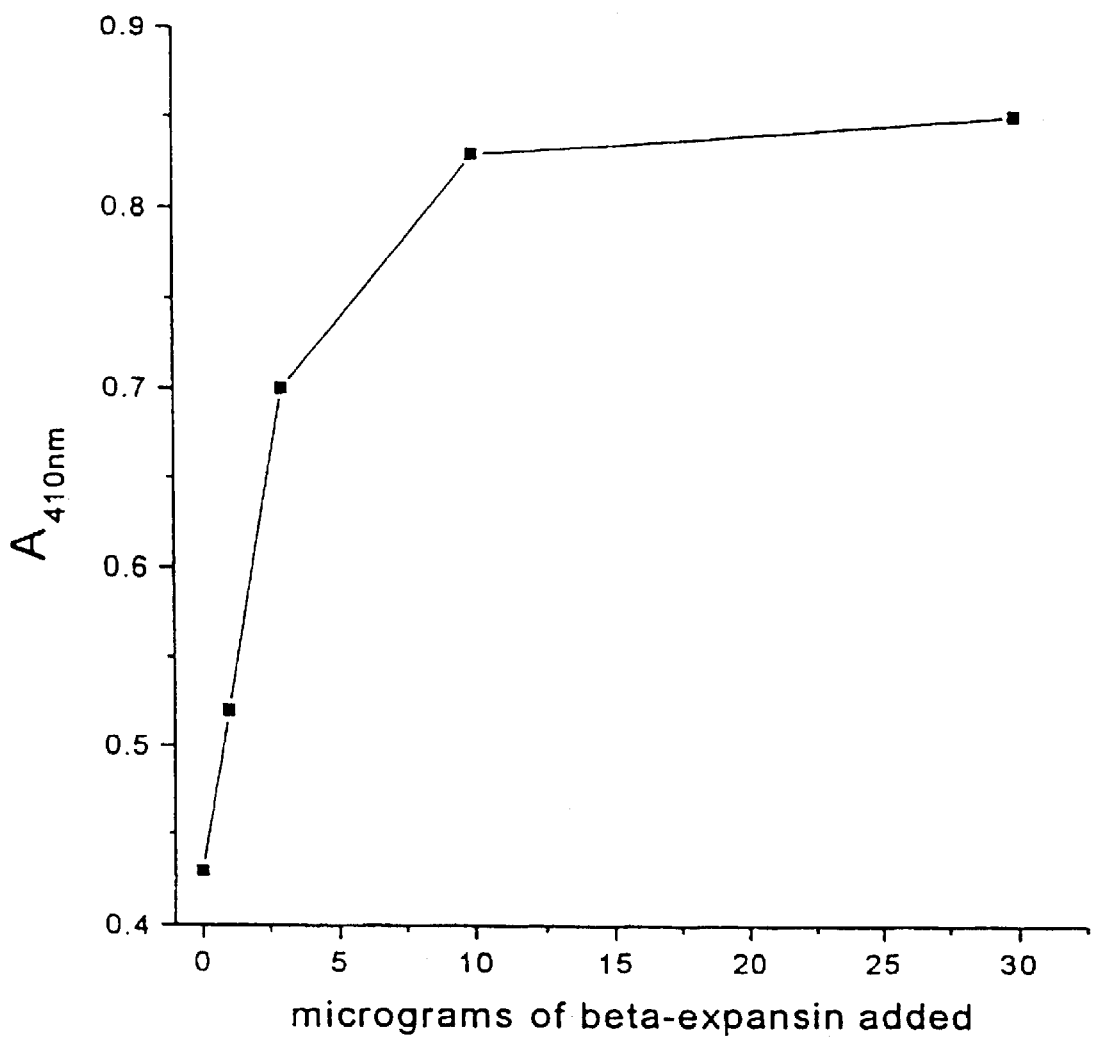

FIG. 27. Dose response curve for the enhancement of cellulytic activity.

Dose response curve for the enhancement of cellulytic activity by beta-expansin. The increase in sugar released, measured as absorbance at 410 nm, after incubation of Avicel with Trichoderma cellulase plus varying amounts of the beta-expansin Zea m 1 is plotted as a function of Zea m 1 added (per mL).

Figure 28:
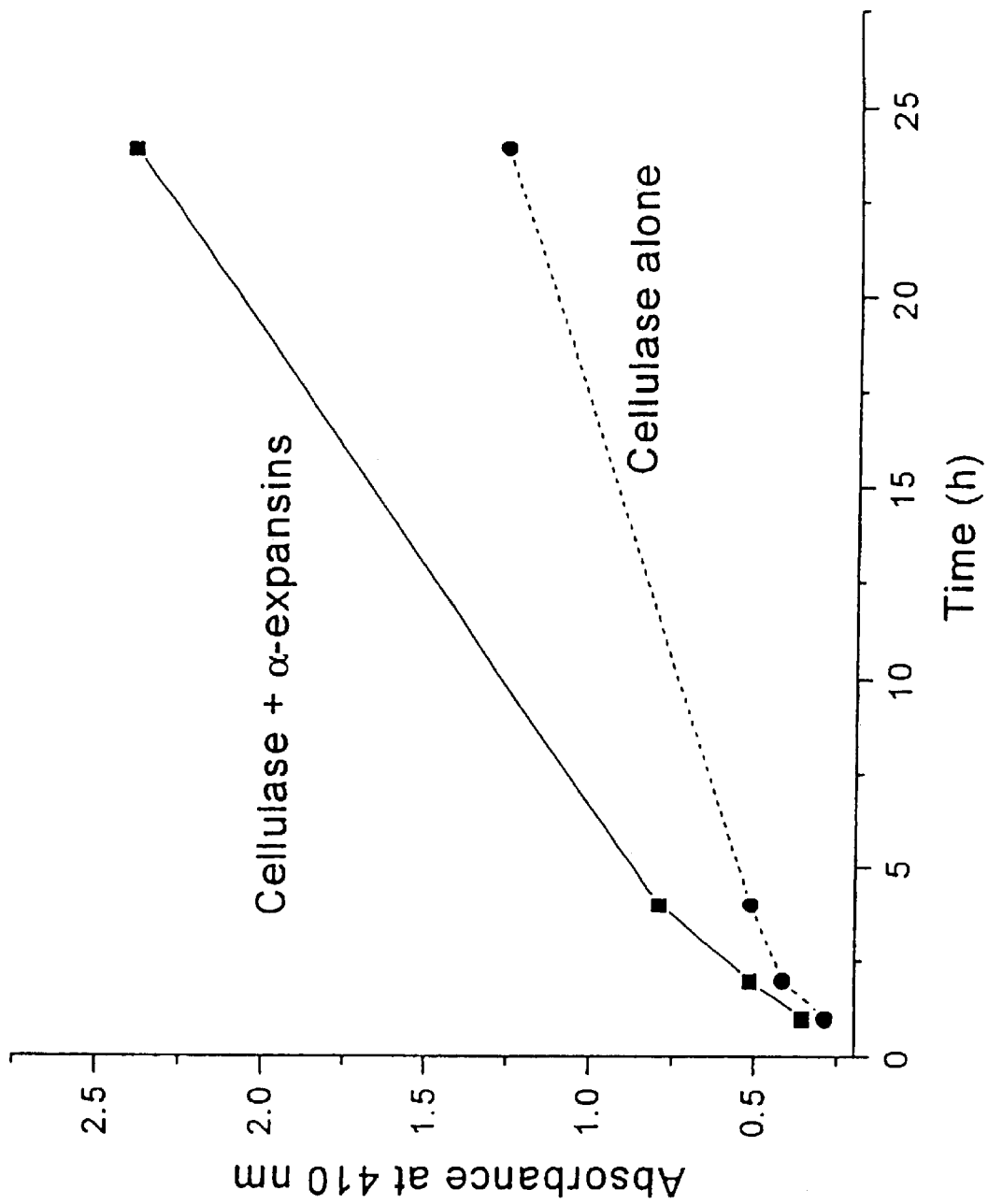

FIG. 28. Cucumber expansin enhances the accessibility of cellulose to cellulase.

Time course for the release of reducing sugars from microcrystalline cellulose (Avicel) by addition of 100 micrograms of Trichoderma cellulase with or without 30 micrograms of cucumber alpha-expansin (cucumber hypocotyl expansins purified by HPLC on a C3 hydrophobic interactions column).

Figure 29:
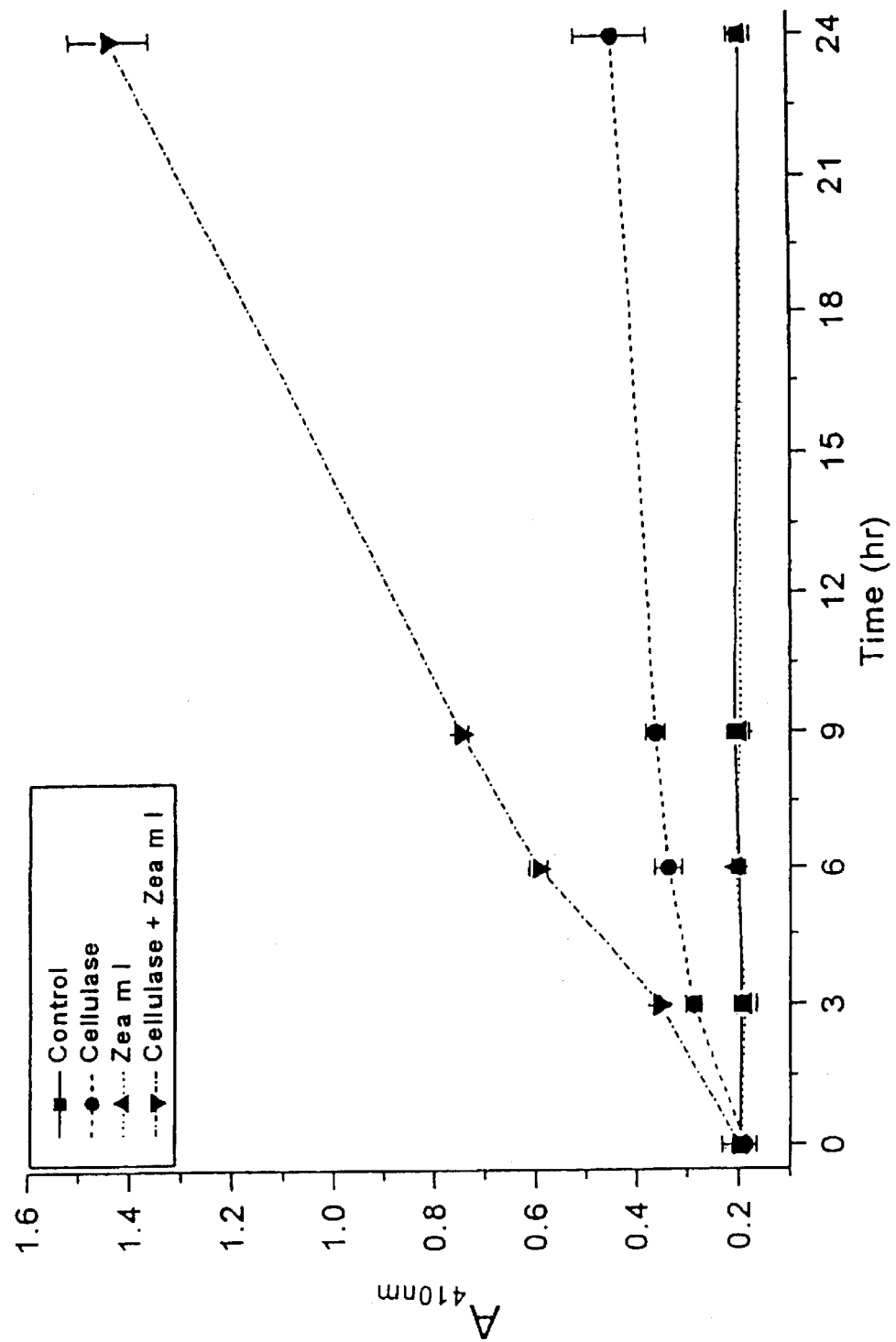

FIG. 29. Maize pollen expansin enhances the accessibility of cellulose to cellulase in paper.

Time course for the release of reducing sugars from Whatman filter paper upon addition of 100 micrograms of Trichoderma cellulase with or without 10 micrograms of Zea m 1. Control contains buffer only. Values are means +/–S.E. of three measurements.

Figure 30:
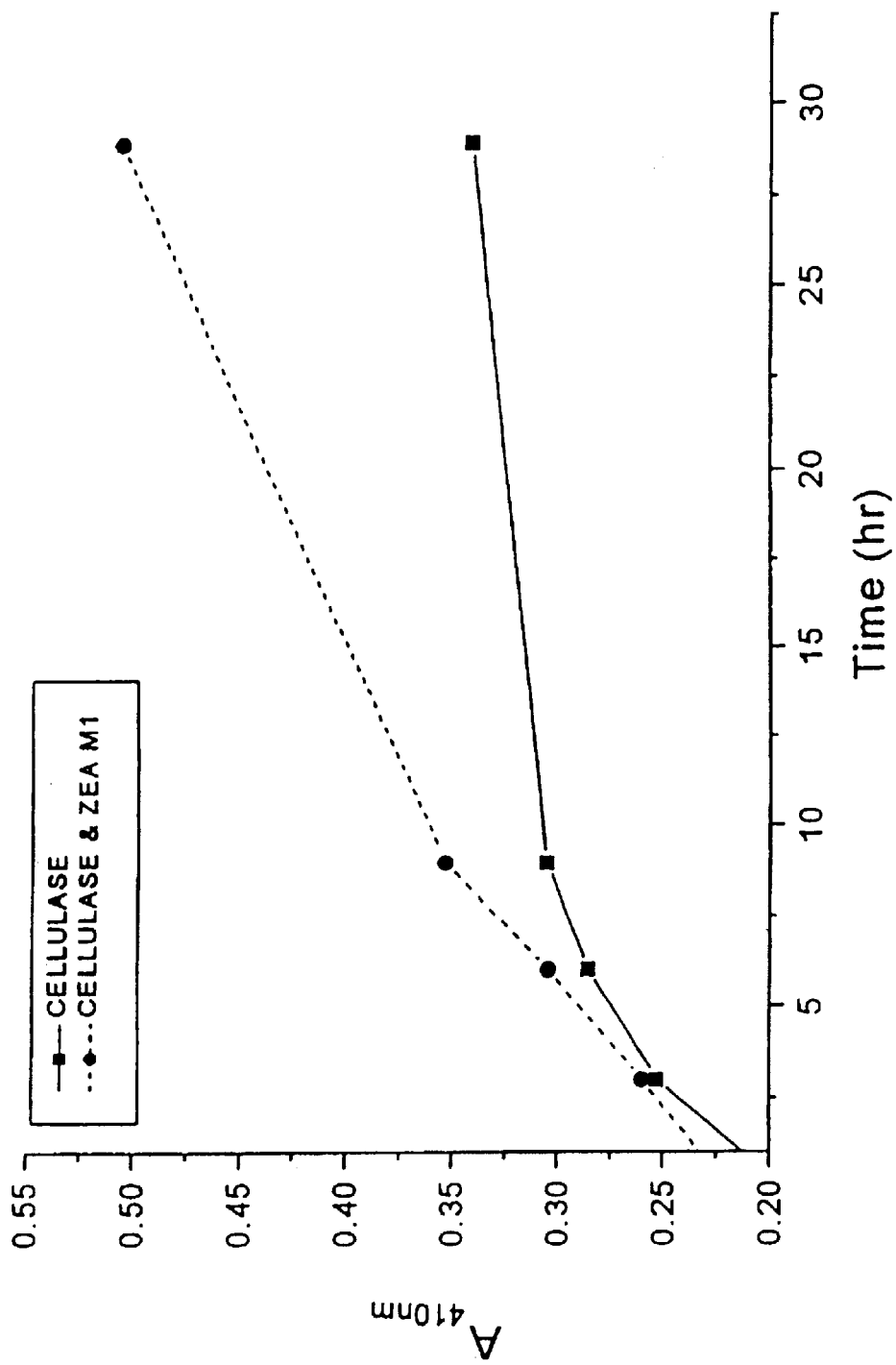

FIG. 30. Effect of pretreatment of cellulose with cellulase on expansin activity.

Time course for cellulase-induced hydrolysis of Avicel pretreated for 24 hours with Trichoderma cellulase. Addition of 10 microgram/mL of Zea m 1 significantly promotes breakdown of cellulose by Trichoderma cellulase (given at 100 micrograms/mL).

DETAILED DESCRIPTION OF THE INVENTION

The present invention describes a new class of proteins named expansins. During the course of detailed studies of plant cell growth, our laboratory isolated from cucumber two novel proteins which we named expansins. Further research found expansins in oat coleoptile as well as in the proteins obtained from the digestive track of snails. The support for these new findings and ways of using it commercially are the object of the present invention.

A detailed embodiment of the present invention involving cucumber proteins cEx-29 and cEx-30, as well as oat protein oEx-29 and expansin-like protein from snail digestive track and its feces sEx is herein disclosed. However it is understood that the preferred embodiment is merely illustrative of the invention which may be embodied in various forms and applications accordingly, specific structural and functional details disclosed herein are not to be interpreted as limiting, but merely as a support for the invention as claimed and as appropriate representation for the teaching of one skilled in the art to variously employ the present invention in any appropriate embodiment.

DEFINITIONS

The term "expansins" include alpha- and beta-expansins (See McQueen-Mason et al., *Plant cell*, 1992, 4:1425–1433; Li Z-C et al., *Planta*, 1993, 191:349–356; Cosgrove, D J et al., *Proc. Natl. Acad. Sci. USA*, 1997, 94:6559–6564.) Alpha-expansins are also disclosed herein and Beta-expansins are the subject of copending application U.S. Ser. No. 09/071,252.

The term "hydrolytic enzymes" as used herein are any enzymes which hydrolyze cellulose, such as beta 1,4-glucanase and cellulase.

The term "beta 1,4-glucanase" as used herein encompasses any enzyme which hydrolyzes the cellulose into its glucan subunits.

The term "cellulases" encompasses any enzyme which hydrolyzes cellulose into smaller units and includes cellulases derived from microbes and other widely available sources. See Gilbert H J, Hazlewood G P, 1993 J Gen Microbiol 139:187–194; Ohmiya K et al. 1997 Biotechnol Genet Eng Rev. 14:365–414.

Modification or degradation of cellulose is used herein to mean the chemical, biological or enzymatic induced alteration of the native structure of the cellulose. Such changes and alterations, are known to those in the art and include those involved in enzymatic degradation and/or hydrolysis of cellulose, as well as chemical modifications involved in a variety of commercial cellulose based products such as textiles, cellulose acetate used in film, nitrocellulose, thickening agents such as those used in paint, papers/pulps, membranes, production of alcohols by fermentation of biomass, and other commercial applications. See Lapasin R. and S Pricl. 1995 The Rheology of Industrial Polysaccharides. Theory and Application. London Blackie Academic and Professional; and M. E. Himmel et al., 1999 Curr Opin Biotechnol 10(4):358–364.

The following abbreviations have been used in the specification: ConA=Concanavalin A; CM=carboxymethyl; DEAE=diethylaminoethyl; Hepes=4-(2-hydroxyethyl)-1-piperazineethanesulfonic acid; DTT=dithiothreitol; Ex29= 29-kD expansin; Mes=2-(N-morpholino) ethanesulphonic acid; HPLC=high-pressure liquid chromatography; PBST= phosphate buffered saline with Tween-20; SDS-PAGE— sodium dodecyl sulfate-polyacrylamide gel electrophoresis.

Our basic approach was to solubilize ionically bound proteins from growing cell walls and assay their ability to restore the endogenous extension activity in heat-inactivated walls. Extension was assayed using a constant load extensometer, in which tissue samples were clamped under constant force and their extension recorded using an electronic displacement transducer (Cosgrove, D. J. Planta, 177:121–130, 1989). The first two proteins possessing the ability to restore the extension activity in heat-inactivated wall were solubilized from wall fragments isolated from the growing hypocotyls of dark-grown cucumber seedlings. After various unsuccessful attempts at reconstitution, we obtained a crude salt-solubilized fraction with the ability to induce extension in inactivated walls, shown in FIG. 1A. The extension induced by this extract mimicked the native extension activity in magnitude and kinetics, i.e. initially high rates decayed over a period of 2 hr to more stable rates of about 2% per hour. These rates are lower than elongation rates of the living stem, but the stress applied to the isolated walls was only one-fifth of the equivalent longitudinal stress imposed on the walls by cell turgor. Like the endogenous extension activity of isolated cell walls, the reconstituted activity required an acid pH and was irreversible (i.e. upon removal of load, the segments did not return to their original length). The addition of protein to native cell walls did not substantially enhance extension, suggesting that endogenous activity was saturating or that binding sites were not accessible to the added material.

Figure 1A:
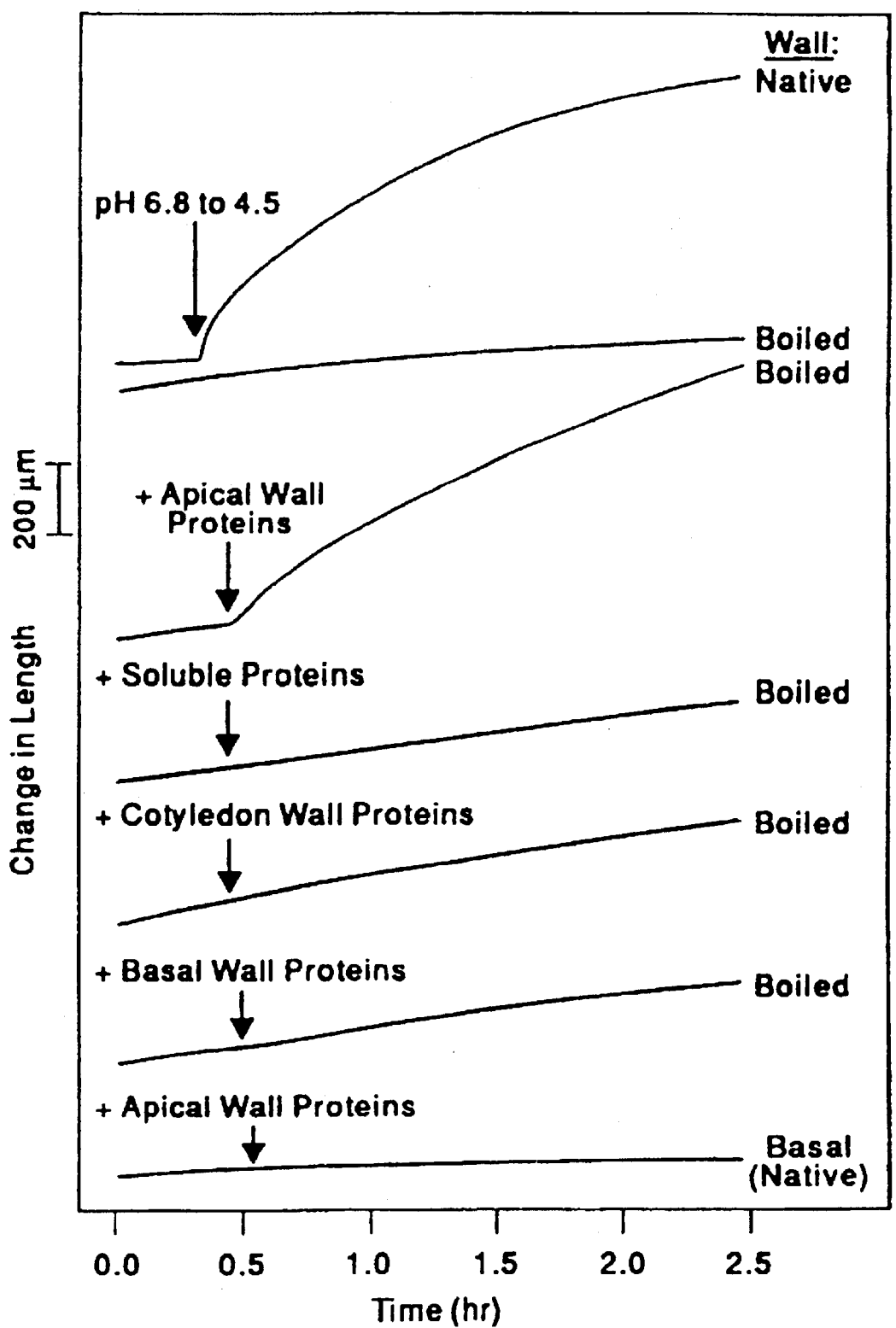
FIG. 1. Extension curves of native and reconstituted isolated cell wall specimens obtained using a constant load extensometer.

The active material appeared to be restricted to the growing region of the hypocotyl. When wall fragments from basal (non growing) stem tissue or from the cotyledons (which expand negligibly in our conditions) were extracted, proteins solubilized in the same way did not induce wall extension (FIG. 1A). These results suggest that nongrowing tissues lack the active material; however, we cannot exclude the possibility that the active material was present in the tissue but more firmly bound, inactivated during extraction, or lost during wall isolation. Soluble cytoplasmic proteins (collected as expressed cell sap or as homogenate) showed no activity, whilst proteins which were salt solubilized in an equal volume from cleaned wall residues taken from the same tissue showed clear extension inducing activity, indicating an association of the extension activity with the wall.

The wall extract from growing cucumber walls did not induce extension of walls from the basal (non elongating) stem (FIG. 1A). Evidently, during maturation the wall is biochemically modified so that it is not susceptible to extension by this material. Perhaps peroxidative cross-linking of lignin or structural proteins such as extensin is involved in this loss of sensitivity.

Figure 1B:
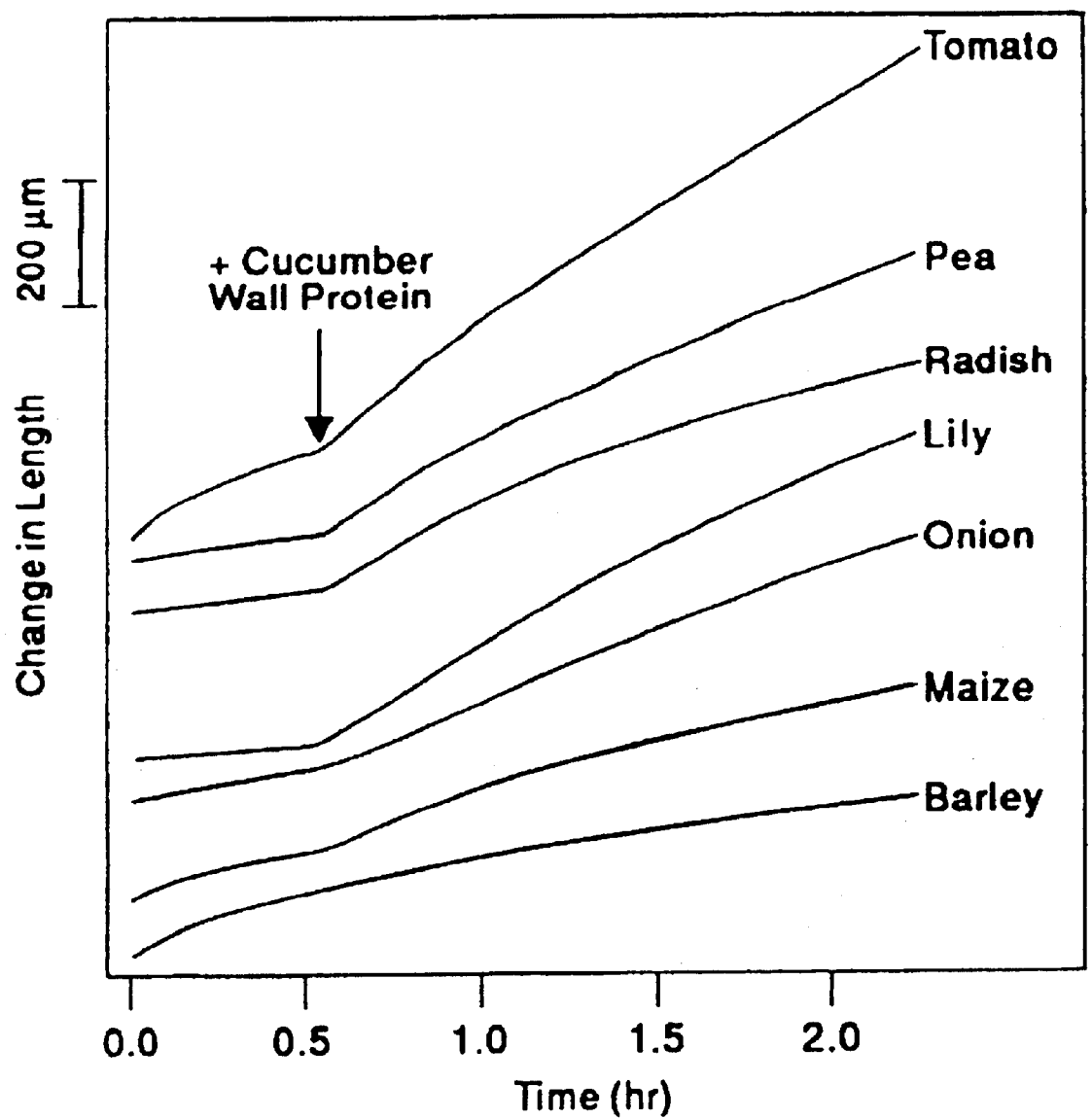

The extension activity showed an interesting pattern of species specificity. FIG. 1B shows that the cucumber wall extract was active on various dicot seedlings (pea, radish, cucumber and tomato) and on monocots of the Amaryllidaceae (onion and zephyr lily). In contrast, the extract had a much smaller effect on the coleoptile wall of graminaceous monocots (maize and barley). As graminaceous monocot cell walls differ from those of dicots by having less pectin and hydroxyproline-rich glycoprotein, and also by having a different type of hemicellulose, it may be that the active fraction extracted from cucumber walls interacts with one or more of these components to induce extension. It may also be that these grass cell walls are cross-linked (not necessarily covalently) in a manner that renders them immune to the cucumber extract. In contrast monocots of the Amaryllidaceae have a cell wall composition more similar to dicots than to the graminae, and this probably explains their susceptibility to the cucumber derived activity.

The cucumber wall extract was separated by ammonium sulfate precipitation followed by sequential HPLC, shown in FIG. 2, first using a hydrophobic interactions column, where a single peak of activity desiphated as the C3 proteins was obtained, and then using a cation exchange column from which the activity was eluted as two distinct peaks These fractions we have designated S1 and S2 with respect to their order of elution. FIG. 3 shows the analysis of the active fractions by SDS-PAGE which revealed a major band of relative molecular mass 29 kD associated with S1, while S2 contained a major band at 30 kD (FIG. 3). Active extracts have also been separated by native PAGE and by liquid chromatography with hydroxyapatitc, gel filtration media, and DEAE anion exchangers, where activity was consistently associated with these two bands (data not shown). The S1 fraction required only 0.3–1.0 micrograms of protein to reconstitute extension rates similar to that of native extension, while it required 1.0–2.0 micrograms of S2 to do this.

Cucumber expansins induced extension of walls from several dicot and monocot species, but had little effect when assayed with coleoptile walls from maize and barley. Grass coleoptiles have been a favored object of growth studies since Darwin's analysis of phototropism and have been instrumental in many discoveries about plant growth, including the discovery of auxin. The wall composition of grass coleoptiles is notably different from that of dicots and other monocots nevertheless, coleoptile walls, like dicot walls, do exhibit a strong acid-induced extension in vitro and in vivo. These observations led us to postulate that a wall protein, with functions analogous to the cucumber expansins, might mediate the endogenous acid-induced extension of coleoptile walls. Therefore, in further study we attempted to identify oat coleoptile proteins that could induce wall extension, using the wall extraction and reconstitution approach that proved successful with cucumber walls.

Figure 11A:
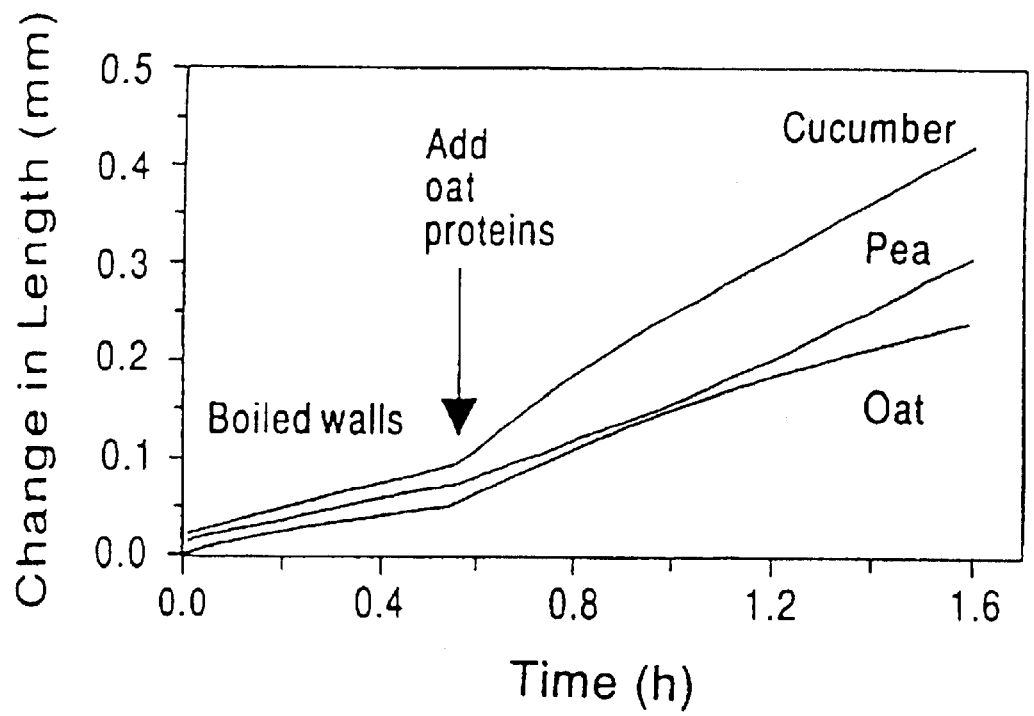

To identify the hypothetical oat proteins responsible for wall extension, we used 1 M NaCl to extract proteins from cell walls of etiolated oat coleoptiles. Proteins in this crude extract were precipitated with ammonium sulfate, desalted, and fractionated on a DEAE Sephadex anion exchange column. The unbound proteins passing through this column possessed the ability to induce extension in heat-inactivated walls from oat coleoptiles (FIG. 11A). Moreover, this active fraction also induced extension of heat-inactivated cucumber hypocotyl walls and pea cpicotyl walls (FIG. 11A). This result was surprising because earlier results led us to expect poor cross-reactivity between extension proteins and walls from dicots and grass coleoptiles.

Figure 8A:
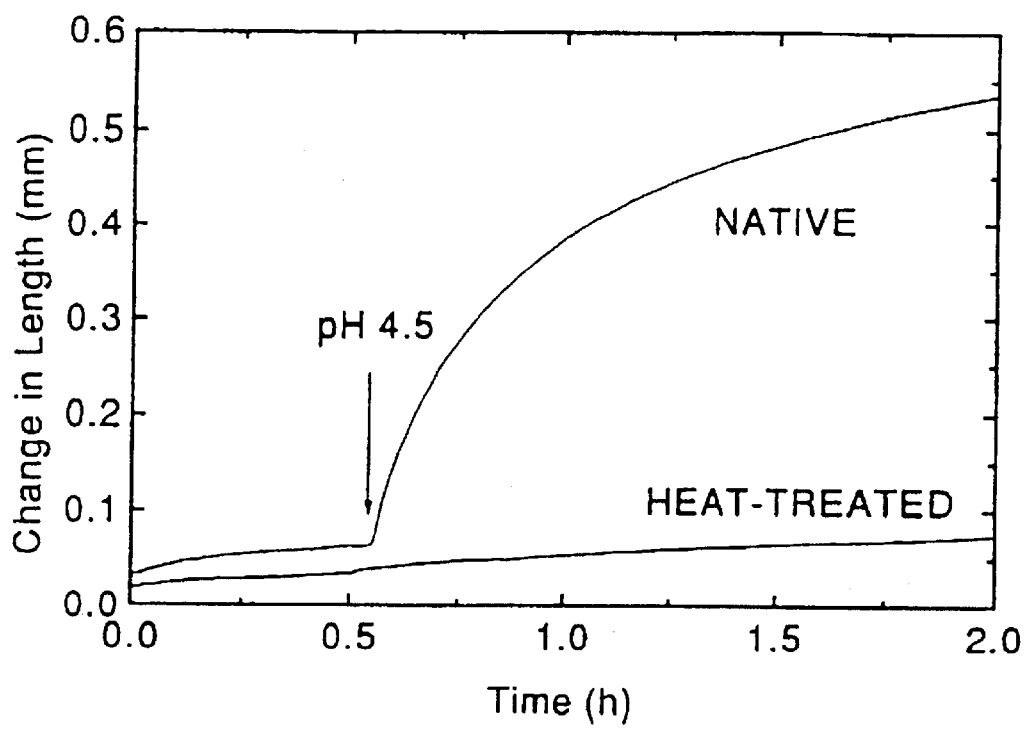
Figure 8B:
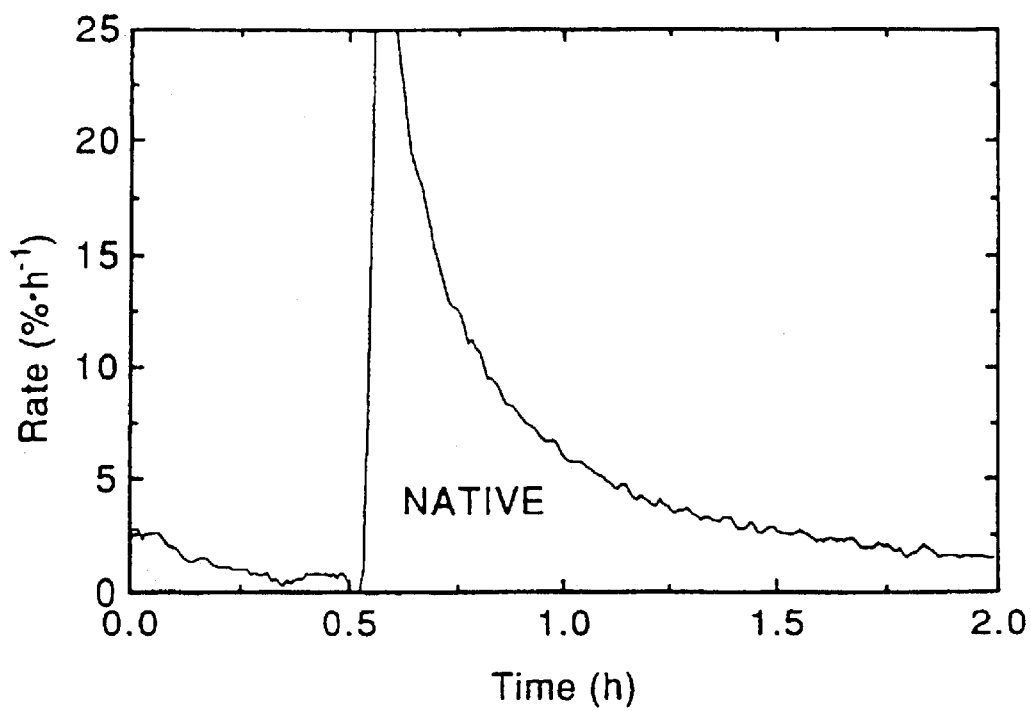

FIG. 8 shows an example of acid-induced extension of oat coleoptile walls. When native walls were clamped under constant tension at neutral pH, the extension rate was low 30 min after application of the load and could be greatly increased by replacing the neutral buffer with a buffer of pH 4.5. The wall extension rate decreased continuously with time after the change to acid buffer (FIG. 8B). Addition of 10 mM dithiothreitol, a sulthydryl reducing agent, increased the extension rate and stabilized it (FIG. 9). This effect is similar to that previously found with cucumber walls (Cosgrove 1989). Inclusion of dithiothreitol throughout the extension period resulted in a simpler decayto aconstant extension rate (FIG. 10). Pretreatment of the coleoptile wall with boiling water for 15 sec to inactivate wall proteins eliminated the acid-induced extension (FIG. 8A), suggesting that extension of these walls may be due to a protein-mediated reaction. These observations are consistent with previous reports of acid-induced extension in oat and cucumber walls.

Figure 11B:
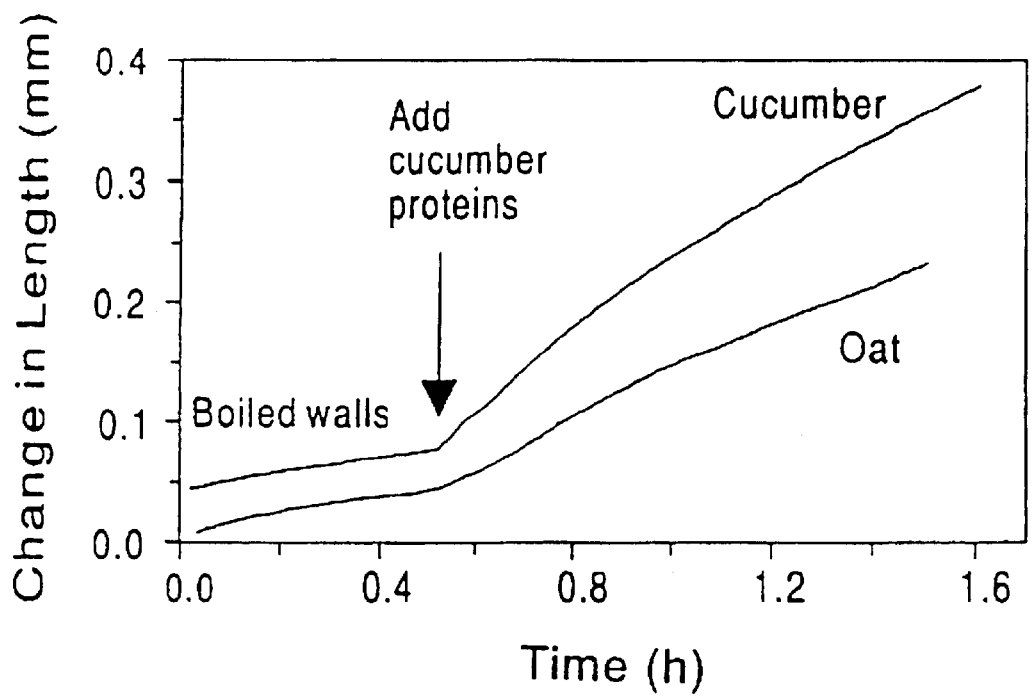
Figure 12B:
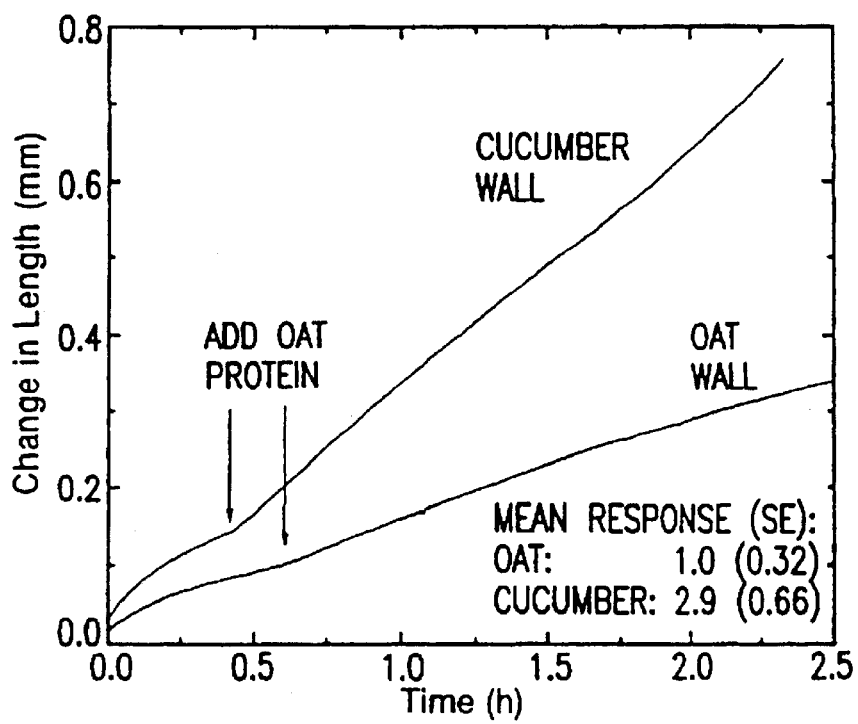

To pursue this point further, we tested the ability of cucumber expansins to induce extension of oat coleoptile walls. As shown in FIG. 11B, they indeed induced extension in oat coleoptile walls, but with less effectiveness than when assayed with cucumber walls. This last point is quantified in FIG. 12A, which compares responsiveness of cucumber and oat walls to a partially purified cucumber expansin fraction. The maximal response of cucumber walls was about three times higher than that of oat walls. To obtain the same extension response in oat walls as was elicited in cucumber walls by 2 g mL$^{-1}$ of cucumber protein, ten times as much protein was required. FIG. 12B shows that cucumber walls were similarly more sensitive to the active oat extract than were oat walls. The protein-induced extension was stabilized by inclusion of 1–10 mM dithiothreitol in the incubation buffer (data not shown). We also confirmed that cucumber expansins caused very little extension of barley coleoptiles (data not shown). Thus, we conclude that oat coleoptile walls are substantially more responsive in these reconstitution assays than barley coleoptile walls, but less responsive than cucumber walls.

Despite the quantitative differences, these results show that oat and cucumber proteins can induce qualitatively similar extension responses in oat and cucumber walls. We thus infer that a similar biochemical mechanism is involved in acid-induced wall expansion in grasses as in dicots.

One might expect that extraction of frozen/thawed coleoptiles with 1 M NaCl might remove most or all of the acid-extension response. FIG. 13 shows that overnight extraction of coleoptiles indeed diminished their acid-extension response. This loss could be due to extraction of the expansins; alternatively, the walls or their proteins may have been modified in some other way so that they lost the acid-extension response. Cucumber walls were previously found to lose their native extension response when they were pre-incubated in neutral pH (Cosgrove 1989). Further work will be needed to differentiate between these and other possible explanations.

To assay the pH dependence of the extractable expansin activity from oats, we used cucumber hypocotyl walls as the "substrate" for measuring the extension activity of oat proteins. Cucumber walls were used because they were easier to prepare, broke less often, had lower baseline extension rates, and proved to be a more sensitive substrate for extension assays than did the walls from oat coleoptiles. The active oat fractions from the DEAE-column had a pH optimum between 4.5 and 5.0 (FIG. 14). At pH 3.5 or 5.5, the activity was reduced by about 50%. In contrast, cucumber expansins displayed a broader pH optimum, with high activity maintained at pH 3.5.

When the active proteins from the DEAE-column were passed through a Concanavalin A (Con A) column, the majority of the extension activity did not bind to the lectin column, suggesting that the activity was not associated with glucosyl- or manosyl-glycoproteins. When the active fractions which passed through the Con A column were further fractionated by HPLC on a carboxymethyl cation exchange column, extension activity was eluted as a single major peak at about 15 min (FIG. 15). The activity of this protein fraction had an acid optimum similar to that shown in FIG. 14 (data not shown). SDS-polyacrylamide gel electrophoresis revealed that a protein with molecular mass of about 29 kD was associated with this active fraction (FIG. 16). We designate this protein as oat expansin-29 (oat Ex29, oEx-29).

A summary of the purification steps for the oat Ex29 is shown in Table 1. This protein was purified sequentially by ammonium sulfate precipitation, DEAE-chromatography, Con A affinity chromatography and CM cation exchange chromatography. If the extension activity in ammonium-sulfate-precipitated proteins is taken as 100%, a purification of 51 fold with 69% yield was obtained after two steps of ion exchange chromatography. Because Con A affinity chromatography did not significantly purify oEx-29, this step was often omitted without significant effect on the purification.

To examine whether expansin activity was also present in the protoplasm of oat coleoptiles, we fractionated the soluble protoplasmic proteins (all proteins in the coleoptile homogenate not bound to the wall) by ammonium sulfate precipitation and DEAE-column chromatography. Little or no activity was detected in any fractions (data not shown), suggesting that the responsible protein was bound to the cell walls of oat coleoptiles.

Because oat Ex29 was capable of catalyzing extension of walls from cucumber, we wished to test whether it is immunologically related to the 29-kD cucumber expansin cEx-29. FIG. 17 shows that the oat Ex-29 was specifically recognized by an antibody raised against cucumber Ex-29. Pre-immune serum under the same conditions did not label Ex-29 (not shown). Little signal was detected in the soluble protoplasmic fraction of oat coleoptiles, which is consistent with our other evidence that the Ex-29 is a wall-bound protein. When equal amounts of crude and purified wall protein were assayed by Western analysis, the purified protein gave a much greater signal (FIG. 17). These results demonstrate that the extension-inducing activity co-purifies with the protein that is antigenically related to cucumber Ex-29.

Our results show that oat coleoptile walls possess a protein that can mediate acid-induced extension of grass coleoptile walls and dicot walls. This protein resembles the cucumber 29-kD expansin in that it induces extension at acid pH but not at neutral pH, its activity is stabilized by dithiothreitol, it has a similar size adjudged by SDS-PAGE, and it is specifically recognized by an antiserum raised against the cucumber protein. Because of these similarities between the oat and cucumber expansins, we propose that expansins are evolutionarily conceived proteins that underlie at least part of the acid-extension response common to the walls of many plant species.

The similarity between oat and cucumber expansins surprised us because we found that cucumber expansins caused little extension of maize coleoptile walls and no extension of barley coleoptile walls. We confirmed that barley walls were unresponsive to cucumber expansins, but our positive results with oat coleoptiles show that this insensitivity is not a general property of grass coleoptiles. We do not know why barley walls failed to extend in the presence of cucumber or oat expansins.

The similarity between oat and cucumber expansins is also surprising because the matrix components of the wall are believed to be important for wall loosening and extension, yet these components are quite different for grass walls and dicots. The major matrix polysaccharides of the coleoptile wall are (1→3, 1→4)—D-glucans and arabinoxylans whereas dicots contain principally xyloglucans and pectins. Dicot walls contain hydroxyproline-rich glycoproteins of the extensin family whereas grass walls contain much lower amounts of such proteins. It may be that expansins interact directly with wall components common to both types of walls (e.g. cellulose or a minor matrix component) or that they can act on different glycans with similar functions, e.g. xyloglucans and (1→3, 1→4)—D-glucans.

Although oat Ex29 can induce an acid-dependent extension in coleoptile walls, there are notable differences between the native and reconstituted acid-extension responses in coleoptiles. First, the acid response of native walls includes a large, but transient, burst in extension, which is mostly decayed away by 60–90 min. This burst is largely lacking in oEx29-reconstituted extensions, which resemble more closely the steady extensions which outlast the transient (e.g. FIGS. 8 and 10). Second, the pH dependence of reconstituted extension (FIG. 14) does not exactly match the pH dependence reported for acid-extension responses of isolated coleoptile walls. The reconstituted extensions displayed a maximum at pH 4.5 and fell off at lower pH values, whereas acid extensions of native coleoptile walls did not fall off at lower pH values. Third, the maximum extension rate inducible with exogenous Ex29 was substantially less than acid-extension responses of native coleoptile walls (i.e. about 2% $h^{-1}$ for reconstituted extensions versus about 5% $h^{-1}$ for the stable component of native wall extensions or 20–30% $h^{-1}$ for the immediate response of native walls).

These differences between the reconstituted and native acid-extension responses of coleoptile walls could indicate that oat coleoptiles possess additional acid-extension processes, other than the one mediated by oEx-29. On the other hand, these differences might also result from inadequacies in our reconstitution methods. For example, heat inactivation of the coleoptile wall by treatment with boiling water may modify the wall's structure so that it is not as susceptible to oEx-29 action. There may also be differences due to poor accessibility of exogenous Ex-29 to its site of action in the wall, or with need for ancillary wall enzymes that are inactivated by heat treatment. Hence, we believe that, at this stage, caution is warranted in interpreting the differences between native and reconstituted extensions.

From the characteristics of oEx-29-induced extension of coleoptile walls and the above considerations, we propose that oat Ex29 is responsible for at least part of the long-term (>1 h) acid-induced extension responses of oat coleoptiles. This view is strengthened by the findings that reconstituted wall extension and endogenous wall extension exhibit similar sensitivities to biochemical activators and inhibitors. In cucumber, exogenous expansins can restore extension rates as high or higher than the long-term extension rates in native walls exposed to acid pH. Although we believe there to be good reasons for thinking that expansins mediate the long-term acid-induced extension of isolated walls, their role in the growth of living tissues has not been directly addressed. This assessment will require experiments in which the action of expansins are specifically inhibited or enhanced. Further studies of the biochemical action of expansins and the genes that encode them may provide the tools for this assessment.

Digestive track of many animals contain enzymes able to catalyze reactions weakening various chemical bonds. We postulated that the digestive track of animals which consume green parts of plants may contain proteins of action similar to expansins. We found expansin-like proteins in the digestive track and feces of the snail *Helix aspersa*. Western blot analysis of the snail proteins probed with the antibody raised against cucumber expansin cEx-29 indicates the presence of an protein antigenically similar to cucumber expansin.

The expansin-like proteins in the snail digestive track may be synthesized by the snails or by an endosymbiont living in the digestive system of the snail. Such symbionts might be bacteria, fungi, protists or some other microbe.

We assayed the effects of expansins on the mechanical properties of pure cellulose paper, which derives its strength principally from hydrogen bonding between cellulose microfibrils. Because paper is much simpler in composition and structure than plant cell walls, the action of expansins could be much easier to interpret. S1 protein showed clear effects on the mechanical properties of Whatman number 3 filter paper in both extensometer and stress relaxation assays. As our experiments show expansins are also able to disrupt slick paper (FIG. 7).

Expansins appeared to weaken cellulose paper in a manner different from that effected by cellulase. While both expansins and cellulase led to breakage of the paper in extensometer assays, only expansins showed a clear enhancement of stress relaxation in this material. Furthermore, incubations of paper with expansins did not lead to the release of reducing sugars, as was seen in incubations with cellulase. Because expansins did not hydrolyze the paper, and because hydrogen bonding accounts for the tensile strength of paper we conclude that expansins disrupt the hydrogen bonding between cellulose fibrils. Expansins probably do not catalyze cell wall loosening by disrupting hydrogen bonds directly between microfibrils, as these structures appear to be separated from one another by matrix polysaccharides which are thought to coat the outside of microfibrils in the wall. However, it is possible that they could induce wall extension by disrupting hydrogen bonding between the matrix polysaccharides and the microfibrils, thus reducing the resistance to movement of the microfibrils.

Stress relaxation assays performed to test the ability of the snail expansin-like protein to weaken the bonds in the paper indicate that this ability is attributed to all expansins and expansin-like proteins.

Expansins make cellulose more accessible to the degradative action of cellulases, thereby synergizing or enhancing the activity of cellulases. Cellulase activity can be measure in a number of ways including measuring the total amount of reducing sugars produced in the enzymatic reaction the cell. For other methods see Wood TM and KM Bhat 1988 Meth Enzymol 160:87–112. Expansins increase both the rate and total amount of degradation of cellulose. It is contemplated that this newly discovered effect of expansins can enhance the accessibility of cellulose for chemical, biochemical, or biophysical modification. Expansins in the presence of cellulase act synergistically to hydrolyze cellulose into smaller units.

Other methods of treatment or use of specific expansins, enzymes possessing expansin-like activity, or genetically modified organisms possessing expansin gene(s) or gene(s) that have expansin-like activity may modify cellulose by a number of various actions, including but not limited to chemical, biochemical, or biophysical activity. Such variations are anticipated to have numerous commercial utilities, which may include but not be limited to the following, the modification or alteration of cellulose in the production of commercial products or intermediates utilized in production of paper/pulp, textile, fodder, biomass alcohol, films, coatings, thickeners, agricultural and/or food applications. See M. E. Himmel et al., 1999 Curr Opin Biotechnol 10(4):358–364.

For commercial purposes, purified or crude expansin proteins could be added to cellulose preparations in processes and procedures where cellulose accessibility is a limiting factor or where alterations in cellulose surface glucans could give desirable properties or traits. Enhanced production of biofuels, ethanol or other low molecular weight substances from cellulose is a likely potential target for this application of expansin, whether by cellulase or some other enzyme system. Likewise, processes that chemically derivatize cellulose may be made more efficient by the application of expansin to cellulose. Expansin could be added in purified or unpurified form to the cellulose, or it could be engineered by standard methods to be expressed in plants or other organisms, which then might be added whole to the cellulose preparations, e.g. for biofuels production. Overexpression of expansins in plant tissues by standard methods would likely affect the properties of the cell walls and cellulose made by the plants, resulting in useful commercial properties such as greater accessibility to chemical reagents and enzymatic reagents and enhanced activity by cellulases. To overexpress expansin in plants, one could take the nucleotide sequence of either the full length cDNA or the corresponding gene and insert it by standard methods into a T-DNA plant expression vector in which expression of the expansin sequence would be driven by a strong promoter such as the constitutive cauliflower mosaic virus 35S promoter or an inducible promoter such as the PRI promoter or an endogenous plant promoter with selective expression in specific cell or organ types or under specific conditions, such as after hormone treatment or drought stress. The expression vector could be introduced into plants by biolistic transformation or by Agrobacterium-mediated transformation. Transformed plants would be screened for high expressers.

It is also possible to express these proteins in other recombinant protein expression systems for production of protein to be applied to cellulose, plant walls and related materials.

We know from previous work that expansins bind to cellulose and that they can disrupt hydrogen bonding between cellulose microfibrils (McQueen-Mason and Cosgrove, Plant Physiology 107: 87–100; Proc. Nat. Acad. Sci. 91:6574–6578). These new results show that expansins are also able to enhance cellulose degradation of the microfibril. The strong conclusion is that expansins can open up the microfibril to enzymatic attack by splitting off the individual polymers that make up the crystal and making them available to the cellulose. Because the glucan polymers that make up cellulose are held in the crystal by both hydrogen bonding and hydrophobic bonding, the results mean that expansins can disrupt both types of bonding. As additional research is performed, other methods of action may be discovered, which have potential commercial utility. However, it is understood that the disclosed embodiment is merely illustrative of the invention, which may be embodied in various forms. Accordingly, specific details disclosed herein are not to be interpreted as limiting, but merely as a support for the invention and as appropriate representation for teaching one skilled in the art to variously employ the present invention in any appropriate embodiment.

This invention suggests that the expansin proteins might find large scale use in processes for degrading or chemically modifying cellulose itself or altering the physico-chemical characteristics ofcellulosic materials. Moreover, by genetically engineering plants to express large quantities of expansins in their mature walls, it is likely that that cellulose in these walls will have altered physico-chemical properties and will be more accessible to chemical and enzymatic modification and attack. This might make such genetically engineered plants of greater use for paper/pulp, fodder, biomass alcohol production, or textiles and the other commercial applications cited above.

Alteration of the specific expansin, cellulase, and source and type of cellulose are within the scope of this invention. Such variation mayhave significant, commercial utility. These results may vary because of, but not limited to, the following factors: substrate specifications, solubilities, pH optima, and other biochemical and/or biophysical properties, but expansins in concert with cellulase will nonetheless enhance or synergistically impact cellulose degradation.

What we present here is a method using expansin(s), enzymes possessing expansin-like activity or genetically modified organisms possessing expansin gene(s) or genes that have expansin-like activity in the presence of a cellulase to modify cellulose by a number of various actions, including but not limited to chemical, biochemical, or biophysical activity.

It is noted that previous research has subjected expansins to a pH range from 3.0 to 8.0 and in the presence of a number of different buffers, such as sodium acetate, HEPES, EDTA, sodium bisulfitc, MES-NAOH, PBST and Tris-HCL. Variations ofreactant concentrations, buffer, and pH are possible and could be optimized for a given set of reaction conditions to facilitate the reaction. Obviously, extreme pHs, such as 1 or 14, would be inappropriate, since they would either denature the cellulose or expansin or inhibit the enzymatic reaction. The type of buffer to be used will depend upon the desired pH and other physiological considerations. The above listed buffers should be considered an example and not specifically limiting to this group.

FIG. 23 shows the cellulose degradation curve as measured by the release of sugars from the cellulose. It shows that the cellulose degradation curve of cellulase and expansin is very different from that of cellulase only, or of expansin only, and they do not have a superimposed relationship. This shows that cellulase and expansin have a synergistic effect in degrading or modifying cellulose. The recommended final concentration and type ofcellulase and of expansin will depend on the specific requirements of the reaction, e.g. in some cases 100 ug of Trichoderma cellulase and 50 ug of cucumber C3 expansin maybe adequate but much higher and lower concentrations and different ratios and types of cellulase and of expansin may be prescribed and are within the teaching of this invention.

The length of reaction time to effect the desired alteration of substrate may be altered and such time variation is anticipated. Conversely, variations of the type and concentration of expansin and of cellulase along with the specific physiological conditions will affect the rate of reaction.

In summary, cucumber expansins appear to associate with the cellulose fraction of the cell wall. They do not exhibit polysaccharide hydrolysis under a number of assay conditions and they do not cause a progressive weakening of the wall. Expansins also appear to disrupt hydrogen bonds in cellulose paper.

Isolation of new enzymes often opens new possibilities of application of same. Although the potential application in paper industry have been emphasized in this disclosure, numerous other directions of use can be imagined. For example expansins could be used for processing of polysaccharides for control of physical properties. Hydrogen bonding is an important determinant of many physical properties of commercial products containing polysaccharides. Expansins may be incorporated into the polysaccharide products to modify hydrogen bonding and thereby modify the physical characteristics of the products. Examples include control of the viscosity and texture of polysaccharide thickeners used in foods and chemical products, control of stiffness and texture of paper products; and control of mechanical strength (e.g. tear strength) of paper products.

The present invention is believed broadly applicable to alteration of various physical properties of polysaccharides. While plant polysaccharides represent a preferred embodiment of the invention, expansins of the invention are believed useful catalytic proteins for the treatment polysaccharides from a variety of sources (i.e., synthetic, bacterial or other microbial system, etc.). While it is reasonable to make a strong claim that expansins primarily operate by disruption of hydrogen bonds, the invention is not necessarily limited to this mode of action. Results concerning altered physical properties of polysaccharides are nonetheless produced by use of the novel expansins of the invention.

Expansins may be used for de-inking paper, which is a significant limitation in current paper recycling operations. In this application, expansins may help loosen the bonding between surface polymers, which are stuck to the ink, and the remainder of the cellulose fibers. Also, in the paper industry expansins may prove useful for large scale paper dissolution, or perhaps for alteration of the mechanical properties of dry paper. Treatment of dry paper could produce paper with novel properties.

Expansins maybe used in combination with other chemicals or enzymes to improve various processes. For example, a major limitation in ethanol production from biomass is the degradation of cellulose. Expansins in concert with cellulase may act synergistically in the breakdown of cellulose. If expansins help cellulases gain access to glucan chains that make up microfibrils, then they could speed cellulase action. Also, delignification is a major problem in industrial uses of many plant fibers. To solve this concern, expansins may be used with lignases (peroxidases) for synergistically de-lignifying plant fibers. Expansins may also be useful in various bioremediation applications, either above or in combination with other biological or chemical materials.

Expansins have been found in cotton fibers and are probably found in native cell walls, but are likely not to be present in processed cotton fiber walls. Accordingly, expansins may be useful to the textile industry by virtue of alteration of either the wet or dry mechanical properties of cotton flax, or other natural fibers.

It is known that certain fungal cell walls (i.e., Phycomnyces) bear chemical resemblance to the structure of plant cell walls. Also, certain insects have chitin structures or walls (i.e., Manduca cuticle) that resemble fungal walls in some of their biochemistry. Expansins may modify chitin properties. Accordingly, expansins may be useful for insect control or as anti-fungal agents, either alone or in combination with other insecticidal or fungicidal agents.

A further use of expansins could be for altering the mechanical strength of gels or otherwise affecting the gelling or other properties of gels (i.e., gelatin, gellum-gum/phytagel, agar, aarose, etc.). Such material are useful agents in foods, cosmetics, and other similar materials. Since hydrogen bonding is important for such gels and in view of the belief that expansins alter hydrogen bonding of wall glycons, expansins may alter the gelling properties of various gels.

An additional use of expansins may involve alteration of aggregation of hemicelluloseA and solubilized cellulose. In the event that expansins appropriately affect such aggregation, they may prove useful for industrial processes involving these materials, including cellulose processing and film making.

Isolation of a novel protein allows one to attempt the cloning of the gene coding for this protein using the standard approach of establishing amono acids sequence of a fragment of the protein and designing oligonucleotides to screen the cDNA library. When cloned, the gene for one or more expansins will need to be expressed in a bacterial or other system to obtain sufficient quantities for the commercial usefulness of the ideas listed above. Cloning will also be a necessary first step for the commercial uses requiring genetic manipulation of the protein in transgenic plants.

Engineering of plant cell growth for agricultural uses can become reality. We have evidence that expansins arc important for endogenous growth of plant cells. One can envision several commercial applications of expansins. One such application includes increase of the growth of specific organs and tissues by selective enhanced expression of expansins during plant development. Control of selective expression would be by any means such as application of specific chemicals that promote transcription of expansins or by insertion into the genome of plants specific artificial genetic constructs (i.e. appropriate promoters, enhancers, structural genes and associated elements) to effect organ-specific, tissue-specific, and/or chemical-specific enhancement of expression of the introduced or endogenous genes for the expansin proteins. Examples of use might include enhancement of fruit production (grapes, citrus fruits, etc.), enhancement of leaf growth (lettuce, spinach, cabbage), enhancement of stem or petiole growth (sugarcane, celery, flower stalks), and enhancement of root growth. Tissues engineered to grow by expression of expansins might have enhanced desirable traits (size, succulence, texture, durability).

Another direction of controlled growth would include decrease of the growth of specific organs and tissue by reducing the expression or effectiveness of endogenous expansins. The control of expression would be by any means such as application of specific chemicals that reduce transcription of expansins or by insertion of antisense genetic constructs that reduce mRNA levels of endogenous expansin genes, or by manipulation of the genetic control elements that regulate expression of endogenous expansin genes. Examples of such use might include dwarfing of stems for enhanced mechanical stability and genetic pruning, stunting, or elimination of undesirable plant organs.

Similar approach could be utilized to control the cell size in plant cell tissue or cell cultures used in bioreactors or for production of useful chemical agents. Control might be effected by addition of exogenous expansins or inhibitors of expansin action, by genetic regulation of endogenous expansin genes and their products, or by regulation of artificially inserted genes for expansin proteins, for antisense constructs against endogenous expansin mRNAs, or for proteins that regulate or modify expansin action.

The present invention may be readily understood by considering the following examples illustrative of specific embodiments. The Examples are given to serve as a guide in carrying out the invention and are not to be construed as a limitation or limitations of the invention. It will be understood that various changes or modifications may be made, as will be apparent to those skilled in the art, without departing from the spirit of the invention or the scope of the claims annexed hereto.

EXAMPLE 1

Preparation of Plant Materials

Seeds of cucumber (*Cucuinis sativus* cv Burpee Pickler) were sown on Seed Germination Kimpack Paper K-22 (Seedburro Equipment Corporation, Chicago, Ill.) soaked with distilled water, in flats, 50×25×6 cm, with lids of the same dimensions. Seedlings were grown in the dark for 4 days at 27° C. The apical 3 cm of hypocotyl was excised and frozen at −20° C. for no more than 5 days and prepared for creep measurements as previously described (Cosgrove 1989). For bulk wall extractions, the apical 3-cm hypocotyl regions were collected on ice water and homogenized with 25 mM sodium acetate, 2 mM EDTA, pH 4.5 in a Waring blender. The wall fragments were collected and washed twice by filtration through Miracloth and subsequently used for protein extraction. Basal walls were from the lower 6 cm of the (15 cm long) hypocotyls.

Oat seedlings were grown in moist vermiculite in complete darkness at 27° C. Except as noted, coleoptiles were from 4-day old oat seedlings (*Avena sativus* L. cv. Olge, from Carolina Biological Supply, Burlington, N.C., USA).

Seedlings were quickly harvested under room lights. For wall extension assays, the apical 2 cm region of the growing stem or coleoptile was excised, sealed in aluminum foil and frozen at −20° C. prior to use. Coleoptiles were separated from primary leaves. Cuticles were abraded by rubbing the coleoptiles or stems between two fingers coated with a slurry of carborundum (320 grit, well washed prior to use; Fisher Scientific, Fair Lawn, N.J.). For oat coleoptiles, the cuticle was generally abraded prior to freezing, whereas for cucumber and pea stems the frozen segment was quickly abraded.

In some instances as noted, coleoptile cuticles were removed by stripping the epidermis from the tissue with fine forceps and the remaining coleoptile cylinder was bisected longitudinally prior to freezing. Tissues were thawed, pressed under weight for 5–10 min to remove tissue fluids and clamped in an extensometer (5 mm between the clamps, corresponding to the apical 3–8 mm of the stem or coleoptile).

Seeds of pea (*Pisurn sativum* cv Alaska), radish (*Raphaizus sativus* cv Crimson Giant), tomato (*Lycopersicon esculentitm* cv Rutgers), onion (*Alium cepa* cv Snow White), maize (*Zea mays* cv B73×Mol7), and barley (*Hordeumn sativuni* cv Barsoy) were sown on vermiculite wetted with distilled water and grown for 4 days in the dark at 27° C. Hypocotyls of pea, radish and tomato; primary leaves of onion; and coleoptiles of maize and barley were excised and frozen for subsequent extension experiments. Young growing leaves of zephyr lily (*Zephyranthes candida*) were removed from a greenhouse-grown colony of plants which were kept in the dark at 27° C. for 12 hr prior to harvest, and frozen for later extension assay.

EXAMPLE 2

Isolation of expansins cEx-29 and cEx-30 from cucumber

Protein Extraction

Washed cucumber cell wall fragments (from 150–200 g of tissue) were extracted overnight in 20 mM Hepes, pH 6.8, 1 M NaCl at 4° C. Cell wall fragments were filtered on Miracloth and the salt-solubilized fraction precipitated with ammonium sulfate (the activity precipitated between 20 and 60% saturation with $[NH_4]_2SO_4$). The precipitate was desalted on a 7-mL column of Bio-Gel P2 (Bio-Rad Laboratories) into 50 mM sodium acetate, pH 4.5. Protein concentration was 2 to 4 mg/mL, estimated by Coomassie Protein Assay Reagent (Pierce, Rockford, Ill.).

For the comparison of soluble and wall associated proteins, 100 g of tissue was harvested and homogenized with 100 mL of 25 mM sodium acetate, pH 4.5, 1 mM EDTA. Wall fragments were filtered out and the remaining solution designated as the soluble fraction. Wall fragments were cleaned as described above, and then extracted in 200 mL of 20 mM Hepes, pH 6.8, 1 M NaCl for one hour at 4° C. Aliquots of both solutions were dialyzed against 50 mM sodium acetate pH 4.5 and tested for reconstitution activity, as described below.

Protein Fractionation

The 20 to 60% $(NH_4)_2SO_4$ precipitate pellet was resuspended in 2 mL of distilled water and insoluble material was removed by centrifugation and filtration through a Centricon 30 microconcentrator (Amicon, Beverly, Mass.) prior to being loaded onto a C3 hydrophobic interactions column (ISCO C-3/6.5 m 10×250 mm) equilibrated with 50 mM sodium acetate, pH 4.5, 20% (saturation) (NH4)2S04. Proteins were eluted from the column with a linear gradient from the equilibration buffer into 50 mM sodium acetate, pH 4.5, in 35 min. at a flow rate of I mL/min. Fractions were desalted on a 7-mL column of Bio-Gel P-2 (Bio-Rad Laboratories, Richmond, Calif.) into 50 mM sodium acetate and assayed for their ability to reconstitute extension to inactivated cucumber hypocotyl sections.

The active fractions from the C3 column were pooled and subsequently desalted and concentrated on a Centricon 30 microconcentrator (Amicon, Beverly, Mass.), the buffer being exchanged for 15 mM Mes NaOH, pH 6.5. The concentrated sample was then loaded (in a volume of 1.7 mL) onto a sulfopropyl cation exchange column (Bio-Rad HRLC MA7S 50×7.8 mm) equilibrated with 15 mM Mes NaOH, pH 6.5, and proteins eluted with an ascending gradient of NaCl (from 0 to 1.0 M over 45 min) in the same buffer at a flow rate of 1 mL/min. $A_{280}$ nm of eluting proteins was measured using a Dionex Variable Wavelength Detector (VDM-2).

Active fractions from ammonium sulfate precipitation, C3 column and sulfopropyl fractions S1 and S2 were concentrated, desalted on Centricon 30 Microconcentrators, and then run on SDS-polyacrylamide gels, according to the method of Laemmli. Gels were subsequently stained with Coomassie Brilliant Blue P250. Fractionation by this procedure was repeated more than 10 times with similar results. Results are presented in FIG. 2.

EXAMPLE 3

Isolation of expansins oEx-29 from oat

Protein Extraction.

For oat protein extraction, oat seedlings were rapidly cut under room lights and placed in ice water. The apical 2.5 cm (+/−0.5 cm) of each coleoptile was then cut, separated from the primary leaf, and placed on ice while the other coleoptiles were harvested. About 500 coleoptiles were homogenized in 200 mL of 10 mM sodium phosphate, pH 6.0. In some instances the coleoptiles were collected in lots of 100–200 and frozen (−20° C.) for 1 to 3 d prior to homogenization. The homogenate was filtered through a nylon screen (70 mm mesh), and the cell walls were collected and washed 4 times by resuspending in the homogenization buffer (300 mL) followed by filtration. lonically-bound proteins were extracted for at least 1 hour at 4° C. with 50 mL of 1 M NaCl containing 20 mM Hepes (pH 6.8), 2 mM EDTA and 3 mM sodium metabisulfite. Wall fragments were removed by filtration or centrifugation and the wall proteins in the supernatant were precipitated with ammonium sulfate (0.4 g added to each mL). Precipitated proteins were dissolved in 1.5 mL of water and desalted on an Econo-Pac 10 DG desalting column (BIO-RAD Laboratories, Richmond, Calif., USA) which was equilibrated with 20 mM Tris-HCI, pH 8.0, containing 100 mM NaCl. Without NaCl the active proteins tended to bind to the desalting column, resulting in a lower recovery.

Protein Fractionation.

Protein solution from the desalting column was centrifuged in a microcentrifuge for 3 min to remove precipitates. Proteins were then loaded onto a DEAE-column (Sephadex A-25, Sigma) equilibrated with 20 mM Tris-HCI, pH 8.0, containing 100 mM NaCl at 25° C. The proteins bound to the DEAE-column were eluted by 1 M NaCl in 20 mM Tris-HCI buffer, pH 8.0.

A 1-mL Concanavalin A column (Sigma) was equilibrated with 200 mM NaCl containing 1 mM each of $Mg^{+2}$, $Ca^{+2}$, and $Mn^{+2}$. Proteins from the DEAE-column were passed through this column. After the column was washed extensively with the same solution, the bound proteins were eluted with the same solution containing 0.5 M a-methyl manoside. Extension activity was associated with the fractions that did not bind to the column.

Active fractions were further separated by HPLC using a carboxymethyl (CM) cation exchange column (4.6×250 mm, CM300/6.5 mm, ISCO, Nebraska) equilibrated with 10 mM Mes, pH 5.5. Before the protein sample (1 mL) was loaded on the column, the sample buffer was exchanged for 10 mM MES, pH 5.5, by use of a 30-kD Centricon microconcentrator (Amicon, Berverly, Mass., USA). Proteins were eluted from the CM column at a flow rate of 1 mL/min with a gradient of 0 to 0%, 0 to 4%, 4 to 6% and 6 to 100% of 1.0 M NaCl in 10 mM MES, pH 5.5, from 0 to 5 min, 5 to 10 min, 10 to 30 min and 30 to 50 min, respectively, and detected by absorbance at 280 nm.

Proteins were quantified colorimetrically using the Coomasie Protein Assay Reagent (Pierce, Rockford, Ill., USA). For SDS-PAGE (Laemmli 1970), proteins were separated on a 14% polyacrylamide gel or a 4–20% gradient polyacrylamide gel (Bio-Rad Ready Gel, Richmond, Calif., USA). For Western analysis, proteins were electrophoretically transferred to a nitrocellulose membrane in a solution of 192 mM glycine, 25 mM Tris, 20% methanol (v/v) at 10 volt/cm for 3 h or in some cases 16 h. After the membrane was blocked with 3% bovine serum albumin in phosphate buffered saline containing 0.05% Tween-20 (PBST), it was incubated for 2 hr in PBST containing antiserum (1:3000 dilution). The membrane was washed 4 times with PBST and then incubated for 1 h with goat anti-rabbit IgG-conjugated alkaline phosphatase (Sigma; dilution of 1:4000) in PBST. The Western blot was developed usingbromochloroindolyl phosphate/nitro blue tetrazolium and the reaction was stopped with 10 mM EDTA.

Table I. Purification of oat Ex29 from etiolated oat coleoptiles. Activity was assayed as described in FIG. 4 and expressed as the initial increase in the extension rate of isolated cucumber cell walls upon addition of the protein fraction (e.g. 5 to 30 min after protein addition). Total activity was calculated by dividing the activity (measured in 1–3 extension assays) by the fraction of protein used for each assay. Specific activity was calculated by dividing the total activity by the total protein.

| Purification step | Total protein (μg) | Total activity units (μm/min) | Specific activity (units/mg protein) | Purification (fold) | Yield (%) |
|---|---|---|---|---|---|
| $(NH_4)_2SO_4$ precipitation | 444 | 123 | 278 | 1 | 100 |
| DEAE | 190 | 104 | 546 | 2 | 84 |
| CM-HPLC | 6 | 85 | 14278 | 51 | 69 |

Soluble protoplasmic proteins were obtained by homogenizing oat coleoptiles in 10 mM sodium phosphate buffer (in some cases, 10 mM Hepes, pH 6.8) and centrifuging at 4° C. at 26,000 g for 10 min to remove particulate matter.

EXAMPLE 4

Preparation of expansin-like proteins from snails and snail feces.

Acetone powders of the visceral humps of *Helix pometia* were purchased from Sigma Chemical Company. Live snails (*Helix aspersa*) were purchased from NASCO. Protein solution was made by dissolving snail acetone powder (10 mg/ml) in 50 mM sodium acetate buffer, pH 4.5. Feces of *Helix aspersa* were dissolved in the same buffer.

EXAMPLE 5

Extension Measurements

Extension measurements were performed using a constant load extensometer as described by Cosgrove (1989). Briefly, frozen/thawed tissues were abraded for a short time with carborundum to disrupt the cuticle, boiled in water for 15 sec (for reconstitution assays), and secured between two clamps (with about 5 mm between the clamps) under a constant tension of 20 g force (for assays with radish, tomato and onion tissues the tension was reduced to 10 g). Plastic cuvettes were fitted around the walls and filled with bathing solution. For reconstitution assays the bathing solution was first 50 mM sodium-acetate pH 4.5 for 30 min., followed by the protein fraction to be assayed in the same, or equivalent pH buffer. Movement of the lower clamp was detected with a position transducer and recorded on a microcomputer. All extension assays reported here were repeated at least five times, except for the heterologous reconstitutions (e.g. with walls from pea, tomato and corn), which were performed three to five times.

Cucumber expatisins activity,

Extension induced by cucumber expansins is presented in FIGS. 1, 11, 12.

Oat expansiins activity.

Extension induced by oat expansin is presented in FIG. 11 and 12.

Snails expansins activity.

Extension induced by snail expansin-like proteins are presented in FIGS. 18 and 19. The experiment was performed as described for cucumber and oat proteins.

The protein solution obtained from snail acetone powder by dissolving snail acetone powder (10 mg/mL) into 50 mM sodium acetate, pH 4.5, is capable of inducing extension of isolated cucumber walls.

EXAMPLE 6

Effects of DTT and Metal Ions on endogenous acid induced wall extension

Figure 4A:
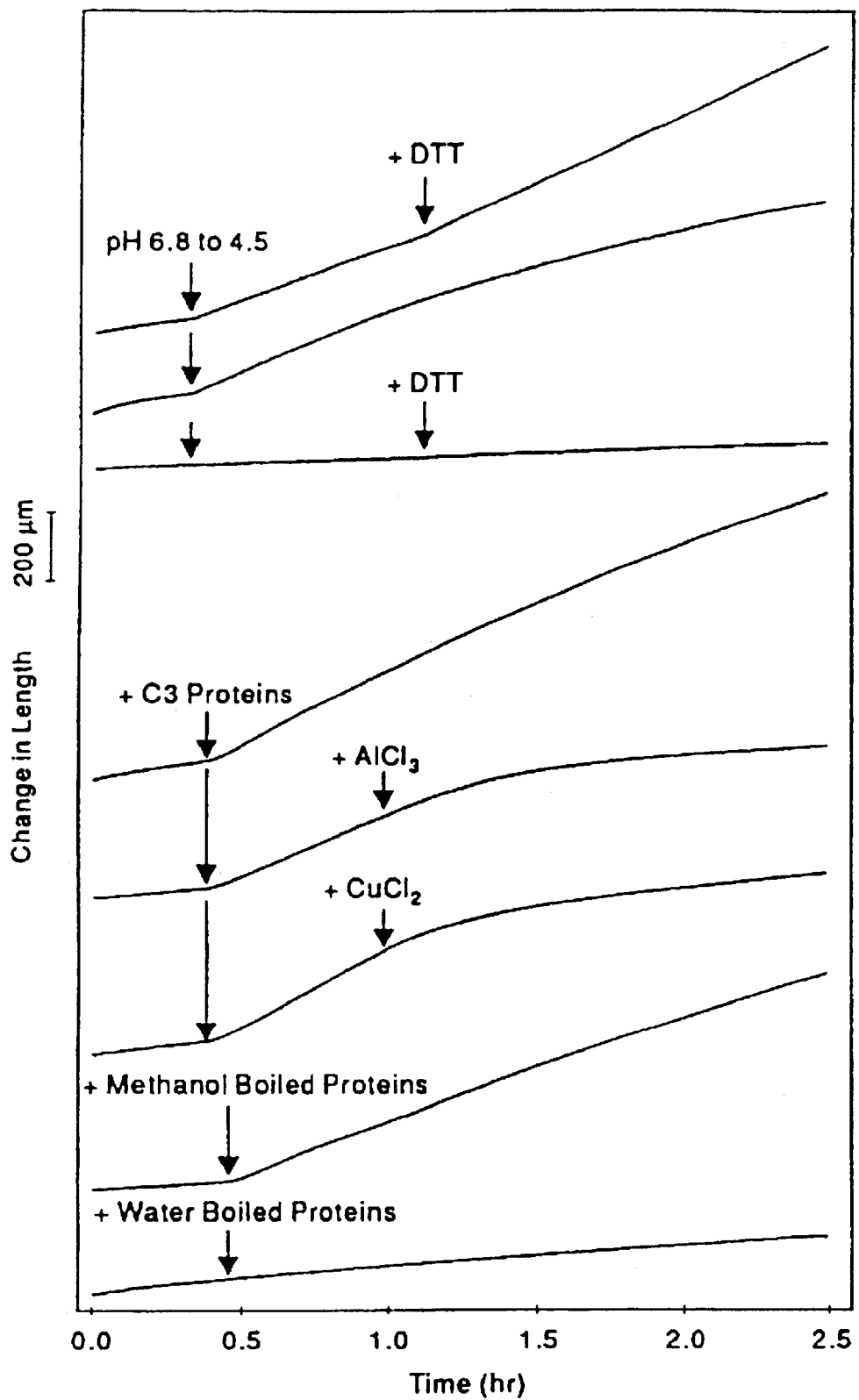
Figure 4B:
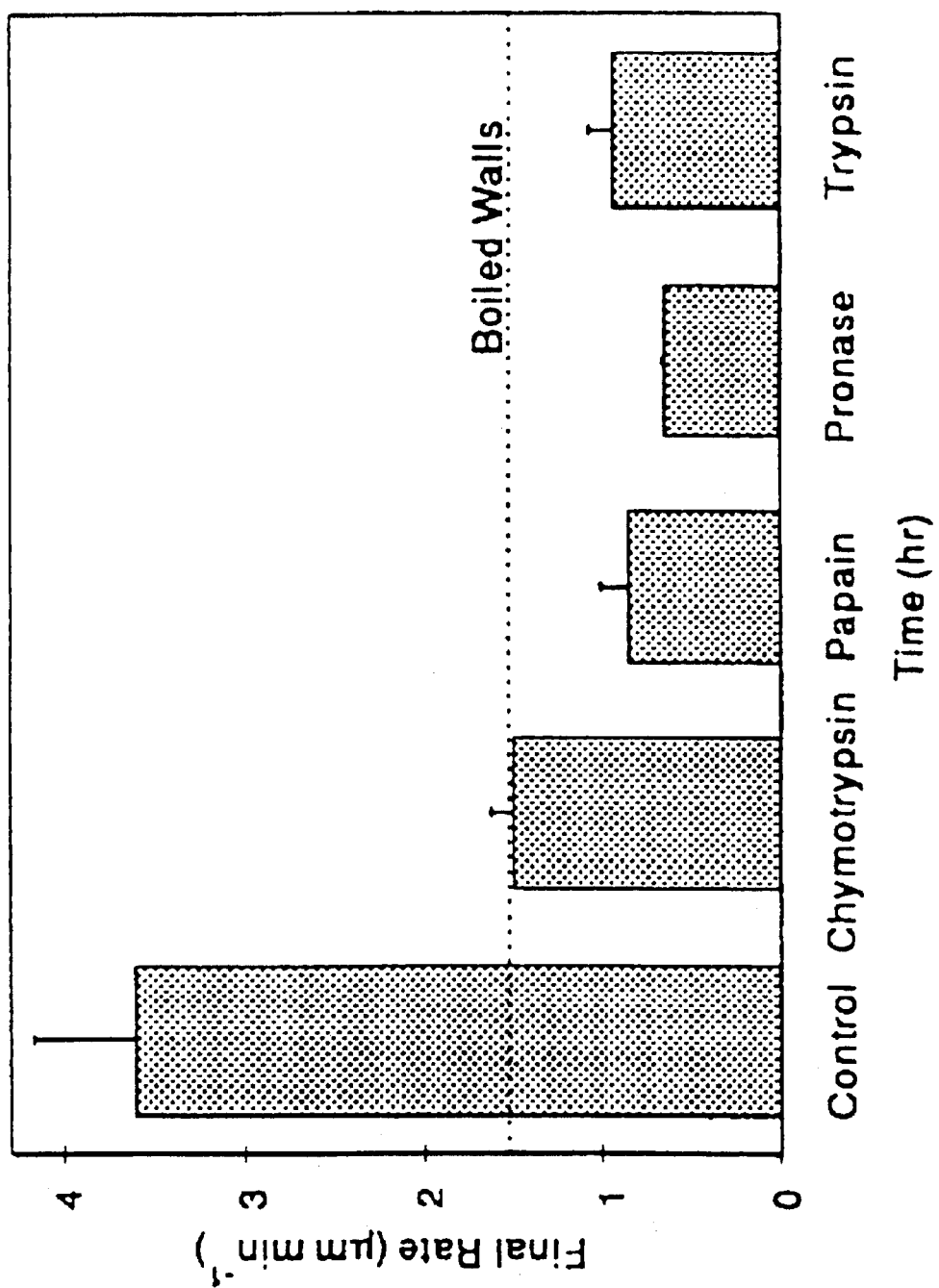

Endogenous acid-induced extension was previously shown to be sensitive to a number of exogenously applied factors (Cosgrove D. J., Planta vol. 177, pp 121–130, 1989). The thiol reducing compound dithiothreitol (DTT) was shown to stabilize or even enhance the extension of isolated cucumber cell walls at acid pH. To see if this was a characteristic of our extension inducing proteins, we first reconstituted wall specimens with an active C3 fraction from cucumber, as shown in FIG. 4a, stems were allowed to extend for one hour at which point sufficient DTT was applied to bring the bathing solution to 10 mM. Almost immediately the rate of extension is increased and thereafter remained constant, whilst reconstituted sections without the addition of DTT typically show a gradual decline in the rate of extension.

In contrast heavy metal ions including copper and aluminum were shown to be strongly inhibitory to endogenous acid-induced extension (Cosgrove 1989). Again, in FIG. 4a, boiled stem tissue reconstituted with C3 proteins showed very clearly the same sensitivity to an application of these ions, the rates of extension falling rapidly to the rate seen in the inactivated tissue before reconstitution.

EXAMPLE 7

Effects of Boiling in Methanol or Water on the activity of cucumber expansins

An unusual property of the endogenous cell wall extension activity is its ability to survive boiling in methanol (Cosgrove, 1989). We found that methanol-boiled walls retained extractable activity, whereas extracts from cucumber tissues boiled in water do not exhibit this activity, shown in FIG. 4a. Fractionation of the active extract from methanol boiled walls by the methods given above showed it to contain the 29- and 30-kD proteins in the S1 and S2 fractions (data not shown). The ability of the activity to survive boiling methanol may be due to the small size of these proteins and to protection within their carbohydrate-rich sites within the cell wall.

Protein concentrations were estimated using Coomassie Protein Assay Reagent (Pierce, Rockford, Ill.) using a standard curve constructed using BSA (Pierce). Wall specimens inactivated by boiling were preincubated with S1 and S2 proteins at estimated concentrations of micrograms per mL and then extended in the extensiometer, as described above, in 50 mM sodium acetate pH 4.5. After 1 hr enough dithiothreitol (DTT), from a 100 mM stock, was added to bring the bathing solution to 10 mM DTT.

To study the effect of heavy metal ions wall specimens were extended initially in 50 mM sodium acetate, pH 4.5. After 20 minutes the bathing solution was exchanged for one containing an estimated 50 micrograms of active C3 proteins. One hour after the start of the experiment $AlCl_3.6H_2O$ or $CuCl_2.2H_2O$, from 100 mM stocks, were supplied to give a final concentration of 1 mM.

For both treatments 100 g (fresh weight) of apical tissue was harvested and either boiled for 30 seconds in 1 L of distilled water, or for three minutes in 1 L of Methanol. Methanol boiled tissue was allowed to dry before being resuspended in 50 mM sodium acetate, pH 4.5. Both sets of tissue were then homogenized, cleaned and salt extracted, as described above. Salt extracts were precipitated with $(NH_4)_2SO_4$, resuspended and desalted, and tested forreconstitution activity as described above.

EXAMPLE 8

Effect of Protease Treatments on the activity of cucumber expansins

Cosgrove (1989) also showed that endogenous wall extension was eliminated by incubation with proteases, one of the initial clues that extension was catalyzed by proteins. The proteinaceous nature of our extension inducing factors was indicated by the sensitivity of reconstituted extension to protease incubations. This data is presented in FIG. 4b; 4-hr incubations with chymotrypsin, papain, pronase and trypsin all reduced extension to rates seen in inactivated tissues.

Inactivated stem sections were incubated with active C3 proteins, at an estimated concentration of 50 micrograms per mL, for 30 min at 25° C. Reconstituted stems were then incubated with 1000 units of trypsin or 1000 units of chymotrypsin in 50 mM Hepes-NaOH, pH 7.3 for 4 hr at 30° C., and with pronase (2 mg/mL), or papain (2 mg/mL) in 50 mM sodium acetate, pH 5.0, 1 mM DTT for 4 hr at 30° C. For a control C3 proteins were incubated at 30° C. for 4 hr without the addition of proteases. After incubation the stem sections were assayed for extension, initially in 50 mM Hepes, pH 6.8, after 30 min the buffer was switched to 50 mM sodium acetate, pH 4.5. The difference in the rates of extension (pH 4.5–pH 5.5) was calculated. All experiments were repeated four times.

EXAMPLE 9

Effects of pH on Reconstituted Extension Induced by Cucumber Expansins

Reconstitution experiments were carried out at arrange of values of pH, results presented in FIG. 5 show that there is little or no induction of wall extension by the C3 proteins until between pH 5.5 and pH 5.0 and that extension activity has a maximum some where between pH 4.5 and pH 3.5. The region of highest response to changes in pH lies in the range pH 5.5 and pH 4.5, these values are within the range of apoplastic pH values reported in elongating tissues, and supports the possibility that these proteins could play an important role in the acid-growth response.

Buffers in the range pH 3.0 to pH 6.5 were prepared by titrating 50 mM citric acid with 1 M $K_2HPO_4$ Inactivated stem sections were suspended in the extensiometer in buffer of appropriate pH. After 30 min of extension the bathing solution was replaced by a 1:1 dilution of C3 proteins (estimated final concentration 50 micrograms per mL) with the appropriate buffer, where necessary the pH was adjusted using either 1 M citric acid or 1 M $K_2HPO_4$. Change in rate of extension was calculated as the difference in extension rates before and after addition of proteins. All experiments were repeated eight times.

EXAMPLE 10

Effects of Cucumber Expansins on Cellulose Filter Paper

Strips of Whatman number 3 filter paper (Whatman Lab sales, Hillsboro Oreg.) (2 mm by 10 mm) were cut and were clamped in the constant load extensometer as described for cucumber hypocotyl sections. Extension was measured in 50 mM sodium acetate and in the same buffer containing protein fractions. Additionally, effect of expansins on the lost of mechanical strength of paper was measured by stess relaxation assay. For stress relaxation measurements, the paper was incubated in various pretreatment solutions and assayed while still wet, in the standard method.

In extensometer assays S1 protein induced a brief period of extension prior to rapid breakage of the paper, an effect not seen in incubations with buffer alone or with boiled protein. Incubations of paper strips with cellulase showed a similar effect. However, it required at least 100 mg of cellulase to weaken the paper sufficiently to be detected in this assay, whereas only 5 mg of S1 protein produced similar effects. In parallel experiments, cellulase (100 mg/mL) was shown to release 25 mmol reducing equivalents per mL during a five h incubation with Whatman No.3 paper. In contrast, no sugar release was detectable in similar assays using S1 and S2 protein (both 5 mg/mL). The results are presented in FIG. 6.

S1 protein (5 mg/mL) caused a marked increase in the relaxation rate of paper strips, while cellulase (100 mg/mL) had almost no affect. In both extensometer assays and stress relaxation tests, S1 protein which had been boiled for two minutes did not induce the effects apparent with native S1 proteins, indicating that the effects were associated with the activity of the protein. Similar results were obtained in assays with S2 proteins (data not shown).

These data indicate that expansins substantially weaken cellulose paper in a manner which does not involve the hydrolysis of cellulose. Since the structural integrity of cellulose paper appears to result from hydrogen bonding between cellulose fibrils, it seems likely that these proteins weaken paper by disrupting these associations.

EXAMPLE 11

Effect of Cucumber Expansins on Slick Paper

In order to test whether a protein preparation containing cucumber expansins can disrupt slick paper, in a similar fashion as it acts on pure cellulose paper the following experiments were conducted. Slick paper was obtained from three sources: (a) the pages of "Nature" magazine (unprinted margins were used), (b) a commercial catalog for chromatography equipment (c) a colored advertising insert (Hills) in the Sunday paper. Paper strips of 2–3 mm width were cut and hung in our extensometer, such that a 5-mm long strip was put under 20 µg force. The buffer contained 50 mM sodium acetate, pH 4.5 with or without added C3 protein (about 20 µg per paper strip was used). The length of the paper strips was recorded for up to 5 h. Four samples of each paper were used with each treatment (+/−protein). The untreated (control) paper showed very little change in length, and maintained its mechanical strength throughout the test period. In contrast, the treated papers began to extend and quickly broke once extension began. The time for breakage after addition of protein varied from 45 min to 2.5 h, but all samples broke. FIG. 7 illustrates the typical extension.

EXAMPLE 12

Effect of snail expansin-like proteins on Cellulose Paper.

A stress relaxation assay was performed as described in Example 10. Increased relaxation in time domaines of 10–100 msec (faster relaxation in comparison with controls) proved the ability of snail expansin-like proteins to weaken the mechanical strength of paper.

EXAMPLE 13

Preparation of antibodies to cucumber expansin cEx-29

Antiserum with specific recognition of this protein was raised in a female New Zealand White rabbit (Li and Cosgrove, in preparation) by subcutaneous injections of cucumber Ex29 with Freund's adjuvants (Harlow and Lane 1988). Serum dilutions in the range of 2000:1 to 4000:1 proved optimal for Western analyses of cucumber and oat proteins.

EXAMPLE 14

Western blot analysis of immunoreactivity between cucumber and oat expansins

We performed western analysis of oat coleoptile proteins probed with antiserum against cucumber Ex29. Results are presented in FIG. 17. Comparison of lane 1 (crude wall protein) with lane 2 (crude protoplasmic protein) shows that the antiserum recognizes an Ex29-like protein (arrow) specifically bound to the coleoptile cell wall. Comparison of lane 3 (crude wall protein) with lane 4 (purified protein with extension activity) shows that the Ex29-like protein co-purifies with the extension activity. Lane 1 was loaded with 15 µg of crude wall protein (ammonium sulfae precipitate of 1 M NaCl extract). Lane 2 had 15 µg of the soluble protoplasmic protein fraction. These samples were separated on the same 4–20% gradient SDS polyacrylamide gel, blotted onto nitrocellulose, and probed with rabbit antiserum against cucumber Ex29. Lane 3 was loaded with 0.2 µg of crude wall protein and Lane 4 had 0.2 µg of active oat wall-extension protein purified sequentially by DEAE Sephadex and CM-HPLC. These samples (3–4) were separated on the same 14% SDS polyacrylamide gel, blotted onto nitrocellulose, and probed with antiserum. This assay, with minor variations, was carried out four times with similar results.

EXAMPLE 15

Western blott analysis of immunoreactivity between expansin-like protein from snail and cucumber expansin cEx-29.

FIG. 20 presents a Western blot of active HPLC-separated protein fractions from snail acetone powder, probed with antibody PA 1 which was raised against cucumber expansin-29. The active fractions show a striking band at about 26 kD, which is similar to (though slightly smaller than) cucumber expansin-29. This results provide strong evidence that the wall extension activity found in the snail acetone powder is due to a protein with similar antigenic determinants as cucumber expansin-29.

FIG. 21 presents a Western blot of the proteins from *Helix aspersa* feces. probed with the antibody PA-1. The single band indicates the presence of an protein antigenically similar to cucumber expansin-29.

EXAMPLE 16

Effects of Urea on Plant Cell Wall Extension

This example show the effects of 2 M urea on native cell walls, walls reconstituted with expansin, and heat inactivated walls. Native cell walls or heat-inactivated cell walls from cucumber hypocotylcs were obtained as earlier described and clamped in the extensometer in 50 mM sodium acetate at pH 4.5. At about 20 minutes, an S1 fraction of cucumber expansin (10 µg/ml) was added to one set of heat-inactivated walls. At about 45 minutes the incubation solutions were replaced with 2 M urea buffered with 50 mM sodium actetate, pH 4.5. The aforesaid solution also contained 2 mM dithiothreitol to stabilize the expansin activity. Results of this experiment are presented in FIG. 22. Data are representative of four (4) trials for each respective treatment. The dotted line of FIG. 22 represents native cucumber cell walls.

These data show that 2 mM urea acts synergistically with expansins to enhance the extension rate of native cucumber cell walls and heat-inactivated cell walls reconstituted with purified expansins. As indicated in the trace labeled "heat-inactivated" in FIG. 22 urea alone (without active expansins in the cell walls) has little effect.

These results support the contention expansins disrupt hydrogen bonding between cell wall polymers.

EXAMPLE 17

Identification of Expansins in Various Plant Materials

Using the methods earlier described herein for extraction of expansins from cucumber and oat materials, quantities of the following plant materials were treated:

(i) broccoli flower stalks (*Brassica oleracea italica*);
(ii) celery peticles (*Apium graveolens*):
(iii) tomato leaves (*Lycopersicum esculenlum*);
(iv) cotton fibers (Gossypium); and
(v) corn coleoptiles (*Zea mays*).

Expansins were identified and confirmed by use of the antibody assay described herein (having common antigenic epitomes with the antibody against ex29), and the extension activity analysis described herein.

EXAMPLE 18

Use of Alpha- and Beta-expansins to enhance the accessibility of cellulose to cellulase and related enzymes and processes.

To test whether expansins can modify cellulose or "open up" the cellulose crystal and make it more available to degradation by cellulase, a microcrystalline form of cellulose (Avicel) was incubated in the following solutions:
1. pure buffer,
2. buffer+expansin,
3. cellulase, or
4. expansin+cellulase 50 mg of Avicell (microcrystalline cellulose type PH101, FMF Corp) was placed in 1 mL buffer (mM sodium acetate, pH 4.5) with expansin alone ("C3" fraction, about 50 µg per mL), or cellulase alone (100 µg of Trichoderma cellulase from Boehringer, purified to remove sugars), or expansin plus cellulase (50 µg C3 expansin and 100 µg Trichoderma cellulase). After 1 h and 2 h, aliquots were removed and assayed for total reducing sugar concentration, as a means of measuring cellulose breakdown. This experiment was carried out twice with nearly identical results.

The release of sugars from the cellulose was assayed as a measure of cellulose degradation. The results as shown in FIG. 23 indicate that expansins by themselves do not release sugars, but they enhance the effectiveness of cellulase by 50%. These results provide an initial example of expansin's synergistic effect with cellulase on cellulose.

Avicel was also treated with buffer solutions containing cellulase, with or without addition of purified beta-expansin from maize pollen ("Zea m 1") and alpha-expansin from cucumber hypocotyl walls. Purification of beta-expansins is described in Cosgrove, D J et al., *Proc. Natl. Acad. Sci. USA*, 1997, 94:6559–6564. Extraction of cucumber expansin is described in the previous examples.

Briefly, the Zea m 1 expansin was obtained in active, pure form from maize pollen as follows: Ten g of pollen was mixed with 100 mL 50 mM sodium acetate buffer, adjusted to pH 4.,5, and stirred either at room temperature or at 4° C. for 1 h. The pollen was then quickly separated from the supernatant, e.g., by ion exchange chromatography or affinity chromatography. The supernatant was loaded onto a CM-Sepharose column pre-equilibrated with 50 mM sodium acetate buffer, pH 4.5, followed by elution in the same buffer with a gradient increase in NaCl concentration from 0 to 500 mM. Further purification was by HPLC on a CM-silica gel column, using the same elution conditions as used for CM-Sepharose column.

Avicel (10 milligrams) in 1 mL 50 mnM sodium acetate buffer, pH 4.5, was incubated in buffer, with expansin alone, with cellulase (100 micrograms of Trichoderma cellulase (Behringer)) alone and with both cellulase and 0–50 micrograms of purified maize pollen expansin (Zea m 1) or expansin from cucumber walls.

The samples were incubated, with agitation, at room temperature for 0–30 h. Time-dependent production of reducing sugars was detected by reaction with PABAH reagent and absorbance was measured at 410 nm.

FIG. 24 shows the curves generated from measuring release of reducing sugars from the degradation of Avicel incubated with 10 micrograms of beta expansin over a 24 hour period. The results demonstrate that the total amount of breakdown of cellulose is greater when treated with both expansin and cellulase, compared to using cellulase alone. There was an approximate doubling of the end point of cellulytic activity, indicating that expansin increased the overall degradation of cellulose, as well as increased the rate of degradation. We take this result to mean though not wishing it to be bound thereto that expansin is opening up additional glucan sites for cellulase action, resulting in an enhanced breakdown of cellulose. The initial rate of Avicel breakdown is faster when expansin is added to cellulase, and the difference in the rate of cellulose degradation between cellulase alone and cellulase plus expansin increases with time. The expansin effect is not short lived, and improves long-term cellulytic activity.

A similar expansin effect results using 50 micrograms of expansin (FIG. 25).

In further tests, the amount of expansin added to the preparation was varied. Addition of 30 and 10 micrograms of expansin yielded equivalent effect FIG. 26, whereas 3 micrograms and 1 microgram had less effect (FIG. 27).

Cucumber alpha-expansins (30 microgram/mL), demonstrated enhancement of cellulose breakdown. See FIG. 28.

The synergistic enhancement of cellulose hydrolysis was also demonstrated when filter paper (Whatman grade 3) was used as the substrate (FIG. 29). This form of cellulose is more ordered and more crystalline than the microcrystalline form of Avicel.

Expansin also enhanced degradation of cellulose pre-digested with cellulase. For these experiments, Avicel was first digested for 24 hours in 100 micrograms/mL of Trichoderma cellulases. Then the Avicel was thoroughly washed and further incubated with cellulase plus or minus expansin. The assay results showed that as found with previously untreated Avicel, the hydrolysis of pre-digested Avicel was enhanced by inclusion of Zea m 1 expansin. The results are shown in FIG. 30.

CONCLUSIONS

The data provided in Example 18 demonstrate that expansins are able to enhance the long-term and end-point cellulytic activity of cellulases. There was a two-fold or greater enhancement.

While we have illustrated and described the preferred embodiment of our invention, it is to be understood that this invention is capable of variation and modification, and we, therefore, do not wish or intend to be limited to the precise terms set forth, but desire and intend to avail ourselves of such changes and alterations which may be made for adapting the invention of the present invention to various usages and conditions. Accordingly, such changes and alterations are properly intended to be within the full range of equivalents and, therefore, within the purview of the following claims. The terms and expressions which have been employed in the foregoing specification are used therein as terms of description and not of limitation, and thus there is no intention in the use of such terms and expressions of excluding equivalents of features shown and described or portions thereof, it being recognized that the scope of the invention is defined and limited only by the claims which follow.

Thus is described our invention and the manner and process of making and using it in such full, clear, concise, and exact terms so as to enable any person skilled in the art to which it pertains, or with which it is most nearly connected, to make and use the same.

What is claimed is:

1. A composition for enhancement of enzymatic degradation of cellulose, comprising an expansin and an enzyme having the property of degrading cellulose.

2. The composition of claim 1 wherein the enzyme is a hydrolytic enzyme.

3. The composition of claim 2 wherein the enzyme is a cellulase.

4. The composition of claim 3 wherein the cellulase is Trichoderma cellulase.

5. A method for enhancing enzymatic degradation of cellulose comprising incubating a sample containing cellulose with an expansin and an enzyme having the property of degrading cellulose.

6. The method of claim 5 wherein the enzyme is a hydrolytic enzyme.

7. The method of claim 6 wherein the enzyme is a cellulase.

8. The method of claim 7 wherein the cellulase is Trichoderma cellulase.

9. The method of claim 8 wherein the expansin is present in an amount of at least about 0.0001 to about 0.005 times the amount of cellulose present.

10. The method of claim 8 wherein the expansin is present in an amount of at least about 0.001 times the amount of cellulose present.

11. The method of claim 8 wherein the expansin is present in an amount of at least about 0.01 to 0.5 times the amount of cellulase present.

12. The method of claim 11 wherein the expansin is present in an amount of at least about 0.1 times the amount of cellulase present.

13. The method of claim 5 wherein the sample is selected from the group consisting of a textile, paper and rope.

14. A method for enhancing the accessibility of cellulose to chemical or biological modification, comprising incubating a sample containing cellulose with an expansin and a cellulase.

15. A method for enhancing enzymatic degradation of cellulose comprising incubating a sample containing cellulose with an expansin and a cellulase, said expansin being present in an amount of at least about 0.01 to 0.5 times the amount of cellulase present.

* * * * *

UNITED STATES PATENT AND TRADEMARK OFFICE
CERTIFICATE OF CORRECTION

PATENT NO. : 6,326,470 B2  Page 1 of 1
APPLICATION NO. : 09/429675
DATED : December 4, 2001
INVENTOR(S) : Cosgrove et al.

It is certified that error appears in the above-identified patent and that said Letters Patent is hereby corrected as shown below:

<u>Col. 1, line 8</u>:

<u>ADD</u>:

--GRANT REFERENCE--

--This invention was made with support from the National Science Foundation under Grant No. MCB-9317864. The government has certain rights in the invention.--

Signed and Sealed this

Twenty-fifth Day of December, 2007

JON W. DUDAS
*Director of the United States Patent and Trademark Office*

UNITED STATES PATENT AND TRADEMARK OFFICE
CERTIFICATE OF CORRECTION

| | |
|---|---|
| PATENT NO. | : 6,326,470 B1 |
| APPLICATION NO. | : 09/429675 |
| DATED | : December 4, 2001 |
| INVENTOR(S) | : Daniel J. Cosgrive |

It is certified that error appears in the above-identified patent and that said Letters Patent is hereby corrected as shown below:

Column 1, line 8:

ADD:
--This invention was made with government support under Grant Nos. MCB-9317864 and DCB-9018028, awarded by the National Science Foundation. The Government has certain rights in the invention.--

Signed and Sealed this

Nineteenth Day of January, 2010

David J. Kappos
*Director of the United States Patent and Trademark Office*